US005830710A

United States Patent [19]
Progulske-Fox et al.

[11] Patent Number: 5,830,710
[45] Date of Patent: Nov. 3, 1998

[54] **CLONED *PORPHYROMONAS GINGIVALIS* GENES AND PROBES FOR THE DETECTION OF PERIODONTAL DISEASE**

[75] Inventors: Ann Progulske-Fox, Gainesville, Fla.; Somying Tumwasorn, Bangkok, Thailand; Guylaine Lepine, Fort Erie, Canada; Naiming Han, Gainesville, Fla.; Marilyn Lantz, Indianapolis, Ind.; Joseph M. Patti, Missouri City, Tex.

[73] Assignees: University of Florida, Gainesville, Fla.; UAB Research Foundation, Birmingham, Ala.

[21] Appl. No.: 353,485

[22] Filed: Dec. 9, 1994

Related U.S. Application Data

[63] Continuation-in-part of Ser. No. 250,997, May 31, 1994, which is a continuation of Ser. No. 647,119, Jan. 25, 1991, abandoned, which is a continuation-in-part of Ser. No. 241,640, Sep. 8, 1988, abandoned.

[51] Int. Cl.$^6$ .......................... C12P 19/34; C07H 19/00; A61K 39/02
[52] U.S. Cl. ...................... 435/911; 536/22.1; 536/23.2; 424/190.1; 424/234.1
[58] Field of Search ............................ 424/190.1, 234.1; 435/91.1; 536/22, 22.1, 23.2

[56] References Cited

U.S. PATENT DOCUMENTS

| | | |
|---|---|---|
| 4,358,535 | 11/1982 | Falkow et al. . |
| 4,661,350 | 4/1987 | Tsurumizu et al. . |
| 4,866,167 | 9/1989 | Chen et al. ............................... 536/27 |
| 5,432,055 | 7/1995 | Evans . |
| 5,475,097 | 12/1995 | Travis et al. . |
| 5,523,390 | 6/1996 | Travis et al. . |

FOREIGN PATENT DOCUMENTS

| | | |
|---|---|---|
| 9507286 | 3/1995 | WIPO . |
| WO 95/26404 | 1/1997 | WIPO . |

OTHER PUBLICATIONS

Whitlock et al Abstracts of the 93rd Gen Meeting of ASM p. 116; D–120.
Lepin, Abstract of the 93rd Gen Meeting of the ASM p. 116 D–119.
White, D.,D. Mayrand (1981) "Association of oral Bacteroids with gingivitis and adult periodontitis" Journal of Periodontal Research 16:259–265.
Takazoe, I. et al. (1984) "Colonization of he Subgingival Area by *Bacteroides gingivalis*" J. Dent. Res. 63(3):422–426.
Slots, J., E. Hausmann (1979) "Longitudinal Study of Experimentally Induced Periodontal Disease in *Macaca arctoides*: Relationship Between Microflora and Alveolar Bone Loss" Infection and Immunity 23(2):260–269.
Dusek et al Infection & Immunity 61:940–946, 1993.
Tumuasorn, Dissertation Abstract Vol. 50: p. 60 Molecular Cloning & Characterization, 1988.
Lepine Dissertation Attached Relevant pages, 1994.
Loesche et al., J. Perodontol 63:1102–1109, 1992.
Watanabe et al J. Dental Res 72:1040–1044, 1993.
Slots et al. Clin Infect Dis 16:5317–5318, 1993.
Gersdorf et al FC–MS Immunology & Medical Microb 6:109–114, 1993.
Boyd, J., B.C. McBride (1984) "Fractionation of Hemagglutinating and Bacterial Binding Adhesins of *Bacteroides gingivalis*" Infection and Immunity 45(2):403–409.
Inoshita, E. et al. (1986) "Isolation and Some Properties of Exohemagglutinin from the Culture Medium of *Bacteroides gingivalis* 381" Infection and Immunity 52(2):421–427.
Okuda, K. et al. (1986) "Purification and Properties of Hemagglituitnin from Culture Supernatant of *Bacteriodes gingivalis*" Infection and Immunity 54(3):659–665.
Naito, Y. et al. (1987) "Detection of Specific Antibody in Adult Human Periodontis Sera to Surface Antigens of *Bacteroides gingivalis*" Infection and Immunity 55(3):832–834.
Naito, Y. et al. (1985) "Monoclonal Antibodies against Surface Antigens of *Bacteriodes gingivalis*" Infection and Immunity 50(1);231–235.
Okuda, K. et al. (1986) "Antigenic Characteristics and Serological Identification of 10 Black–Pigmented Bacteroides species" Journal of Clinical Microbiology 24(1):89–95.
Abiko, Y. et al. (1988) "Gene Cloning and Expression of a *Bacteroides gingivalis*–Specific Protein Antigen in *Escherichia coli*" Adv. Dent. Res. 2(2):310–314.
Dickinson, D.P. et al. (1988) "Molecular Cloning and Sequencing of the Gene Encoding the Fimbrial Subunit Protein of *Bacteroides gingivalis*" Journal of Bacteriology 170(4):1658–1665.
Okuda, K. et al. (1988) "Protective Efficacy of Active and Passive Immunizations against Experimental Infection with *Bacteroides gingivalis* in Ligated Hamsters" J. Dent. Res. 67(5):807–811.
Mouton, C. et al. (1989) "Immunochemical Identification and Preliminary Characterization of a Nonfimbrial Hemagglutinating Adhesion of *Bacteroides gingivalis*" Infection and Immunity 57(2):566–573.
Progulske–Fox, A. et al. (1989) "The expression and function of a *Bacteroides gingivalis* hemagglutinin gene in *Escherichia coli*" Oral Microbial. Immunol. 4:121–131.
Roberts, M.C. et al. (1987) "Chromosomal DNA Probes for the Identification of *Bacteroides Species*" Journal of General Microbiology 133:1423–1430.

(List continued on next page.)

*Primary Examiner*—Susan A. Loring
*Attorney, Agent, or Firm*—Gerard H. Bencen, Esq.; Gerard H. Bencen, P.A.

[57] ABSTRACT

DNA fragments from *Porphyromonas gingivalis* which express proteins that elicit anti-*P. gingivalis* immunologic responses are described. Microorganisms, genetically modified to express *P. gingivalis* antigens, are provided. Also disclosed are probes, vaccines, and monoclonal antibodies for the detection and prevention of periodontal disease.

2 Claims, 2 Drawing Sheets

OTHER PUBLICATIONS

Dickinson, D.P. et al. (1986) "Molecular Cloning of *B. gingivalis* Fimbrial Protein Subunit Gene" J. Dental Res. 65:737, abstract No. 105.

Abiko, Y. (1986) "Cloning and Expression of *Bacteroides gingivalis* Antigen Gene into *Escherichia coli*" J. Dental Res. 65:737, abstract No. 106.

Kawamoti, Y. et al. (1991) "Purification and Immunochemical Characterization of a Recombinant Outer Membrane Protein from *Bacteroides gingivalis*" Int. J. Biochem. 23(10):1053–1061.

Roberts, M.C. et al. (1987) "Chromosomal DNA Probes for the Identification of *Bacteroides Species*" Journal of General Microbiology 133:1423–1430.

Lerner, R.A. et al. (1983) "The Development of Synthetic Vaccines" in The Biology of Immunologic Disease, Chapter 31, pp. 331–338.

Helfman, D.M., S.H. Hughes (1987) "Use of Antibodies to Screen cDNA Expession Libraries Prepared in Plasmid Vectors" Methods in Enzymology 152:451–457.

Helfman, D.M. et al. (1983) "Identification of clones that encode chicken tropomyosin by direct immunological screening of a cDNA expression library" Proc. Natl. Acad. Sci. USA 80:31–35.

Young, R.A., R.W. Davis (1983) "Efficient isolation of genes by using antibody probes" Proc. Natl. Acad. Sci. USA 80:1194–1198.

Hoiseth, S.K., B.A.D. Stocker (1981) "Aromatic–dependent *Salmonella typhimurium* are non–virulent and effective as live vaccines" Nature 291:238–239.

Brown, A. et al. (1987) "An Attenuated aroA *Salmonell typhimurium* vaccine Elicits Humoral and Cellular Immunity to Cloned β–Galactosidase in Mice" The Journal of Infectious Diseases 155(1):86–92.

Sadoff, J.C. et al. (1988) "Oral *Salmonella typhimurium* Vaccine Expressing Circumsporozoite Protein Protects Against Malaria" Science 24:336–338.

French, C.K. et al. (1987) "DNA Probe–Based Technology Compared to Standard Culture Methodology for the Detection of Periodontal Pathogens" 33(6):963.

Lepine, G. et al. (1994) "Cloning and Characterization of a Fourth Putative Hemagglutinin Gene from *Porphyromonas gingivalis*" 94th Meeting of the American Society for Microbiology, Las Vegas, NV, May 23–27, *abstract No. D–117.

Fletcher, H.M. et al. (1994) "Cloning and Characterization of a Protease Gene (prtH) from *Porphyromonas gingivalis*" Infection and Immunity 62(10):4279–4286.

Kirszbaum, L. et al. (1995) "Complete Nucleotide Sequence of a Gene prtR of *Porphymonas gingivalis* W50 Encoding a 132 kDa Protein that Contains an Arginine–Specific Thiol Endopeptidase Domain and a Haemagglutinin Domain" Biochemical and Biophysical Research Communications 207(1):424–431.

Pavloff, N. et al. (1995) "Moklecular Cloning and STructural Characterization of the Arg–Gingipain Proteinase of *Porphyromonas gingivalis*" The Journal of Biological Chemistry 270(3):1007–1010.

Hunt, J.M., D.H. Persing (1993) "acterial Detection" DNA Probes, pp. 525–564.

Dusek, D.M. et al.(1994) "Systemic and Mucsal Immune Responses in Mice Orally Immunzed with Avirulent *Salmonella typhinurium* Expressing a Cloned *Porphyromonas gingivalis* Hemagglutinin" Infectin and Immunity 62(5):1652–1657.

Schmidt et al Oral Microbiol Immunol 9:161–165 1994.

Houghton Vaccines 86, pp. 21–25.

Whitlock et al ASM Abstract .D–120, p. 116.

Progulske–Fox et al Oral Microbiology & Immunology 4: 121–131, 1989.

Progulske–Fox et al J. Periodont Res 28:473–474, 1993.

CLONED *PORPHYROMONAS GINGIVALIS* GENES AND PROBES FOR THE DETECTION OF PERIODONTAL DISEASE

CROSS-REFERENCE TO A RELATED APPLICATION

This is a continuation-in-part of co-pending application Ser. No. 08/250,997, filed May 31, 1994; which is a continuation of application Ser. No. 07/647,119, filed Jan. 25, 1991, now abandoned; which is a continuation-in-part of application Ser. No. 07/241,640, filed Sep. 8, 1988, now abandoned.

This invention was made with government support under National Institutes of Health National Institute of Dental Research Grant Nos. DE 07496, DE 00336, Research Career Development Award DE 07220, and Public Health Service Grant DE 07256. The government has certain rights in this invention.

BACKGROUND OF THE INVENTION

Periodontal disease (PD) is a chronic inflammatory disease which results in the destruction of the supporting tissues of teeth. Although the specific microbial etiology of PD is not known, it is widely accepted that bacteria are the contributing agents of the disease.

The presence of a complex microflora in the subgingival crevice has complicated the identification of the specific etiologic agents of PD. However, it appears that a few genera, primarily gram-negative anaerobes, are associated with disease progression. Several lines of evidence strongly implicate the gram-negative anaerobic bacterium *Porphyromonas gingivalis*, previously known to those skilled in the art as *Bacteroides gingivalis*, as an etiological agent of adult periodontal disease (White, D., D. Mayrand [1981] "Association of Oral Bacteroides with Gingivitis and Adult Periodontitis," *J. Periodont. Res.* 1:1–18; Takazoe, L., T. Nakamura, K. Okuda [1984] "Colonization of the Subgingival Area by *Bacteroides gingivalis*," *J. Dent. Res.* 63:422–426. For example, relatively high proportions of *P. gingivalis* have been isolated from adult periodontitis lesions, patients with adult periodontitis have been found to have higher levels of IgG antibodies to *P. gingivalis* than do normal adults, and local immunity to *P. gingivalis* is greater in the more advanced cases than in the early forms of periodontal disease. *P. gingivalis* also appears to be a causative agent of experimental periodontitis in animals (Slots, J., E. Hausmann [1979] "Longitudinal Study of Experimentally Induced Periodontal Disease in *Macaca arctoides*: Relationship Between Microflora and Alveolar Bone Loss," *Infect. Immun.* 23:260–269). In addition, *P. gingivalis* possesses a variety of suspected virulence factors such as proteases, collagenases, immunoglobulin degrading enzymes, and adhesins.

In order to exert their pathogenic effects, periodontopathic bacteria such as *P. gingivalis* must possess characteristics which enable them to colonize the host, survive in the periodontal pocket, possibly invade the gingival tissues, and to destroy the collagenous periodontal ligament, the alveolar bone, and other tissue components surrounding the tooth. Components of bacteria which mediate attachment to host tissues include surface structures such as fimbriae, capsular materials, lipopolysaccharides, and membrane-associated extracellular vesicles.

The hemagglutinating activity of *P. gingivalis* has been studied as a parameter that affects the adherence of this organism in the periodontal pocket. Sera from patients with adult periodontitis possess high antibody levels to the *P. gingivalis* hemagglutinin. It is thus suggested that the adhesive surface structures such as hemagglutinin participate in *P gingivalis* colonization and antigenic stimulation of the host.

Investigations have reported the isolation of hemagglutinin activity from *P. gingivalis*. Boyd and McBride (Boyd, J., B. C. McBride [1984] "Fractionation of Hemagglutinating and Bacterial Binding Adhesins of *Bacteroides gingivalis*," *Infect. Immun.* 45:403–409) prepared an outer membrane component containing hemagglutinating activity from *P. gingvalis* W12. This preparation contained three major proteins with molecular weights of 69,000, 41,500, and 22,000. Inoshita et al. (Inoshita, E., A. Amano, T. Hanioka, H. Tamagawa, S. Shizukushi, A. Tsunemitsu [1986] "Isolation and Some Properties of Exohemagglutinin from the Culture Medium of *Bacteroides gingivalis* 381," *Infect. Immun.* 52:421–427) isolated hemagglutinating activity from culture supernatants of *P. gingivalis* 381. The isolated hemagglutinin component contains three major proteins with molecular weights of 24,000, 37,000, and 44,000. Okuda et al (Okuda, K, A. Yamanoto, Y. Naito, I. Takazoe, J. Slots, R. J. Genco [1986] "Purification and Properties of Hemagglutinin from Culture Supernatant of *Bacteroides gingivalis*," *Infect. Immun.* 5 55:659–665) also purified a hemagglutinin of *P. gingivalis* 381 from culture supernatant which appears to have vesicle or tubelike structures and is comprised mainly of a 40,000 molecular-weight protein. Their recent report indicated that sera from most patients with adult periodontitis reacts to the hemagglutinin antigen at 43,000 and 57,000 molecular weights (Naito, Y., K. Okuda, I. Takazoe [1987] "Detection of Specific Antibody in Adult Human Periodontitis Sera to Surface Antigens of *Bacteroides gingivalis*," *Infect. Immun.* 55(3):832–834).

Recombinant DNA techniques have proven to be powerful tools for the study of pathogenesis. However, recombinant DNA techniques have been applied only sparingly to the study of gram-negative anaerobic pathogens and even less to the study of the molecular mechanisms of periodontopathogenesis. The recombinant DNA methodologies offer advantages over previous methods used in the study of oral pathogens. For example, the cloning of *P. gingivalis* antigens allows for a genetic and molecular analysis of the gene(s) which presently is difficult due to the lack of knowledge about the genetic system in *P. gingivalis*.

BRIEF SUMMARY OF THE INVENTION

Genes have been cloned and the proteins encoded thereby have been isolated from organisms associated with periodontal disease (PD). In particular, genes from *Porphyromonas gingivalis*, which is an etiological agent of adult PD have been identified, characterized, and sequenced. These genes have also been ligated to an appropriate vector and used to transform an appropriate host cell. The recombinant cells express antigens which elicit immunological responses. Antigens expressed by the *P. gingivalis* clones are also identified and described here.

The invention provides, inter alia, a means of detecting the presence of disease-causing *P. gingivalis*. The detection method involves the use of DNA probes and antibody probes which selectively identify the presence of these bacteria. Also provided are polypeptides which can be used for the production of antibodies to the organisms associated with PD. The antibodies selectively and specifically bind to the subject proteins and can be utilized in purification and identification procedures. These genes and polypeptides can be used as a vaccine against PD. Further, a means of producing monoclonal antibodies for the antigens associated with periodontal disease is also provided.

BRIEF DESCRIPTION OF THE SEQUENCES

Figure 1:
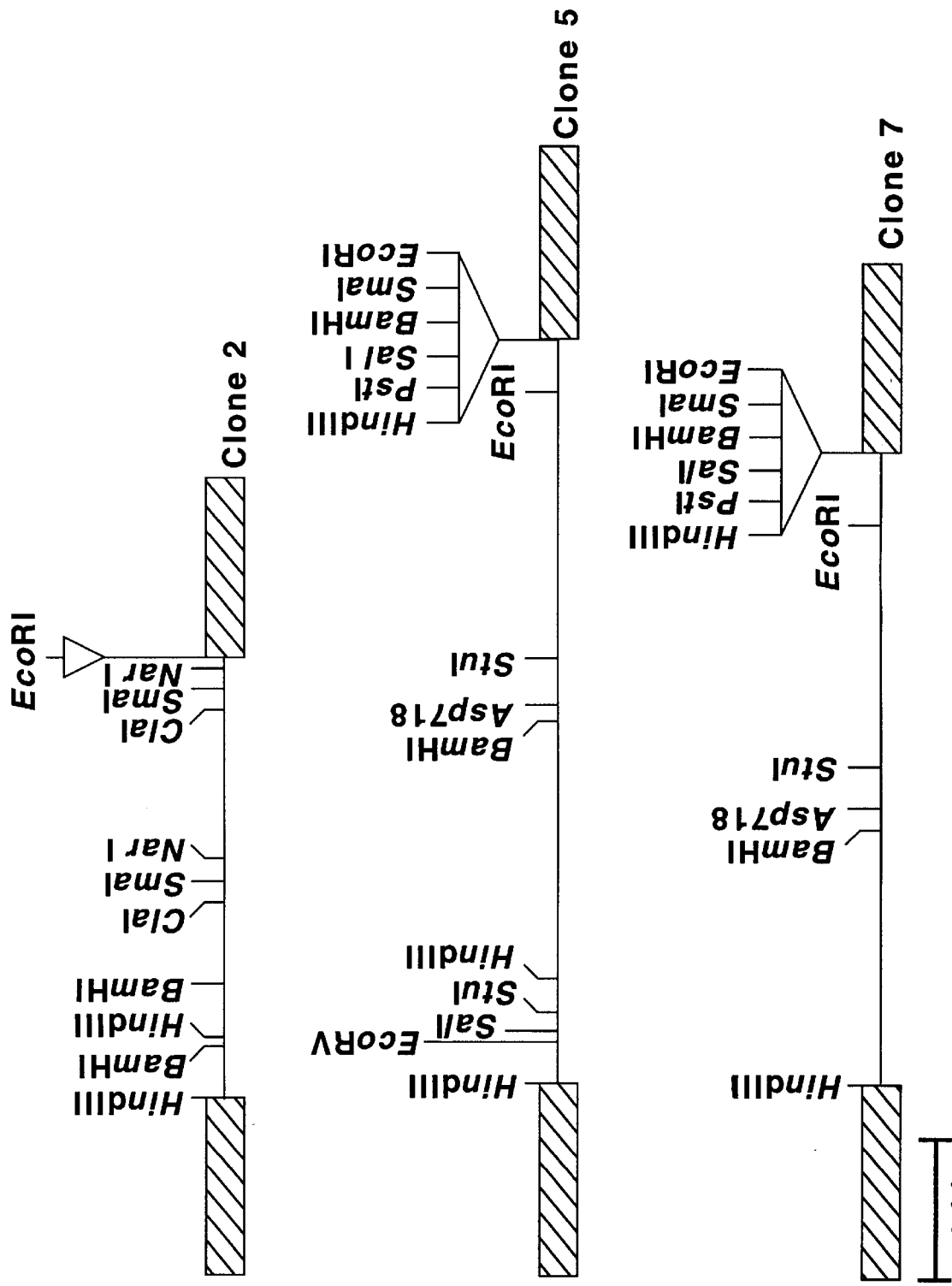
FIG. 1 shows a schematic diagram of restriction enzyme recognition sites of recombinant plasmids from clones 2, 5, and 7. The solid lines represent *P. gingivalis* DNA inserts. The hatched boxes represent pUC9 regions.
Figure 2:
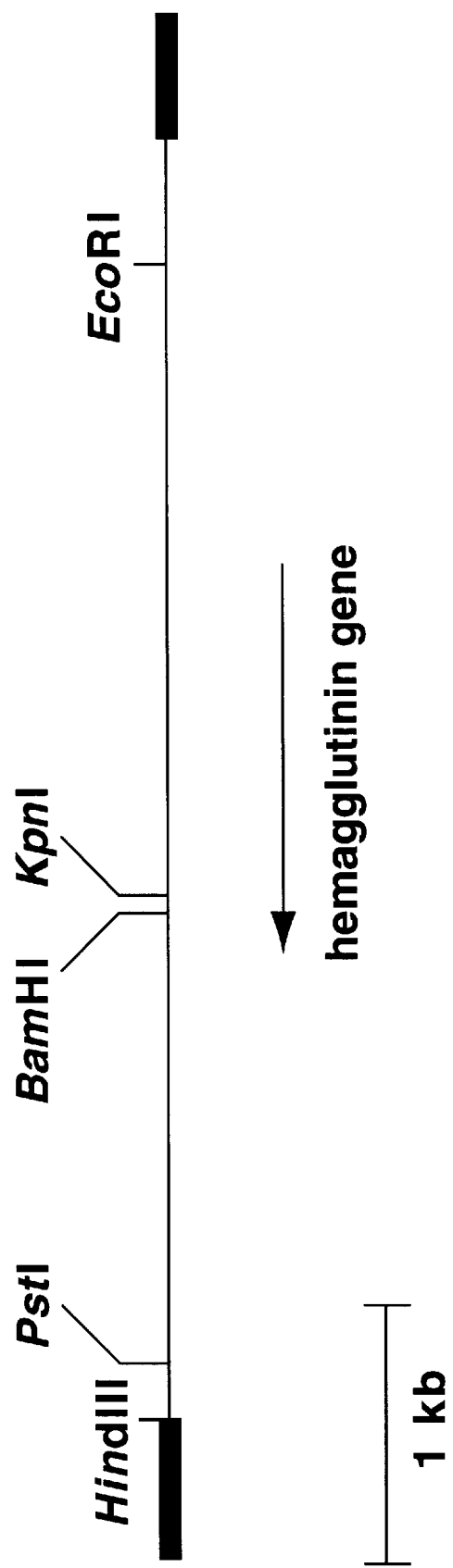
FIG. 2 shows a restriction map of a hemagglutinin gene, hag B. The hemagglutinin gene is contained on a HindIII fragment in pUC9.

SEQ ID NO. 1 is the nucleotide sequence of the hemagglutinin gene designated hag A.

SEQ ID NO. 2 is the derived amino acid sequence of the polypeptide encoded by the hag A gene.

SEQ ID NO. 3 is the nucleotide sequence of the hemagglutinin gene designated hag B.

SEQ ID NO. 4 is the derived amino acid sequence of the polypeptide encoded by the hag B gene.

SEQ ID NO. 5 is the nucleotide sequence of the hemagglutinin gene designated hag C.

SEQ ID NO. 6 is the derived amino acid sequence of the polypeptide encoded by the hag C gene.

SEQ ID NO. 7 is the nucleotide sequence of the hemagglutinin gene designated hag D.

SEQ ID NO. 8 is derived amino acid sequence of the polypeptide encoded by the hag D gene.

SEQ ID NO. 9 is the nucleotide sequence of the gene designated prtP.

SEQ ID NO. 10 is the derived amino acid sequence of the polypeptide encoded by the prtP gene.

SEQ ID NO. 11 is primer APF 147 used according to the subject invention.

SEQ ID NO. 12 is primer APF 148 used according to the subject invention.

DETAILED DESCRIPTION OF THE INVENTION

The DNA sequences of the present invention comprise structural genes encoding proteins which can be involved in the pathogenesis of bacteria responsible for periodontal disease. The genes of the subject invention can be isolated from the DNA of *Porphyromonas gingivalis*. The genes of the subject invention are further characterized by determination of their nucleotide sequences. After obtaining the DNA, a gene library can be developed and the resulting DNA fragments inserted into suitable cloning vectors which are introduced into a compatible host. Depending on the particular host used, the vector can include various regulatory and other regions, usually including an origin of replication, and one or more promoter regions and markers for the selection of transformants. In general, the vectors will provide regulatory signals for expression, amplification, and for a regulated response to a variety of conditions and reagents.

Various markers can be employed for the selection of transformants, including biocide resistance, particularly to antibiotics such as ampicillin, tetracycline, trimethoprim, chloramphenicol, and penicillin; toxins, such as colicin; and heavy metals, such as mercuric salts. Alternatively, complementation providing an essential nutrient to an auxotrophic host can be employed.

Hosts which may be employed for the production of the polypeptides of the present invention include unicellular microorganisms, such as prokaryotes, i.e., bacteria; and eukaryotes, such as fungi, including yeasts, algae, protozoa, molds, and the like. Specific bacteria which are susceptible to transformation include members of the Enterobacteriaceae, such as strains of *Escherichia coli*; Salmonella; Bacillaceae, such as *Bacillus subtilis*; Pneumococcus; Streptococcus; *Haemophilus influenzae*, and yeasts such as Saccharomyces, among others.

The DNA sequences can be introduced directly into the genome of the host or can first be incorporated into a vector which is then introduced into the host. Exemplary methods of direct incorporation include transduction by recombinant phage or cosmids, transfection where specially treated host bacterial cells can be caused to take up naked phage chromosomes, and transformation by calcium precipitation. These methods are well known in the art. Exemplary vectors include plasmids, cosmids, and phages.

Genomic libraries of *P. gingivalis* DNA were constructed in known plasmid expression vectors. For example, the plasmid expression vector, pUC9, contains the pBR 322 origin of replication, the pBR 322 ampicillin resistance gene, and a portion of the lac Z gene of *E. Coli* which codes for the α-peptide of β-galactosidase. The amino terminus of the lac Z gene contains a polylinker region which has multiple unique cloning sites. Transformation of *E. coli* JM109, which is defective in β-galactosidase, with pUC9 complements the bacterial β-galactosidase activity, resulting in the ability of the bacterial cell to metabolize the lactose analog X-GAL to a blue color. Cloned DNA inserted in the polylinker region interrupts the lac Z gene of the plasmid. Therefore *E. coli* transformants resulting from recombinant plasmids are unable to metabolize X-GAL and appear as white colonies on X-GAL containing plates.

*E. coli* clones were isolated which stably exhibited *P. gingivalis* antigen expression. These antigens were detected in intact cells both by filter-binding enzyme immunoassay and ELISA. One of these clones, clone 2, was found to encode a polypeptide with an average molecular weight of greater than 125 kD, seen in polyacrylamide gels and detected by Western blot analysis. This polypeptide was later determined to be greater than 144 kD. Expression of the *P. gingivalis* antigen in clone 2 occurs either in the presence or absence of IPTG but is enhanced by IPTG stimulation. The expression of the clone 3 antigen was also found to be stimulated by IPTG in the same manner as clone 2.

When antigen-expressing clones were surveyed for functional activities, clones 2, 5, and 7 were able to agglutinate erythrocytes whereas *E. coli* JM109 (pUC9) was not. The restriction maps and Southern blot hybridization of these clones indicated that clone 2 cells contain a Porphyromonas DNA insert different from clones 5 and 7. Clone 5, which is also able to autoagglutinate, has a 760 bp DNA fragment in addition to a 4,800 bp fragment in common with the clone 7 insert. Subcloning of these two fragments in different orientations revealed that the 4,800 bp DNA encoded for the hemagglutinating activity and the 760 bp DNA for the autoagglutinating activity. Both fragments must contain a Porphyromonas promoter since the subclones with opposite orientations of the inserts still express functional proteins, indicating that antigen expression of clones 5 and 7 is not stimulated by IPTG.

Western blot analysis of clones 5 and 7 and minicell analysis of the subclones further revealed that the *P. gingi-*

*valis* DNA fragment encoded polypeptides of approximately 16 kD and approximately 49–50 kD. These polypeptides were sized using SDS-PAGE, under denaturing conditions. A native 49–50 kD protein was also purified by immunoaffinity chromatography. No other purified 49–50 kD protein associated with hemagglutination has been reported. Therefore, the 49–50 kD protein is a previously undetected surface antigen involved in hemagglutination.

E. coli adsorbed rabbit-polyclonal antibody against clone 2 was found to react with several bands in the *P. gingivalis* cell lysate preparation separated by SDS-PAGE. The most rapidly developing and strongest reaction appeared at two bands of 43 kD and 38 kD. Two bands of 32 kD and 30 kD appeared later and three faint bands of 110 kD, 90 kD and 75 kD sometimes were visible still later. This strongly suggests that the *P. gingivalis* hemagglutinin is expressed in clone 2.

*E. Coli* adsorbed rabbit-polyclonal antibody against clones 5 and 7 also reacted with two bands of 43 kD and 38 kD, but barely reacted with the higher bands of 110 kD, 90 kD, and 75 kD, and did not react with the bands of 32 kD and 30 kD. Thus, clones 5 and 7 contain DNA inserts which are nonhomologous with clone 2 and express different antigenic epitopes, but all function as hemagglutinin. The clone 7 insert contains a Porphyromonas promoter but the clone 2 insert does not. An *E. coli* host (clone 2) has been designated *E. Coli* pST 2 and deposited with the American Type Culture Collection (ATCC), 12301 Parklawn Drive, Rockville, Md. 20852. Also, an *E. coli* host (clone 5) has been designated *E. coli* pST 5 and it, too, has been deposited with the ATCC. These deposits were assigned the following accession numbers:

| Culture | Accession number | Deposit date |
| --- | --- | --- |
| *E. coli* pST 2 | ATCC 67733 | June 24, 1988 |
| *E. coli* pST 5 | ATCC 67734 | June 24, 1988 |

The subject cultures have been deposited under conditions that assure access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action. Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least 30 (thirty) years after the date of deposit or for the enforceable life of any patent which may issue disclosing the cultures. The depositor acknowledges the duty to replace a deposit should the depository be unable to furnish a sample when requested. All restrictions on the availability to the public of the subject culture deposits will be irrevocably removed upon the granting of a patent disclosing them.

The novel genes disclosed and claimed herein can be probed out of the *E. coli* strains which have been deposited with the ATCC. The isolation of these genes can be performed using techniques which are well-known in the molecular biology art. The isolated genes can be inserted into appropriate vehicles which can then be used to transform another microbe.

It is well understood in the field of biotechnology that the subject genes and gene products have many valuable uses. For example, the genes themselves comprising nucleic acid sequences can be used to specifically and selectively probe other nucleic acid sequences to determine the presence of homologous sequences therein. This use of the subject nucleotide sequences, or fragments thereof, as probes can have advantageous applications in their use as a diagnostic tool, identifying organisms or other transformants that have nucleic acid sequences which are sufficiently homologous such that, using standard procedures and conditions, hybridization can occur between the test sequences and the probe. As used herein, substantial sequence homology refers to homology which is sufficient to enable the variant to function in the same capacity as the original probe. Preferably, this homology is greater than 50%; more preferably, this homology is greater than 75%; and most preferably, this homology is greater than 90%. The degree of homology needed for the variant to function in its intended capacity will depend upon the intended use of the sequence. It is well within the skill of a person trained in this art to make mutational, insertional, and deletional mutations which are designated to improve the function of the sequence or otherwise provide a methodological advantage.

In addition, the subject nucleotide and fragments thereof can be sequences useful as primers in the preparation and manufacture of sequences by polymerase chain reaction (PCR), inverse polymerase chain reaction (IPCR), or other nucleic acid synthesis methods. Obviously, the subject genes and fragments can be useful for the production of the gene product, i.e., the antigen or polypeptides encoded thereby.

Mutations, insertions, and deletions can be produced in a given polynucleotide sequence in many ways, and these methods are known to the ordinary skilled artisan. Other methods may be come known in the future.

The known methods include, but are not limited to:

(1) synthesizing chemically or otherwise an artificial sequence which is a mutation, insertion or deletion of the known sequence;

(2) using a probe of the present invention to obtain via hybridization a new sequence or a mutation, insertion or deletion of the probe sequence; and (3) mutating, inserting or deleting a test sequence in vitro or in vivo.

It is important to note that the mutational, insertional, and deletional variants generated from a given probe may be more or less efficient than the original probe. Notwithstanding such differences in efficiency, these variants are within the scope of the present invention. Thus, mutational, insertional, and deletional variants of the disclosed sequences can be readily prepared by methods which are well known to those skilled in the art. These variants can be used in the same manner as the instant probes so long as the variants have substantial sequence homology with the probes.

The gene products can also have a variety of uses. For example, the antigens so produced by a gene in a transformed host can be useful in the production of antibodies to the antigen. Those antibodies can be used as probes, when labeled, or can be used in affinity separation techniques. These polypeptides can also be useful as molecular weight markers in chromatographic or electrophoretic procedures, or the like, where molecular weights are used to characterize an unknown polypeptide or identify or confirm the existence of a known polypeptide.

Following are examples which illustrate materials, methods and procedures, including the best mode, for practicing the invention. These examples are illustrative and should not be construed as limiting.

EXAMPLE 1

Preparation of Chromosomal DNA

*Porphyromonas gingivalis* 381 obtained from a stock culture was grown on plates containing Trypticase soy agar (MBL Microbiology Systems, Cockeysville, Md.) supplemented with sheep blood (5%), hemin (5 µg/ml), and menadione (5 µg/ml). The organism was also grown in 10 ml of Todd-Hewitt broth (BBL) supplemented with hemin (5 µg/ml), menadione (5 µg/ml) and glucose (2 mg/ml). Cultures were incubated in an anaerobic chamber in a $N_2$-$H_2$-$CO_2$ (85:10:5) atmosphere at 37° C. until the log phase of growth was obtained. The 10 ml broth culture was transferred into 25 ml of the same medium and subsequently transferred to 500 ml of medium. Incubation was at 37° C. anaerobically until a late log phase culture was obtained. *E. coli* JM109 [rec A1, end A1, gyr A96, thi, hsd R17 sup E44, rel A1, (lac-pro AN), (F;tra D36, proAB, lac IZ M15)] and the plasmid expression vector pUC9 have been described previously (Viera, J., J. Messing [1982] "The pUC Plasmids, an M13 mp 7-Derived System for Insertion Mutagenesis and Sequencing with Synthetic Universal Primers," *Gene* 19:259–268). *E. coli* JM109 was cultured in Luria-Bertani (LB) medium consisting of Bacto-tryptone (10 g/l), Bacto-yeast extract (5 g/l), and NaCi (5 g/l). For solid media, Bacto-agar was added at a final concentration of 15 g/l. *E. coli* JM109 transformants were selected and maintained on LB plates containing 50 µg of ampicillin/ml.

Next, chromosomal DNA from *P. gingivalis* 381 was prepared as follows: One to three liters of cells were pelleted by centrifugation and washed once with 1× SSC buffer (0.87% NaCl, 0.04% sodium citrate) containing 27% sucrose and 10 mM ethylenediaminetetraacetic acid (EDTA). The cells were pelleted and resuspended in 1/50 of the original volume of the same buffer at 4° C. Lysozyme (5 mg/ml) in SSC was added to 0.5 mg/ml; the mixture was mixed thoroughly and incubated at 37° C. for 10 minutes. Nine volumes of 1% SSC containing 27% sucrose 10 mM EDTA and 1.11% SDS (prewarmed to 39° C.) were added and the cell suspension was incubated at 37° C. for 10 to 30 minutes until cell lysis was complete. In order to denature any contaminating proteins, proteinase K was added to a final concentration of 1 mg/ml and the lysate was incubated at 37° C. for 4 hours. DNA was extracted twice with phenol, twice with phenol-chloroform (1:1 by volume), and four times with chloroform. Two volumes of absolute alcohol were added and the precipitated DNA was spooled onto a glass rod. The purified DNA was rinsed with 70% ethanol and suspended in TE buffer, pH 8.0 (10 mM Tris-HCl pH 8.0, 1 mM EDTA).

Alternatively chromosomal DNA was isolated from *P. gingivalis* 381 by a method of CTAB (hexadecyltrimethyl ammonium bromide)/CsCl ultracentrifugation. Briefly, 0.4–0.5 g wet cells was resuspended in 9.5 ml TE buffer (10 mM Tris/Cl, pH 8.0, 1 mM EDTA, pH 8.0), and then 0.5 ml of 10% SDS, and 50 µl of 20 mg/ml proteinase K were added and incubated for 1 hour at 37° C. Then 1.8 ml of 5M NaCl and 1.5 ml CTAB/NaCl were added and incubated 20 minutes at 65° C. The mixture was extracted with Chloroform/isoamyl alcohol and precipitated with 0.6 volume isopropanol. DNA pellet was dissolved in 20 TE buffer and 20 g CsCl and 500 µl of 10 mg/ml ethidium bromide were added and centrifuged 30 minutes at 12,000 rpm using a Beckman GA-20 rotor. The supernatant was then centrifuged in a Beckman VTi50 rotor for 18 hours at 45,000 rpm. DNA band was collected under long wave UV lamp and ethidium bromide was removed by water saturated butanol extraction and dialyzed against TE buffer thoroughly to remove CsCl.

Chromosomal DNA from the *P. gingivalis* strain W12 can be obtained by similar methods.

EXAMPLE 2

Isolation of Plasmid DNA and Construction of Genomic Libraries

Plasmid DNA was isolated by the method of Ish-Horowicz and Burke (Ish-Horowicz, D., J. F. Burke [1981] "Rapid and Efficient Cosmid Cloning," *Nucleic Acids Res.* 9:2989–2998) in which cells were lysed with SDS-EDTA in the presence of NaOH. Potassium acetate, pH 4.8, was added at 4° C. and cell debris, protein, RNA, and chromosomal DNA were removed by centrifugation. The plasmid was precipitated with two volumes of ethanol, washed with 70% ethanol, dried, and resuspended in TE buffer at pH 7.5. The plasmid was separated from contaminating RNA and any remaining chromosomal DNA by cesium chloride density centrifugation in the presence of ethidium bromide. Ethidium bromide and cesium chloride were removed by butanol extraction and dialysis, respectively. The dialyzed plasmid was then phenol-chloroform extracted, ethanol precipitated, and resuspended in TE buffer.

Purified *P. gingivalis* DNA was then partially digested with Sau3A restriction endonuclease to create fragments of 2–10 kilobases which were ligated to the dephosphorylated BamHI site of vector pUC9 with $T_4$ DNA ligase by standard methods (Maniatis, T., E. F. Fritsch, J. Sambrook [1982] *Molecular Cloning: A Laboratory Manual*, Cold Spring Harbor Laboratory, Cold Spring Harbor, N.Y.). Genomic fragments were also obtained by partial digestion of the chromosomal DNA with HindIII restriction endonuclease and ligated to the dephosphorylated HindIII site of pUC9. The recombinant plasmids were used to transform *E. coli* JM109. *E. coli* JM109 was grown to an early log phase ($OD_{550}$=0.2) in LB broth. Ten ml of the culture were centrifuged at 5,000 rpm, for 5 minutes at 4° C. and resuspended in 2 ml of transformation buffer 1 (TFM 1, 10 mM Tris-HCl, pH 7.5, 0.15M NaCl). The cells were then pelleted and resuspended in 2 ml of TFM 2 (50 mM $CaCl_2$) and incubated on ice for 45 minutes. The cells were again pelleted and gently resuspended in 3 ml of TFM 2, and dispensed into 0.2 ml aliquots. One-tenth ml of TFM 3 (10 mM Tris-HCl, pH 7.5, 50 mM $CaCl_2$, 10 mM $MgSO_4$) was added to each aliquot followed by varying amounts of DNA. The cells were then allowed to incubate on ice for 45 minutes, and heat shocked at 37° C. for 2 minutes. LB broth (0.5 ml) was added and the cell suspension was incubated at 37° C. for 1 hour. Finally, the cells were plated on LB agar containing ampicillin (50 µg/ml) and 5-bromo-4-chloro-3-indolyl-β-D-galactopyranoside (X-GAL) (200 µg/ml) and incubated for 24 to 48 hours at 37° C. All transformants were stored at–70° C. in LB broth with ampicillin (50 µg/ml) and 20% glycerol.

EXAMPLE 3

Preparation of Antisera and Assay of Antibody Titer

Late exponential phase cells of *P. gingivalis* strain 381 were pelleted, washed with 0.01M phosphate-buffered saline (PBS) pH 7.2, and resuspended in PBS and 0.01 sodium azide at 4° C. for at least 1 hour. The cells were again washed with PBS, resuspended to a concentration of $1 \times 10^9$ cells/ml and emulsified in an equal volume of Freund's incomplete adjuvant. The cell emulsion was injected in 3 doses at two week intervals for 4 weeks subcutaneously in the back of adult New Zealand rabbits. Each rabbit was given a booster dose 50 to 60 days later. Antisera were collected from the marginal ear veins just prior to immunization and beginning one week after the booster dose. All sera were stored at −20° C.

Rabbit anti-*P. gingivalis* antiserum was adsorbed 4 times with *E. coli* JM109 harboring pUC9 plasmid [*E. coli* JM109 (pUC9)]. For each adsorption, *E. coli* cells from 1 liter of a stationary phase culture were washed and mixed with 3 ml of serum at 4° C. for 1 hour. The serum was recovered by pelleting the cells at 5,000×g for 20 minutes. For sonicate adsorption, *E. coli* cells from 500 ml of stationary phase growth suspended in 5 ml PBS were disrupted by sonication and mixed with *E. coli* cell-adsorbed serum for 1 hour at 4° C. The mixture was centrifuged at 100,000×g for 1 hour and the resulting clear serum was stored at −20° C.

Sera were then tested for anti-*P. gingivalis* and anti-*E. coli* activities by an enzyme-linked immunosorbent assay (ELISA). *P. gingivalis* cells suspended in carbonate-bicarbonate buffer, pH 9.6 ($10^8$ cells per well) were fixed to microtiter plates at 4° C. overnight. After the wells were washed with 0.5% "TWEEN-20" in PBS, 1% bovine serum albumin (BSA) in PBS was added to each well, and the plates were incubated for 2 hours at room temperature in order to saturate the binding sites. After washing the plates, serially diluted antiserum was added and plates were incubated for 1 hour at room temperature followed by a second wash with 0.5% "TWEEN-20" in PBS. Peroxidase conjugated goat anti-rabbit IgG, diluted 1:1000 in 1% BSA, was added and the plates were again incubated at room temperature for 1 hour. After a final washing, a color-forming substrate solution (0-phenylenediamine, 0.5 g/100 ml in 0.1M citrate buffer, pH 4.5, and 1.8% hydrogen peroxide) was added, and the plates were incubated for 30 minutes at room temperature. The absorbance at 492 nm was measured with a Titertek Multiscan reader. An absorbance of 0.05 or more over background was considered positive. Background readings were obtained from the wells in which all reagents except anti-*P. gingivalis* antiserum was added. Normal rabbit serum was also tested against *P. gingivalis* antigen. To test the effectiveness of adsorption, the titers of treated sera were assayed as described above except that *E. coli* JM109 (pUC9) whole cells were used as the antigen.

It was found that rabbit anti-*P. gingivalis* antiserum had an antibody titer of 1:64,000 to *P. gingivalis* and 1:160 to *E. coli* (pUC9), whereas normal rabbit serum had an antibody titer of 1:10 to *P. gingivalis* and 1:80 to *E. coli* (pUC9). Adsorption of anti-*P. gingivalis* antiserum with *E. coli* (pUC9) resulted in a slight reduction of antibody titer to *P. gingivalis* and reduced the anti-*E. coli* titer to zero or 1:10.

EXAMPLE 4

Filter-Binding Enzyme Immunoassay

Ampicillin-resistant transformants which formed white colonies in the presence of X-GAL were spotted onto LB agar plates with ampicillin, grown overnight, and blotted onto nitrocellulose filter disks. *P. gingivalis* and *E. Coli* JM109 (pUC9) were also spotted onto each filter as a positive and negative control, respectively. Duplicate prints of the colonies on nitrocellulose filters were made and colonies on one of each duplicate print were lysed by a 15-minute exposure to chloroform vapor. Filters were then air dried for 30 minutes and soaked for 2 hours in PBS containing 3% BSA. After the filters were washed, adsorbed rabbit anti-*P. gingivalis* antiserum was added and the filters were incubated in a solution of peroxidase conjugated goat anti-rabbit immunoglobulin for 1 hour. After washing, the filters were developed in a color-forming substrate solution consisting of 0.06% 4-chloro-1-naphthol and 3% hydrogen peroxide in a 1:4 solution of methanol-TBS (50 mM Tris hydrochloride, 200 mM NaCl, pH 7.4). Clones which developed a blue color were picked and rescreened by the same procedure.

A total of 1,700 colonies of transformants resulting from HindIII restricted chromosomal DNA were tested for the expression of *P. gingivalis* antigens. Seven clones gave positive signals.

EXAMPLE 5

Restriction and Southern Blot Analysis of Recombinant Plasmids

To further confirm the positive results of the filter-binding enzyme immunoassay, plasmid DNA was isolated from each positive clone. Electrophoresis of these unrestricted plasmids showed that each clone contained only one recombinant plasmid.

Southern blot analysis was also performed to confirm that the DNA inserts were derived from the *P. gingivalis* DNA. Plasmids were isolated from all the clones that were positive in the filter-binding enzyme immunoassay. Restriction endonuclease digestions were performed under conditions described by the manufacturer to produce complete digestion. Agarose gel electrophoresis was performed as described by Maniatis et al. (1982, supra).

Recombinant plasmid and pUC9 vector DNAs were digested to completion with the appropriate restriction enzymes and run on a 1.2% agarose gel. *P. gingivalis* DNA partially digested with Sau3A, and HindIII-digested *Eikenella corrodens* clone 18 DNA were also loaded in the gel. The DNA was transferred to "BIODYNE" nylon membrane by Southern transfer (Southern, E.M. [1975] "Detection of Specific Sequences Among DNA Fragments Separated by Gel Electrophoresis," *J. Mol. Biol.* 98:503–517). *P. gingivalis* DNA partially digested with HindIII was nick translated with ($\alpha$-$^{32}$P dCTP) (400 Ci/mmol, Amersham Corp., Arlington Heights, Ill.) as described by Maniatis et al. (1982, supra). The membrane-bound DNA was hybridized to the nick-translated probe at 42° C. in 50% formamide for 16 hours by the method recommended by the manufacturer (Pall Ultrafine Filtration Corp., Glen Cove, N.Y.) which was adapted from Wahl et al. (Wahl, G. M., M. Stern, G. R. Stark [1979] "Efficient Transfer of Large DNA Fragments from Agarose Gels to Diazobenzyloxy-Methyl-Paper and Rapid Hybridization by Using Dextran Sulfate," *Proc. Natl. Acad. Sci. USA* 76:3683–3687). The membrane was washed at room temperature in wash buffer (2×SSC and 0.1% SDS) four times each for 5 minutes and twice at 50° C. each for 15 minutes in 0.1×SSC, 0.1% SDS. An autoradiogram was obtained with Kodak XAR-5 film (Eastman Kodak Co., Rochester, N.Y.) and Cronex Quanta II intensifying screen (DuPont Co., Wilmington, Del.). Clones 1, 2, 4, 5, 7, and 8 were generated from HindIII-restricted chromosomal DNA After digestion with HindIII, only clones 5, 6, 7, and 8 revealed fragments of the linear pUC9 vector and fragments of *P. gingivalis* DNA inserts. Plasmid DNAs of these clones were restricted with various enzymes and analyzed by gel electrophoresis. The estimated size of inserts of clones 5, 6, 7, and 8 are 5.5, 5.5, 4.8, and 3.5 kb, respectively (Table 1). Thus clones 5 and 6 were found to contain plasmids of the same size and identical restriction fragments.

Clone 3, which was constructed by ligation of Sau3A partially digested *P. gingivalis* DNA with BamHI cut pUC9, was restricted with SmaI and SalI. Restriction analysis revealed a fragment of linear 9 bp-deleted pUC9 and 2 fragments of insert. Restriction analysis with different enzymes showed that the size of the insert of clone 3 was approximately 1.1 kb.

Although clones 1, 2, and 4 were generated from HindIII restricted DNA, they did not result in fragments of linear pUC9 after HindIII digestion. These cloned DNAs were then restricted with PvuII, which generates a 307 bp fragment containing the polylinker-cloning sites from pUC9. Clones 1, 2 and 4 revealed fragments of linear 307 bp-deleted pUC9 and inserts associated with the deleted fragment. These cloned DNAs were digested with various restriction enzymes and analyzed by agarose gel electrophoresis. The size of inserts of clones 1, 2, and 4 were found to be 3.2, 3.2, and 3.3 kb, respectively (Table 1). Clones 1 and 2 also contained plasmids of the same size and identical restriction fragments.

TABLE 1

Characterization of *E. coli* transformants which express *P. gingivalis* antigens

| Clone No. | Colonies reacted with antiserum unlysed | lysed | Size of *B. gingivalis* DNA cloned (Kb) |
|---|---|---|---|
| 1 and 2 | +[a] | + | 3.2 |
| 3 | + | + | 1.1 |
| 4 | + | + | 3.3 |
| 5 and 6 | + | + | 5.5 |
| 7 | + | + | 4.8 |
| 8 | –[b] | + | 3.5 |

[a] = Positive reaction
[b] = Negative, not reactive

EXAMPLE 6

Assay of the Titer of Anti-*P. gingivalis* Antiserum to *E. coli* Transformants Which Express *P. gingivalis* Antigens Cultures of each representative clone were prepared by 100-fold dilution of overnight cultures and grown for 2 hours at 37° C. Isopropyl-β-D-thiogalactopyranoside (IPTG) was added to specific cultures at a final concentration of 1 mM and the cells were pelleted by centrifugation 4 hours later. The cells were washed, resuspended in 1/10 volume of PBS, and the optical density of each suspension was determined at 550 nm. Cell lysate antigen was prepared by breaking the cells with a sonicator. The protein concentration of each lysate was determined by the Bio-Rad protein assay (Bio-Rad Laboratories, Richmond, Calif.). Determination of the titer of anti-*P. gingivalis* 381 against these antigens was performed with the ELISA as described above ($10^8$ cells or 1 µg protein per well). Normal rabbit serum exhaustively adsorbed with *E. Coli* JM109 (pUC9) was also tested in the same manner. Anti-*P. gingivalis* antiserum was able to detect antigen expression in all positive clones except clone 8 in an enzyme-linked immunosorbent assay (ELISA). The antiserum reacted with both whole cell and cell lysate antigens. Isopropyl-β-D-thiogalactopyranoside (IPTG) was not necessary to induce antigen expression. However, in the presence of IPTG, clones 2 and 3 showed higher antigen expression, especially when the cell lysate preparations were tested. These results are shown in Table 2.

TABLE 2

Titer of anti-*P. gingivalis* antiserum against *E. coli* transformants which express *P. gingivalis* antigens

| | Antibody titers[a] against test antigens[b] | | | |
|---|---|---|---|---|
| | Whole cell | | Cell Lysate | |
| Organism | IPTG– | IPTG+ | IPTG– | IPTG+ |
| Clone 1 | 320 | NT[c] | 320–640 | NT |
| Clone 2 | 320 | 640 | 320–640 | 1280–2560 |
| Clone 3 | 20 | 160 | 40–160 | 1280 |
| Clone 4 | 20–100 | 20–40 | 20–40 | 20–40 |
| Clone 5 | 40–80 | 40–80 | 40–80 | 40–80 |
| Clone 6 | 40 | NT | 40 | NT |
| Clone 7 | 40 | 40 | 40 | 40 |
| Clone 8 | 0 | 0 | 0 | NT |
| *E. coli* JM109 (pUC9) | 0–10 | 0–10 | 0–10 | 0–10 |
| *P. gingivalis* Control NRS[d] | 40,960–64,000 | NT | NT | NT |

[a] Number designates the reciprocal dilution of the sera which gave $OD_{492}$ reading of 0.05 or more over the background. Antiserum was exhaustively adsorbed with *E. coli* JM109 (pUC9).
[b] Antigens were prepared from cultures grown without IPTG (IPTG–) or in the presence of IPTG (IPTG+).
[c] Not tested.
[d] Normal rabbit serum exhaustively adsorbed with *E. coli* JM109 (pUC9) did not react to test antigens.

EXAMPLE 7

Sodium Dodecyl Sulfate—Polyacrylamide Gel Electrophoresis (SDS-PAGE)

Five stable representative clones were analyzed for antigen expression by SDS-PAGE. Each of the representative antigen-producing clones was grown to mid-log phase in 3.0 ml of LB broth with 50 µg of ampicillin/ml. The cells were pelleted, washed with PBS, resuspended in 0.3 ml of sample buffer (62.5 mM Tris-hydrochloride, 5% 2-mercaptoethanol, 2% SDS, 10% glycerol, 0.002% bromphenol blue, pH 6.8), and boiled for three minutes. The *P. gingivalis* cell lysate was mixed with an equal volume of sample buffer and treated in the same manner.

SDS-PAGE was performed using a 12% polyacrylamide gel in a vertical slab gel electrophoresis tank (Hoefer Scientific Instruments, San Francisco, Calif.) as described by Laemmli (Laemmli, U.K. [1970] "Cleavage of Structural Proteins During the Assembly of the Head of Bacteriophage T4," *Nature* (London) 227:680–685). A whole cell preparation from clone 2 was separated in a 5% SDS polyacrylamide gel and the expressed protein was initially estimated to have a molecular weight of more than 125 kD and later determined to be greater than 144 kD.

EXAMPLE 8

Assay for Removal of SHA Adherence Inhibition by Anti-*P. gingvalis* Antiserum

The expression of components detected by in vitro methods was subjected to further examination. The antigen-expressing clones described in the previous examples were tested for the expression of adhesins for saliva-treated hydroxyapatite (SHA adhesin). Anti-*P. gingivalis* 381 antiserum which inhibits the adherence of *P. gingivalis* 381 to SHA was adsorbed with each antigen-expressing clone until the titer of the antiserum to each clone was reduced to zero. Each adsorbed antiserum was tested for inhibition of *P. gingivalis* adherence to SHAM.

*Porphyromonas gingivalis* 381 was cultured in Todd-Hewitt broth. *E. coli* transformants were cultured in LB medium containing 50 μg of ampicillin/ml by preparing 100-fold dilutions of overnight cultures followed by incubation for 2 hours at 37° C. IPTG was added to the cultures, when used at a final concentration of 1 mM, and the cultures were incubated for an additional 4 hours.

An assay for the removal of SHA adherence inhibition using anti-*P. gingivalis* antiserum was used to test for SHA adherence. In order to do this, aliquots of anti-*P. gingivalis* antiserum were adsorbed with each antigen-expressing clone as well as *E. coli* JM109 (pUC9). The titer of each adsorbed antiserum was tested against each clone and *P. gingivalis* whole cell antigen by ELISA as described above.

Whole paraffin-stimulated human saliva was collected and heated at 56° C. for 30 minutes to inactivate degradative enzymes. Extraneous debris and cells were removed by centrifugation at 12,000 rpm for 10 minutes and sodium azide was added to a final concentration of 0.04%.

Hydroxyapatite (HA) beads (BDH Biochemical, Lt., Poole, England) were treated as previously described (Clark, W. B., L. L. Bammann, R. J. Gibbons [1978] "Comparative Estimates of Bacterial Affinities and Adsorption Sites on Hydroxyapatite Surfaces," *Infect. Immun.* 19:846–853). Briefly, 10 mg of beads were washed and hydrated in distilled water in 250 μl plastic microfuge tubes followed by equilibrium overnight with adsorption buffer (0.05M KCl, 1 mM $K_2HPO_4$, pH 7.3, 1 mM $CaCl_2$ and 0.1 mM $MgCl_2$). The beads were incubated with 200 μl of saliva for 24 hours at 4° C. and then washed with sterile adsorption buffer to remove nonadsorbing material. Control tubes without HA were treated identically.

*P. gingivalis* 381 cells were labeled by growth to late log phase in medium supplemented with ($^3$H) thymidine (10 mCi/ml). The cells were pelleted, washed twice in adsorption buffer, and dispersed with three 10-second pulses (medium power) with a microultrasonic cell disrupter.

The dispersed cells were mixed with each antiserum (1:100 dilution) and normal rabbit serum to a final concentration of 4×10$^6$ cell/ml. The cell-antiserum suspensions (200 μl) were then added to the SHA beads in microfuge tubes and the tubes were rotated in an anaerobic chamber for 1 hour. Labeled cells alone (no antisera) were treated in the same manner to determine the number of cells adhering to the SHA surface. A control tube containing cells but no SHA was tested to quantitate the amount of cells bound to the tubes rather than to the SHA. One hundred microliters of adsorption buffer containing unadhered cells was removed and placed in minivials containing 3 ml of aqueous scintillation cocktail (Amersham/Searle, Arlington Heights, Ill.), and counted with a scintillation counter (Model 455 Parkard Tricarb). Determination of the number of cells adhering to the SHA was done by subtracting the number of cells (no. of counts) in solution from the total number of cells (no. of counts) which did not adhere to the tube.

The results in Table 3 summarize the SHA inhibition data and indicate that the antiserum adsorbed with each antigen-expressing clone still inhibited the adherence of *P. gingivalis*.

TABLE 3

Inhibition of adherence to SHA by adsorbed anti-*P. gingivalis*

| Inhibitor and dilution | | % adherence[a] | % inhibition[b] |
|---|---|---|---|
| None | | 83.85 | — |
| Normal rabbit serum | 1:100 | 80.08 | 0.05 |
| Antiserum unadsorbed | 1:100 | 22.70 | 72.15 |
| Antiserum adsorbed with: | | | |
| *E. coli* JM109 (pUC9) | 1:100 | 21.57 | 73.07 |
| Clone 2 | 1:100 | 10.73 | 86.59 |
| Clone 3 | 1:100 | 22.60 | 71.78 |
| Clone 4 | 1:100 | 16.24 | 79.71 |
| Clone 5 | 1:100 | 27.37 | 65.82 |
| Clone 7 | 1:100 | 19.90 | 75.15 |

[a]Percent adherence was calculated from the following formula: % adherence = [(cpm from tube without SHA − cpm from tube with SHA)/(cpm from tube without SHA)] × 100.
[b]Percent inhibition was calculated from the following formula: % inhibition = [1 − (% adherence in the presence of antibody / % adherence in the absence of antibody)] × 100.

EXAMPLE 9

Direct Hemagglutination Assay

The rationale to identify the clones which express hemagglutinin were analogous to those described for the SHA adhesin. The anti-*P. gingivalis* antiserum adsorbed with each antigen-expressing clone and *E. coli* JM109 (pUC9), as described for the SHA assay, were tested for removal of hemagglutination inhibition activity of anti-*P. gingivalis* antiserum. Since it is necessary to determine the minimum number of *P. gingivalis* cells which produce hemagglutinin before performing the hemagglutination inhibition assay, a direct hemagglutination assay of antigen-expressing clones together with *P. gingivalis* was first performed.

A direct hemagglutination assay was used to test for adhesion to erythrocytes. The hemagglutination assays were carried out in V-bottom microtiter plates (Dynatech Laboratories, Inc., Alexandria, Va.). Erythrocytes (sheep or human group O) were washed three times with PBS (0.02M phosphate buffered saline), pH 7.2, and resuspended to a final concentration of 0.2% (v/v). Cells of *P. gingivalis* and antigen-expressing clones were washed twice in PBS and resuspended to an optical density of 0.5 and 2.0, respectively, at 660 nm. The cell suspensions were diluted in a twofold series with PBS and 0.05 ml of the suspensions were added to the wells. *E. coli* JM109 (pUC9), which was prepared in the same manner as the antigen-expressing clones, was included as a control. An equal volume (0.05 ml) of washed erythrocytes was added and mixed with the bacterial cells. The plates were stored for 16 hours at 4° C. and then examined for evidence of hemagglutination as follows. Agglutinated erythrocytes will settle as clumps which will be dispersed throughout the bottom of the wells, resulting in a pinkish-red coating of each well. In the absence of hemagglutination, the erythrocytes will settle on the bottom of the well as a central, smooth, bright red round disk. The titer was expressed as the reciprocal of the highest dilution showing positive agglutination.

The hemagglutination inhibition assay was also carried out in V-bottom microtiter plates. *P. gingivalis* cell suspensions in PBS were adjusted to the optical density of 0.5 at 660 nm. Each antiserum examined for hemagglutination inhibition activity was diluted twofold in a series of wells.

Fifty microliters of the bacterial suspension containing twice the minimum number of cells which produced hemagglutination was then added to each well. After incubation with gentle shaking at room temperature for 1 hour, 0.05 ml of the washed erythrocytes were added to each well and mixed. The plates are left for 16 hours at 4° C. and read for hemagglutination as described above for the hemagglutination assay. The titer was expressed as the reciprocal of the highest dilution showing hemagglutination inhibition.

E. coli transformants which were able to agglutinate erythrocytes were grown in LB broth containing ampicillin as described above. Two rabbits were injected with each clone as previously described. Sera were exhaustively adsorbed with E. coli JM109 (pUC9) and tested for anti-P. gingivalis activity by ELISA.

Anti-clone 2 antiserum diluted 1:10 was separately adsorbed with P. gingivalis, E. coli JM109 (pUC9), and clones 2, 5, and 7. Washed stationary phase cells of each bacterial culture were prepared as described above. For each adsorption, $10^7$, $10^8$, $10^9$ and $10^{10}$ bacterial cells were mixed with 200µl of serum and the suspensions were stored at 4° C. overnight. The sera were recovered by centrifugation at 12,000×g for 10 minutes. Each adsorbed antiserum was assayed by ELISA to determine the titer to P. gingivalis.

The direct hemagglutination assay of these clones demonstrated that clones 2, 5, and 7 did agglutinate sheep erythrocytes, whereas E. coli JM109 (pUC9) did not. The hemagglutination titer of clone 2 was 2 and that of clones 5 and 7 agglutinated erythrocytes at the undiluted suspension. In addition, clone 5 was found to auto-agglutinate when resuspended in PBS, pH 7.2.

EXAMPLE 10

DNA Restriction Mapping and Characterization Procedures

Restriction endonuclease digestions of the recombinant plasmids from clones 2, 5, and 7 were performed according to manufacturer's directions. Clone 5 DNA was digested with Hin dIII and two fragments of P. gingivalis inserts were isolated from agarose gels by the method of Zhu et al (Zhu, J. W. Kempenaers, D. Van der Straeten, R. Contreras, W. Fiers [1985] "A Method for Fast and Pure DNA Elution from Agarose Gels by Centrifugal Filtration," *Biotech.* 3:1014–1016) employing centrifugal filtration of DNA fragments through a Millipore membrane inside a conical tip. The DNA preparations were extracted with phenol-chloroform, precipitated with ethanol and resuspended in TE, pH 8.0. Each DNA fragment was ligated to HindIII-digested pUC9 and the resulting recombinant plasmids were transformed into competent E. coli JM109 cells as described previously. Recombinant plasmids from these transformants were isolated by rapid plasmid DNA isolation (Silhavy, T. J., M. L. Berman, L. W. Enquist [1984] *Experiments with Gene Fusions*, Cold Spring Harbor Laboratory, Cold Spring Harbor, N.Y.), digested with appropriate restriction endonucleases, and analyzed by agarose gel electrophoresis.

The recombinant plasmids of clones, 2, 5, and 7 were restricted with several restriction endonucleases and analyzed in 1.2% agarose gels. A schematic diagram of restriction enzyme recognition sites of these three clones is detailed in FIG. 1. These data show that the clone 2 insert is different from that of clones 5 and 7, whereas clones 5 and 7 have one insert fragment in common. The restriction map of clone 2 revealed that the HindIII site of the DNA insert at the amino terminal end of the β-galactosidase gene was still intact, but a deletion occurred at the other end of the insert and included most of the linker. The linker region with recognition sites of PstI, SalI, BamHI and SmaI was deleted but the EcoRI site was still intact as well as other sites upstream such as PvuII and NarI.

To further confirm the results of the restriction maps, $^{32}$P-labeled clone 7 recombinant DNA was used as a probe for hybridization of restricted recombinant plasmids by Southern blot analysis. Clone 2 DNA restricted with HindIII, EcoRI, and SmaI resulted in DNA fragments of pUC9 and four pieces of insert of approximately 1,400, 1,300, 420, and 150 bp. Clone 5 DNA restricted with HindIII resulted in fragments of pUC9 and two pieces of insert approximately 4,800 and 760 bp. Fragment bands of pUC9 and inserts of approximately 2,800, 2,000, and 760 bp were generated from digestion of clone 5 DNA with HindIII and BamHI. Clone 7 DNA restricted with HindIII alone and HindIII together with BamHI resulted in pUC9 and an insert of 4,800 bp, and pUC9, insert of 2,800 and 2,000 bp, respectively.

Hybridization of these transferred restricted DNAs demonstrated that the clone 7 probe hybridized to pUC9 and the common insert of clones 5 and 7 but not to the insert of clone 2.

Clone 5 was found to agglutinate erythrocytes and autoagglutinate, while clone 7 was only able to agglutinate erythrocytes. Clone 5 has an insert of 760 bp in addition to the common insert of 4,800 bp of clone 7. This data suggested that the 760 bp insert might encode for the autoagglutinating activity and the 4,800 bp fragment for the hemagglutinating activity of clone 5. The recombinant plasmid of clone 5 was thus digested with HindIII to generate pUC9 and inserts of 4,800 and 760 bp. Each insert band was isolated from these transformants and digested with restriction endonucleases. Subclones with different orientations of the insert were obtained. Subclones of 760 bp inserts were designated clone 5.1 and 5.2 and the subclones of 4,800 bp inserts, clone 5.3 and 5.4. Recombinant plasmids of clones 5.1 and 5.2 digested with HindIII did result in pUC9 and the 760 bp inserts, and different patterns of restricted DNAs were seen when digested with SalI. HindIII-restricted recombinant plasmids of clones 5.3 and 5.4 revealed pUC9 and inserts of 4,800 bp, while EcoRI-restricted recombinant plasmids showed different patterns. Both clones 5.1 and 5.2 were able to autoagglutinate when resuspended in PBS, pH 7.2, but could not agglutinate erythrocytes. Clones 5.3 and 5.4 were both able to agglutinate erythrocytes but did not autoagglutinate.

EXAMPLE 11

Identification and Characterization of Gene Products by Sodium Dodecyl Sulfate-Polyacrylamide Gel Electrophoresis (SDS-PAGE), Western Blot, Minicell Analysis, and Immunoaffinity Chromatography P. gingivalis cell lysate and cells of E. coli transformants were prepared and analyzed by SDS-PAGE as described above and Western blot as described by Burnette (Burnette, W. N. [1981] "Western Blotting: Electrophoretic transfer of proteins from sodium dodecyl sulfate-polyacrylamide gels to radiographic detection with antibody and radioiodinated protein A," *Anal. Biochem.* 112:195–203). Antisera to clones 2, 5, and 7 exhaustively adsorbed with E. coli JM109 (pUC9) were used as probes in the Western blot. Control antisera included anti-clone 2 antiserum also adsorbed with P. gingivalis at the ratio of $10^{10}$ cells per 100 μl of antiserum, and antiserum to E. coli JM109 harboring pUC9 with Eikenella corrodens DNA insert.

Upon Western blot analysis of clone 2, a protein antigen of approximately 125 kD and a smear of lower molecular weight were detected using E. coli adsorbed anti-P. gingivalis antiserum but no corresponding antigens expressed in clones 5 and 7 were detected by Western blot analysis. Clones 5 and 7 did, however, express a protein detected as a major band of approximate M.W. 49–50 kD by Western blot analysis and revealed an additional minor band of 27 kD upon minicell autoradiography.

For the identification of clones 5 and 7 gene products, the minicell procedure was used as described by Clark-Curtiss et al. and Dougan et al. (Clark-Curtiss, J. E., R. Curtiss III [1983] "Analysis of Recombinant DNA Using Escherichia coli Minicells," *Methods Enzymol.* 101:347–362; Dougan, G., M. Kehoe [1984] "The minicell system as a method for studying expression from plasmid DNA," *Methods Microbiol.* 17:233–258). Recombinant plasmids were transformed into E. coli as previously described. Transformants were selected on LB plates containing 50 μg/ml ampicillin and 10 mM isopropyl-β-D-thiogalactopyranoside (IPTG). Colonies were streaked for isolation and grown overnight at 37° C. in BSG (phosphate-buffered saline+0.01% gelatin) containing 50 μg/ml ampicillin. Minicells were then isolated by sequential low speed centrifugation, high speed centrifugation of the low speed supernatant fluid, and centrifugation through a 5–30% (w/v) sucrose gradient. The sucrose gradient centrifugation was repeated at least once. The minicells were collected and diluted twofold in BSG, pelleted by centrifugation at 10,000 rpm for 10 minutes, and the resulting pellet was resuspended in minicell labeling medium containing no methionine. After incubation of the minicell suspension for 10 minutes at 37° C., 10 μCi of $^{35}$S-methionine were added. Following a 15 minute incubation, the cells were chilled for 10 minutes on ice and pelleted by a two minute centrifugation in a microfuge. The cell pellets were then processed for SDS-PAGE. Autoradiography was performed on $^{35}$S-methionine labeled minicell preparations which were electrophoresed on a 12% SDS-PAGE.

In order to determine the native P. gingivalis antigens which clone 2 expressed, antisera against clone 2 were made in rabbits for use as a probe in Western blot analysis. Pooled anti-clone 2 antiserum had a titer of 1:16,000 against P. gingivalis whole cell antigen. This antiserum was adsorbed exhaustively with E. coli JM109 (pUC9) until the anti-E. coli titer was reduced from 1:50,000 to 1:10 in the E. coli whole cell ELISA. The adsorbed antiserum, diluted to 1:200, was used as a probe to detect antigens separated in a 12.5% SDS polyacrylamide gel and transferred to a nitrocellulose sheet. This antiserum reacted with two major bands of approximately MWs 43,000 and 38,000 and two bands of MWs 32,000 and 30,000 in P. gingivalis cell lysate antigen and the 125 kD protein band of expressed antigen in clone 2. Normal rabbit serum reacted to a common 40,000 molecular weight band of all the clones and E. coli JM109 (pUC9).

In order to prove that the P. gingivalis reactive polypeptides are exclusively P. gingivalis proteins, the native P. gingivalis antigens were reacted to E. coli adsorbed anti-clone 2 antiserum, P. gingivalis cell lysate antigen and clone 2 whole cell antigen were again separated in 12.5% SDS-polyacrylamide gel. Upon transfer to a nitrocellulose sheet, each was reacted with (1) E. coli adsorbed anti-clone 2 antiserum, (2) P. gingivalis adsorbed anti-clone 2 antiserum, and (3) antisera to E. coli JM109 harboring pUC9 with an Eikenella corrodens DNA insert. E. coli adsorbed anti-clone 2 reacted to P. gingivalis cell lysate at two major bands of MWs 43,000 and 33,000, two bands of MWs 32,000 and 30,000 and three faint bands of higher molecular weight of approximately 110,000, 90,000 and 75,000 daltons. This adsorbed antiserum also reacted to a band of expressed antigen having a molecular weight greater than 125 kD in clone 2.

To define the native P. gingivalis antigens which clones 5 and 7 expressed, antisera against clones 5 and 7 were also made in rabbits and had titers of 1:800 and 1:1,600 to P. gingivalis antigens. These antisera exhaustively adsorbed with E. Coli were used to identify the reactive native P. gingivalis antigens. Antisera against clones 5 and 7 at the dilution of 1:5 and 1:10 were found to react with two bands of approximately 43,000 and 38,000 daltons in P. gingivalis cell lysate antigen preparation but did not react to the expressed clone 2 antigen. This antiserum also reacted to a common band of approximately 36,000 daltons of E. Coli antigen in each clone and E. coli JM109 (pUC9). Normal rabbit serum did not react to any P. gingivalis antigens.

Immunoaffinity chromatography was used to identify and purify the native P. gingivalis gene product and to verify that inserts of clones 5 and 7 contained the entire gene. Immune rabbit IgG was purified via DEAE cellulose. Following the precipitation of IgG by the addition of saturated ammonium sulfate to the sera, the IgG was coupled to "AFFI-GEL" (Bio-Rad Laboratories, Richmond, Calif.) by incubation for two hours at room temperature and overnight at 4° C. The coupled material was then used to prepare a 3 cm$^3$ column. After the column was washed extensively with 0.02M phosphate buffer, pH 8.0, 1–2 ml of P. gingivalis 381 sonicate containing 18 mg/ml protein were added and run through the column using a peristaltic pump generating a flow rate of 20 ml/hr. The column eluate was monitored for absorbance at 280 nm. The column retentate was eluted from the column by addition of 0.1M glycine, pH 2.5. The recovered retentates were concentrated by centrifugation through a molecular weight cut-off filter, pressure concentration in an Amicon filter (Amicon, Danvers, Mass.), lyophilization, or a combination of the above. When a P. gingivalis 381 cell lysate was applied to an affinity column containing anti-clone 7 rabbit IgG, and the retained antigenic peptides were eluted and analyzed by SDS-PAGE, a major band at 49–50 kD was evident.

EXAMPLE 12

Determination of the Relationship Between the Expressed Antigens of Clones 2, 5 and 7

Although antisera against clones 2, 5, and 7 reacted to P. gingivalis cell lysate at two major bands of 43,000 and 38,000 MWs, E. coli adsorbed anti-clone 2 antiserum also reacted to the greater than 125 kD protein band synthesized in clone 2. However, E. coli adsorbed anti-clone 5 and anti-clone 7 antisera did not react to this expressed antigen band of clone 2.

To further define the relationship of the epitopes of the expressed antigen in clone 2 from that of clones 5 and 7, adsorption of anti-clone 2 antiserum with several antigens was performed and each adsorbed anti-clone 2 antiserum was tested for its titer to P. gingivalis whole cell antigen by ELISA. The antibody titer to P. gingivalis of anti-clone 2 antiserum was removed in a dose response manner by adsorption with P. gingivalis and clone 2 cells. Adsorption with E. coli JM109 (pUC9), clone 5 or clone 7 did not reduce the antibody titer to P. gingivalis of anti-clone 2 antiserum.

The ability of antisera to *P. gingivalis* and hemagglutinable *E. coli* to inhibit the hemagglutinating activity of *P. gingivalis* was determined and is summarized in Table 4. All antisera inhibited *P. gingivalis* hemagglutination at titers four to eight times that of normal rabbit sera.

TABLE 4

Inhibition of hemagglutinating activity of *P. gingivalis* by anti-hemagglutinating *E. coli* antisera.

| Antiserum | Hemagglutination inhibition titer |
|---|---|
| Anti-*P. gingivalis* | |
| unadsorbed | 640 |
| adsorbed with *E. Coli* JM109 (pUC9) | 640 |
| Normal rabbit serum[a] | 160 |
| Anti-clone 2 | 320–640 |
| Preimmune | 80 |
| Anti-clone 5 | 160 |
| Preimmune | 40 |
| Anti-clone 7 | 160 |
| Preimmune | 40 |

[a]Normal rabbit serum and preimmune sera titers are from each particular group of rabbits.

EXAMPLE 13

DNA Sequencing of *P. gingivalis* Hemagglutinin Genes

The *P. gingivalis* 381 chromosome contains at least four genes which encode hemagglutinin. The *P. gingivalis* genes encoding hemagglutinin proteins have been designated hag A, hag B, hag C, and hag D. Genes encoding hemagglutinins were cloned using standard procedures as described above or with minor modifications as readily recognized and understood in the art. Plasmid DNA was isolated from the transformed hosts by a rapid method wherein DNA samples for sequencing were prepared by alkaline-lysis/PEG precipitation method. Briefly, transformed *E. coli* JM 109 cells growing in 50 ml Terrific broth with ampicillin were collected (ca. 0.5 g wet weight) and resuspended in 2 ml of 50 mM glucose, 25 mM Tris/Cl (pH 8.0), and 10mM EDTA (pH 8.0). A freshly prepared 4 ml solution of 0.2N NaOH, 1% SDS was added and left on ice for 10 minutes. Then 3 ml of ice-cooled potassium acetate solution was added and left on ice for 10 minutes. The mixture was centrifuged 30 minutes at 9,000 rpm at 4° C. and RNase A was added to a final concentration of 20 μg/ml to the supernatant and incubated for 20 minutes at 37° C. The mixture was extracted thoroughly with chloroform/isoamyl alcohol. An equal volume of isopropanol was added to precipitate DNA, left for minutes at room temperature, and centrifuged for 30 minutes at 9,000 rpm at room temperature. The DNA pellet was dissolved in 3.36 ml of $H_2O$. Then 0.64 ml of 5M NaCl and 4 ml of 13% PEG 8000 (polyethylene glycol, Sigma) were added and left on ice for more than 1 hour. After centrifugation for 15 minutes at 9,000 rpm at 4° C., the DNA pellet was dissolved in sterilized water. By this method, 200 to 400 μg of highly purified plasmid DNA can be obtained in one day.

A. Characterization of the hag A gene and gene product. The hemagglutinin gene designated hag A was obtained from the *P. gingivalis* 381-derived clone ST 2, and was determined to be more than 4500 bp in length. The sequence is shown in SEQ ID NO. 1. Inverse polymerase chain reaction (IPCR) was employed to determine the complete sequence of a gene, and was used to obtain the flanking 5' and 3' sequences and thus the entire nucleotide sequence of the hag A gene. The open reading frame (ORF) of the hag A gene was determined to encode a polypeptide of at least 1339 amino acids, and >144 kD. The derived amino acid sequence encoded by the hag A gene is shown in SEQ ID NO. 2. It was found that hag A sequence has an approximately 1.1 kb repeating unit which repeats at least four times and may repeat as many as six times, with only minor differences in the repeat unit.

To ensure that the complete hag A gene sequence was isolated from clone 2, chromosome DNA samples were digested by restriction enzymes which did not cut the original cloned fragment clone 2, including AccI, AseI, (Biolabs) VspI (the isoschizomer from Promega), BclI, BglII, BstXI, DraI (BRL), EcoRV, NruI (Stratagene), PstI, PvuII, SalI, SphI, SspI, SstI (Sigma), StuI, and XhoI. The digested fragments were transferred to positive-charged nylon membranes (Boeringer Mannheim Biochemicas, Indianapolis, Ind.) by capillary transfer method. The whole ST2 fragment was labeled and detected by nonradioactive Genius Kit (Boeringer Mannheim Biochemicas). The results were made visible on X-Ray films by Lumi-phos 530 system (Boeringer Mannheim Biochemicas).

To carry out the IPCR procedure, two 18 mer oligo primers, negative primer at position nt 224 and positive primer at position nt 2032, were chosen and synthesized at University of Florida DNA Synthesis Core Lab.

The total AseI (VspI) digested fragments and the 3–7 kb fragments extracted from agarose gel were self-ligated at a DNA concentration of 1–10 ng/μl with 1 U of T4DNA ligase (Promega) per 50 μl reaction mixture for 16 hours at 16° C, respectively. Then, the ligation mixture was heated for 15 minutes at 65° and extracted with phenol/chloroform, chloroform, precipitated with ethanol and resuspended in sterilized distilled water. IPCR reactions were performed in 2 steps: first, the self-ligated DNA sample in buffer was heated for 30 minutes at 94° C; then, Taq polymerase (Promega) was added and cycled using a PTC-100 Programmable Thermal Controller (MJ Research, Inc., Watertown, Mass.). We used 35 cycles of denaturation at 94° C. for 1 minute, primer annealing at 52° C. for 1 minute, and extension at 72° C. for 5 minutes.

The amplified mixture was extracted with phenol/chloroform, chloroform and electrophoresed at 1% low melting agarose gel. The excised fragment was then treated with agarase (Boeringer Mannheim Biochemicas). The DNA samples treated with agarase are purified enough for direct sequencing. After analysis of direct sequencing data, the amplified IPCR fragment was cut by HindIII and KpnI and cloned into pBluescript II SK and transformed in *E. coli* JM 109. Several subclones were constructed and one oligo primer was also synthesized to complete the sequencing.

Sequencing of the hag A gene was carried out at the University of Florida DNA Sequencing Core lab using the Taq Dye Primer and Taq Dyedeoxy Terminator Cycle Sequencing Protocol developed by ABI (Applied Biosystems, Inc., Foster City, Calif.) with fluorescent labeled primer(s) and labeled dideoxy nucleotides, respectively. The labeled extension were analyzed on an ABI 373 DNA Sequencer.

The hemagglutinin (HA) encoded by the hag A gene can have the characterisitics of a cysteine protease, a trypsin-like protease, and a hemagglutinin. The DNA sequence of hag A was compared with the DNA sequence of an approximately 4.5 kb fragment of genomic DNA from the λFBPl clone made from the of *P. gingivalis* W12 strain. The gene from the λFBP1 clone was isolated and named prtP (see Example 13, section E, below). The prtP gene encodes protein(s) reactive with antibody that inhibits a cysteine protease of *P. gingivalis* W12, and that binds a fibrinogen. The nucleotide sequences of hag A and prtP were compared, and were found to contain internal regions approximately 2 kb in size that share a high degree of sequence similarity. The hag A gene contains three regions that share greater than 90% sequence identity with prtP. These regions include a 217 bp sequence in which there is 90% identity, and a 884 bp sequence in which there is 94% identity and a 500 bp sequence in which there is 97% identity. These findings raise the possibility of relatedness between fibrinogen binding protein and a hemagglutinin of *P. gingivalis*.

B. Characterization of hag B gene and gene product. The gene encoding a hemagglutinin hag B was obtained for sequencing from *P. gingivalis* on a 2.0 kb HindIII BamHI fragment and 2.4 kb BamHI-EcoRI fragment cloned into pUC9 and transformed into *E. coli* JM109. These fragments were subcloned into the M13 bacteriophage vectors for sequencing (Yannish-Peron, C., J. Viera, J. Messing [1985] "Improved M13 phage cloning vectors and host strains: Nucleotide sequences of M13mp18 and pUC9 vectors," Gene 33:103–119). The entire lengths of these fragments were sequenced utilizing the universal priming site of M13 and by synthesizing oligonucleotide primers for the remaining regions of the fragments. The sequencing of the 1.7 kb KpnI-PstI fragment and the DNA adjacent to the BamHI site ensured that the 2.0 kb and 2.4 kb fragments were contiguous. *E. coli* JM109 was used as the host strain for transfection with M13 and grown in 2× YT broth. Recombinant phages were detected by using soft agar (0.75%) overlays of 2× YT broth base supplemented with 0.33 mM isopropyl-beta-D-thiogalactopyranoside (IPTG) and 0.02% 5-bromo-4-chloro-3-indolyl-3-galactoside (X-GAL).

Restriction enzymes, T4 DNA ligase, and M13 17-mer primer were purchased from either Bethesda Research Laboratories (Gaithersburg, Md.) or Fischer Scientific Co., St. Louis, Mo.) and were used in accordance with the specifications of the manufacturers. Other oligonucleotide primers were synthesized by the Molecular Biology Resource Facility (Oklahoma City, Okla). Sequencing reagents were from the T7 Sequencing Kit of Pharmacia (Piscataway, N.J.) or the Sequenase DNA sequencing kit of U.S. Biochemical Corp. (Cleveland, Ohio). The [α-$^{35}$S]dATP was purchased from DuPont, NEN Research Products (Boston, Mass.). IPTG and X-GAL were purchased from Sigma Chemical Co. (St. Louis, Mo.).

DNA sequencing was performed by using the dideoxy chain-termination method (Sanger, F., S. Nicklen, A. R. Coulson [1977] "DNA sequencing with chain terminating inhibitors," *Proc. Natl. Acad. Sci. USA* 74:5463–5467). Different portions of each fragment were sequenced from synthesized oligonucleotide primers. The DNA sequence of the gene was determined for both strands and was analyzed by the James M. Pustell DNA and protein sequencing program (International Biotechnologies, Inc., New Haven, Conn.). The nucleotide sequence of the hag B hemagglutinin gene is 1053 nucleotides in length as shown in SEQ ID NO. 3. The mol. % G+C content is 59.9%. The reading frame of the hemagglutinin gene was defined by a putative ribosome binding site and promoters upstream of the ATG start codon and potential stem-loop structures downstream of the stop codon. Beginning 181 to 239 bases upstream of the two potential promoters was a region of direct repeats. A sequence of 41 nucleotides was repeated four times contiguously with only minor differences. Open reading frames were also identified on the opposite strands both upstream and downstream of the hemagglutinin gene.

The amino acid sequence of the hemagglutinin was derived from the nucleotide sequence and determined to be 350 residues in length. The derived protein of $M_r$=39,375 was basic with an isoelectric point of 8.98 and hydrophilic. A potential signal peptide is evident. Cleavage is most probable after amino acids 32–36, though none of these sites conforms ideally to the −3,−1 rules of von Heijne. The derived amino acid sequence encoded by the hag B gene is shown in SEQ ID NO. 4.

Comparison of the nucleotide and derived amino acid sequences with the gene and protein bank libraries did not uncover any significant homology between the hemagglutinin and previously determined sequences.

Upstream from the hemagglutinin reading frame were two potential promoters which in turn were preceded by a series of direct repeats. The function of the direct repeats is not known but it would be reasonable to hypothesize that they have a role in gene expression.

The codon usage for the hemagglutinin was examined and found to follow the pattern for a gene with low level expression, though this pattern was broken in a few instances. In general, the pattern for low expression consists of a low U/C ratio in the third base position of the codon for some amino acids, but a high U/C ratio in the third position for other amino acids. Perhaps due to the high %G+C content of the hemagglutinin gene a low U/C ratio existed for most amino acids. Overall, however, the codon usage followed the pattern for low expression more often than that for high expression. The usage of some codons which specify rate tRNA species in *E. coli* may also be evidence of a lower level of expression of the hemagglutinin gene. Alternatively, the same tRNA species may not be rate limiting in *P. gingivalis* but could explain the difficulty in expressing the cloned product in *E. coli*.

C. Characterization of the hag C gene and gene product. A third hemagglutinin gene, designated hag C was isolated from *Porphyromonas gingivalis* 381. The nucleotide sequence of the hag C gene is shown in SEQ ID NO. 5 and has a 1050 bp coding region. The derived amino acid sequence is shown in SEQ ID NO. 6.

The hag C gene was isolated in a similar manner as the hag B gene. Briefly, isolated *P. gingivalis* 381 chromosomal DNA was digested with HindIII and electrophoresed through a 0.8% agarose gel in Tris-acetate buffer. A band of agarose containing the fragements ranging from 4 to 20 kb was cut out of the gel and the DNA extracted using a phenol freeze/thaw procedure. The DNA was ligated to the dephosphorylated HindIII restricted pUC18 plasmid (Pharmacia LKB Biotechnology, Piscataway, N.J.) using the T4 DNA ligase (Promega Corp.) overnight at 16° C . The recombinant plasmids were transformed into *E. coli* DH5α (BRL) and plated on LB plates supplemented with ampicillin, IPTG and X-GAL. Colonies were picked on duplicate plates and grown aerobically at 37° C. overnight. The clones from one of the duplicated plants were transferred to positively charged nylon membranes (BM Corp.) and lysed according to the prodecure described by Sambrook et al The membranes were then left to dry for 30 minutes and baked at 120° C. for 30 minutes. The hybridization was carried out as described above; however, a 960 bp BamHI-PstI DNA fragment from hag B gene was used as a probe.

Recombinant plasmid DNA was prepared using the alkaline lysis method, modified as described. The cells were grown in LB broth supplemented with 50 μg/ml ampicillin.

The closed circular DNA was purified by equilibrium centrifugation in a continuous CsCl-ethidium bromide gradient. DNA further destined for sequence was additionally submitted to precipitation with polyethylene glycol.

Double stranded DNA sequencing was performed by the University of Florida Interdisciplinary Center for Biotechnology Research DNA Sequencing Core laboratory. Sequencing was accomplished by employing the Taq Dye Primer and Taq Dye Terminator cycle sequencing protocols (Applied Biosystems, Inc., Foster City, Calif.) using the fluorescent primers and dideoxynucleotides, respectively. The labeled extension products wre analyzed on an ABI373a DNA sequencer (Applied Biosystems, Inc.). The sequence was obtained for both strands of DNA using the appropriate subclones or synthetic oligonucleotides synthesized by the University of Florida DNA Synthesis Core Facility. the sequencing strategy was designed to sequence overlapping sites used in DNA subcloning. The sequence was analyzed with the Genetic Computer Group Sequence analysis software.

The 1851 bp HindIII-SstII DNA fragement comprising the hag C gene revealed an open reading frame (ORF) of 350 amino acids corresponding to a 39.3 kD protein with an isoelectric point of 8.36. The ATG start site, located at position 374 of the DNA, is preceded by putative $-10$ ($^{339}$TATTAT$^{334}$) and $-35$ ($^{314}$TTGCTG sequences which differ from the $E.$ $coli$ consensus promoter sequences TATAAT and TTGACA, by one and three nucleotides respectively. However, no match to consensus Shine-Dalgarno sequence could be found upstream the ATG codon. A nearly perfect dyad symmetry of 18 nucleotides can be noticed at the end of the hagC ORF and may represent a potential stem-loop structure used in transcription-termination.

A comparison between the hagB and hagC nucleotide sequences revealed that their ORFs are 99% homologous, but their upstream and downstream regions are only 39.5 and 34.6% homologous, respectively. It is worth noting that both genes encode a 350 a.a. protein which are 98.6% homologous. The hag B protein exhibits a deduced MW of 39.4 kD and pI of 8.98. The hag B gene possesses two sets of $-10$ and $-35$ sequences which are similiar to the consensus sequences found in $E.$ $coli$. Contrary to hag C however, a ribosome-binding site can be noted upstream the ATG initiation codon in position 363. Furthermore, four repeats of 42 bp each that are found in the promoter region of hag B are missing from the hag C gene. A potential transcription-termination stem-loop made by a nearly perfect 17 nucleotide long dyad symmetry can also be noted at the end of the hag B gene. No nucleotide sequence or protein exhibiting significant homology to the hag C gene or protein was found using the data bases GenBank, EMBL, or NBRF.

D. Characterization of the hag D gene and gene product. A fourth hemagglutinin gene, designated as hag D, was isolated from $P.$ $gingvalis$ 381 using standard procedures as described. The nucleotide sequence comprising the hag D gene is shown in SEQ ID NO. 7. The hag D ORF codes for a 1087 amino acid, 117 kDa protein with a pI of 4.5. The derived amino acid sequence encoded by the hag D gene is shown in SEQ ID NO. 8.

The $P.$ $gingivalis$ 381 cells were grown at 37° C. in Todd-Hewitt broth (THB) supplemented with 5 $\mu$g/ml hemin and 1 $\mu$g/ml menadione in an atmosphere of 10% $H_2$–5% $CO_2$–85% $N_2$. HindIII-restricted genomic DNA was then electrophoresed through TAE agarose gel (9%). The DNA was transferred to a nylon membrane by the capillary alkaline transfer method using 0.4M NaOH—0.6M NaC and labeled using the nonradioactive DNA labeling and detection kit (Genius, Boehringer Mannheim). The membrane was prehybridized for 2 hours at 42° C. in 5× SSC (0.75M NaCl, 0.085M sodium citrate (pH 7.0); blocking agent 0.5% (w/v); N-lauroylsarcosine (Na-salt), 0.1% (w/v); sodium dodecyl sulfate (SDS), 0.02% (w/v); formamide 50% (v/v)).

The EcoRI-PvuII DNA fragment from hag A was randomly primed by incorporation of digoxigenin-labeled dUTP. Hybridization was carried out overnight at 42° C. The membrane was washed twice with each of the following solutions: 2× SSC-0.1% (w/v) SDS at room temperature for 5 minutes, and 0.1× SSC—0.1% (w/v) SDS at 68° C. for 15 minutes. Detection was carried out using "LUMI-PHOS" 530 (Boehringer Mannheim), the enhancer for chemiluminescent detection of alkaline phosphatase, according to the manufacturer, and autoradiographed.

A genomic bank was created using HindIII-digested chromosomal DNA from $P.$ $gingivalis$ 381, as described above for hag C. Fragments ranging from 4.8 to 6.4 kb were cut out and the DNA was recovered using the phenol freeze/thaw procedure. The DNA was then ligated to the dephosphorylated HindIII restricted pUC18 (Pharmacia) using T4 DNA ligase overnight at 16° C.

Recombinant plasmids were transformed into $E.$ $coli$ DH5$\alpha$ (BRL) and plated on Luria-Bertani (LB)(10 g/l Bacto®Tryptone, 5 g/l yeast extract, 5 g/l NaCl, 15 g/l agar) plates supplemented with 50 $\mu$g/ml ampicillin. Colonies were picked, transferred to nylon membranes, and subjected to lysis in 10% (w/v) SDS, 3 minutes; 0.5N NaOH—1.5M NaCl, 5 minutes; 1.5M NaCl—0.5M Tris-Cl (pH 7.4), 5 minutes; and 2× SSC, 5 minutes. The membranes were then left to dry for 30 minutes and baked at 120° C. for 30 minutes. Prior to hybridization the membranes were washed in: 5× SSC, 0.5% SDS, 1 mM EDTA (pH 8.0) for 30 minutes at 50° C. Hybridization was then carried out as described above using a 1,228 bp HindIII-SmaI hag A DNA fragment as a probe.

Plasmid DNA was isolated and restriction mapping, was carried out according to procedures described.

Double-stranded DNA sequencing was performed by the University of Florida ICBR DNA Sequencing Core Laboratory. Sequencing was accomplished by employing the Taq Dye Primer and Taq Dye Terminator cycle sequencing protocols using the fluorescent primers and dideoxy nucleotides, respectively. The entire sequence was obtained for both strands of DNA using the appropriate subclones or synthetic oligonucleotides synthesized by the University of Florida DNA Synthesis Core Facility. The sequencing strategy was designed to sequence overlapping sites used in DNA subcloning.

The complete sequence was determined using the Genetic Computer Group Sequence analysis software and the inverse polymerase chain reaction (IPCR) method. For the IPCR procedure, 50–500 ng of $P.$ $gingivalis$ genomic DNA restricted with BamHI was circularized and self-ligated with T4 DNA ligase overnight at 16° C. The circularized genomic DNA was amplified by IPCR in a mixture containing: 160 mM each dNTs, 1.5 mM $MgCl_2$, 1× Buffer [1×=50 mM KCl, 10 mM Tris-HCl (pH 8.3)], 4×10$^{-4}$ mM of the primers APF 147 (5'-GGAATGGGAGATGGAACT-3') (SEQ ID NO. 11) and APF 148 (5'-GTAACCCGTATTGTCTCC-3') (SEQ ID NO. 12) and 5 U Taq I. The IPCR amplification was accomplished with the "PTC-100" Programmable Thermal Controller (MJ Research, Inc.) for 5 linked files as follows: (1) 30 minutes at 94° C. for 1 cycle after which the Taq I was added; (2) 1 minute at 94° C.; (3) 1 minute at 52° C.; (4) 5 minutes at 72° C., repeat steps 2,3, and 4, 34 more times; (5) 10 minutes at 72° C. The amplicon was gel purified and the DNA was extracted using agarase. The purified amplicon was sent to be sequenced using APF 147 (SEQ ID NO. 11) as the primer.

The recombinant plasmid comprising the hag D gene in *E. coli* expressed four proteins which were subjected to SDS-PAGE electrophorisis under denaturing conditions a doublet corresponding to proteins with Mr of 90 and 85.8 kDa, as well as an 80 kDa and a 20 kDa protein. Based on the intensity of the bands, the 80 kDa protein appeared to be the most strongly expressed. A comparison between hag D and hag A amino acid sequences revealed that they possess an overall homology of 73.8% composed of a central region with 90% homology flanked by regions sharing less than 60% homology. Hag D was also found to possess high homology (89.5%) to the prtP gene product isolated from the strain *P. gingivalis* W12. The N-terminus region of these two proteins was found to be more homologous (90%) than the C-terminus (72%). It is therefore possible that hag D and prtP gene products represent different alleles of the same gene which evolved, from a common ancestral strain and diverged. Both hag A and hag D transcripts, as determined by reverse PCR analysis, were detectable only in hemin-replete conditions as previously reported for hag C. These results show that hag A, hag C, and hag D might be coordinately regulated by hemin while hag B is differentially expressed.

E. Characterization of the prtP gene and gene product. A gene and polypeptide having homologous regions to those of the hag A, hag B, hag C, and hag D genes and gene products was isolated from *Porphyromonas gingivalis* W12. The *P. gingivalis* DNA insert in λFBP1 was 4.5 kb and was subcloned for sequencing. It contained a large open reading frame, which encodes approximately the carboxy-terminal two-thirds of the proteinase. The complete gene encoding porphypain was obtained using PCR and IPCR technology. The gene, which has a nucleotide sequence as shown in SEQ ID NO. 9, is designated prtP. The deduced amino acid sequence of the prtP gene is shown in SEQ ID NO. 10.

Genomic DNA from *Porphyromonas gingivalis* W12 was isolated using standard procedures, as described herein and was purified and disrupted by shearing. EcoRI linkers were ligated to the ends of *P. gingivalis* DNA fragments of appropriate sizes, and the fragments were cloned into the λgt11 vector. The λgt11 library was screened using polyclonal antibodies raised against a 120-kDa cysteine proteinase (porphypain), purified from *P. gingivalis* W12. Several clones were isolated that reacted strongly with the anti-proteinase antibody. One of the clones, λFBP1, reacted strongly with the antibody, and contained a protein which bound fibrinogen.

EXAMPLE 14

Construction of DNA Probes

DNA-DNA hybridization assays (DNA probes) are based on the fact that single-stranded DNA will reanneal only with a complementary strand of DNA whose sequence is homologous. More recently, DNA probes have been used as a means of detecting various infectious agents and some are now used routinely in clinical microbiology laboratories. The identification of DNA sequences of oral *Porphyromonas spp.* make it possible to create DNA probes for the identification of these species. Therefore, one application of the identification and isolation of genomic sequences which encode bacterial antigens is the use of the DNA fragments as DNA probes. In the current case, these probes may comprise the Porphyromonas clones identified herein, or fragments of these clones. Also, the DNA sequence shown in SEQ ID NOS. 1, 3, 5, 7, and 9, or fragments of those sequences, can be used to construct suitable probes.

Each recombinant plasmid is isolated and digested with whichever restriction enzyme was used to generate that particular genomic library. The digested plasmid DNA is then separated electrophoretically on an agarose gel as described earlier. The Porphyromonas DNA band containing the fragment is cut out of the gel and the DNA fragment is recovered by electro-elution employing centrifugal filtration of DNA fragments through a Durapore (Millipore) membrane inside a conical tip. This rapid and simple method recovers 70% of the DNA in a highly pure state.

The conical tip is assembled as follows: the conical portion of a 1.5 ml Eppendorf tube is cut off and a hole pierced in the bottom with a thin wire. A 4.5 cm$^2$ piece of Durapore (Millipore) membrane is wetted (d. $H_2O$) on a piece of parafilm, the filter square is then formed around a blunt-ended glass rod, and the filter is placed inside the conical bottom (cone). Excess filter is cut away, the filter tip is placed inside a 1.5 ml Eppendorf tube, and the filter is prewetted with 200 μl of elution buffer (0.1% SDS+50 mM Tris-HCl, pH 7.5). The gel slice is then transferred to the prepared conical tip. After centrifugation of the DNA preparation in a microcentrifuge (Eppendorf) for 10 minutes, the filtered aqueous phase containing the DNA is precipitated by the addition of 5M NaCl (to 1M) and two volumes of ethanol. After ethanol precipitation, the DNA fragment(s) is labeled non-radioactively, using a photo-activatable biotin tag as described by the supplier (Clontech Laboratories, Inc.).

For biotin labelling, the DNA fragment preparation is adjusted to a concentration of 1 mg/ml (TE) and is mixed with photo-activatable biotin (PAB) at a ratio of 1:3 (DNA:PAB) in a 1.5 ml Eppendorf tube. The tube is placed in an ice bath 10 cm below a 275 W (GE RSM) sunlamp and the DNA+PAB is irradiated for 15 minutes. The DNA solution is then mixed with an equal volume of 0.1M Tris-Cl (pH 9.0) and the volume adjusted to>100μl with $H_2$). The unincorporated PAB is extracted from the DNA by the addition of an equal volume of 2-butanol, vortexing, centrifuging briefly, and withdrawing the lower aqueous phase with a Pipetman. The extraction can be repeated to remove any traces of unbound PAB. 3M NaOAc (pH 5.6) is added to the DNA solution to a final concentration of 0.3M and the labeled DNA is precipitated by the addition of three volumes of ethanol.

After the sample is cooled at −70° C. for 15 minutes, the precipitated DNA is recovered by centrifugation for 10 minutes. The DNA pellet is dissolved in 10 mM Tris (pH 7.9) and 0.1 mM EDTA. The labeled probe DNA remains stable for one year if stored at −20° C.

A non-radioactive method of labeling the DNA probes may be desirable because: (1) the photoactivatable reactions are simple and rapid, (2) the sensitivity is as high as $^{32}$P-labeled probes, (3) the PAB-labeled probes have a long storage life, (4) these probes are relatively inexpensive, and (5) detection of bound probes is by simple calorimetric methods. The radioactive labeling of probes requires the use of $^{32}$p, which has a very short half-life (14 days) and is thus unstable and expensive. The use of radioactive probes would be limited because of cost, the dangers of radioactivity, strict requirements for disposal, and the need for licensing.

However, if for some reason the biotin-HRP method of labeling is unacceptable, the DNA fragments can be labeled with [δ P] 32 deoxy-CTP by standard nick translation methods as described by Maniatis et al. (1982, supra). Other labelling techniques which are well kown or accepted by ordinary skilled artisans can also be employed for visualization of the nucleic acid probes.

EXAMPLE 15

Determining the Specificity of the DNA Probes

The prepared DNA probes are screened for specificity against a battery of oral Porphyromonas species, other oral species, and other non-oral gram-negative bacteria.

Cultures of the test strains are grown in appropriate medium to a density of approximately $10^9$ cells per ml. The cells are centrifuged and suspended in 5.0 ml of distilled water. Sodium hydroxide is added to 0.5N and the cells are incubated at 90° C. for 20 to 30 minutes in order to lyse the cells and denature the DNA. The cell suspension is neutralized by the addition of 0.5N HCl diluted in 20× SSC and chilled on ice for 20 minutes. A volume of 0.5 ml (or less) of the suspension is diluted to 4.0 ml volume with 10× SSC and vacuum filtered in a manifold onto nitrocellulose paper (type HAWP, 0.45 µm, Millipore Corp.) which is prewetted with 10× SSC. After the filters are rinsed with 4.0 ml of 10× SSC, they are dried and heated at 85° C. for 3 hours in a vacuum oven (this fixes the chromosomal DNA onto the filter). After the filters are incubated for 2–3 hours at 42° C. with the prehybridization buffer (6× SSPE [1.08M NaCl, 0.06M NaH$_2$PO$_4$, 0.48M NaOH, 6.0 mM Na$_2$ EDTA, pH 7.0], 5× BFP [0.1% BSA, 0.1% Ficoll, and 0.1% polyvinyl pyrrolidine], 1% [w/v] glycine, 50% formamide, and 100 µg denatured salmon sperm DNA/ml), the prehybridization buffer is replaced with hybridization buffer containing 0.01 to 0.1 µg of labeled heat-denatured probe DNA in 5× SSPE, 1× BFP, 50% formamide, 100 µg salmon sperm 0.3% SDS, and 10% sulfate. Hybridization is accomplished by incubating the DNA mixtures for 12 hours at 42° C. The filters are then washed twice in 2× SSPE—0.2% SDA for 25 minutes at 60° C. in order to remove any unhybridized probe DNA The hybridized (bound) probe DNA can be detected by incubation of the filters for 30 minutes on 1M NaCl+0.1M Tris-HCl (pH 7.5)+2 mM MgCl$_2$+0.05% "TRITON" X-100+3% BSA and then for 25 minutes in 1 mg/ml streptavidin alkaline phosphate conjugate in the same buffer. Next, the filters are washed 3 times with 50–100 ml of buffer containing 1M NaCl, 0.1M Tris-HCl, pH 7.5, 2 mM MgCl$_2$, and 0.05% "TRITON" X-100. A fourth wash of buffer contains 0.1M NaCl and 0.3M sodium citrate, pH 7.0. The color is developed by the addition of 32 µl nitroblue tetrazolium, 16 µl 5-bromo-4-chloro-3-indosyl-phosphate in 5.0 ml of 0.1M NaCl+0.3M sodium citrate. After incubation in subdued light for 30 minutes, any spots which are visible indicate hybridization of probe DNA to target DNA.

If $^{32}$P-labeled probes are used the same hybridization conditions can be used (adding $10^6$ CPM of $^{32}$p probe) but instead of adding the streptavidin conjugate, the filters are dried for 1–2 hours at 70° C., and hybridization is detected by autoradiography. Alternatively, the filters can be cut into squares, placed into scintillation vials, and counted in scintillant.

Once probes are identified which are specific for either B. intermedius or P. gingivalis, or several Porphyromonas spp., they can be tested with known mixtures of the test bacteria grown on plates as follows: various mixtures of the test bacteria can be prepared with a known concentration of B. intermedius or P. gingivalis and spread on agar plates and incubated anaerobically as described earlier in this proposal. After the colonies have appeared (2–4 days), they are blotted onto nitrocellulose membranes, and the membranes processed for hybridization. If the DNA probe(s) is specific and sensitive, then only the P. gingivalis or B. intennedius colony blots should be positive. It is also possible that a probe may be found that is genus or group specific.

DNA probes for chromosomally-encoded genes require $10^5$ to $10^6$ bacteria per colony or dot blot in order to give a reliable positive result. This is comparable to 1 to 10 pg of DNA. Given this level of detection, a primary culturing step is desirable prior to blotting the colonies onto membrane filters and hybridization with the probe DNA.

EXAMPLE 16

Vaccines

Vaccines may be produced from the polypeptides expressed by cells which have been transformed with DNA fragments from Porphyromonas gingivalis. By introducing these peptides, along with a pharmacologically suitable vehicle, into the human or animal host, that host can be induced to generate immunological protection against P. gingivalis. The preparation of such a vaccine composition is within the skill of one trained in the medical and immunological sciences. Cells which can be used to produce recombinant peptides include, but are not limited to, bacteria, yeasts, insects, and eukaryotic cells.

EXAMPLE 17

Construction of an Oral Vaccine

It has been recognized that natural infection with enteric organisms produces the highest levels of antibodies and the longest lasting immunity to reinfection. The use of Salmonella as an attenuated vaccine carrier organism has several advantages. Salmonella spp. are capable of colonizing the Peyer's patches and gut lamina propria where they elicit a strong local IgA response in the intestine. The IgA response is also spread to other external secretions such as saliva by the seeding of these tissues with plasma cell precursors primed in the gut via the so called common mucosal immune system. These responses are important in preventing initial adhesion and colonization of mucosal surfaces—the initial step in the etiology of periodontal disease. In addition, live Salmonella elicits a humoral (serum) response of the IgM, IgG and IgA isotypes due to its invasive nature. Finally, infection with live organisms also stimulates a cell-mediated immune response—primarily T-cell mediated stimulation of macrophages—which is important in immunity since Salmonella can survive intracellularly within phagocytic cells. Several non-virulent mutants of Salmonella spp. have been developed. For example, an attenuated galE mutant of S. typhi (strain Ty21a) which lacks the enzyme UDP-galactose-4-epimerase has been developed.

Another approach to attenuation has been to use aromatic amino acid dependent (aro⁻) strains of Salmonella which are nonvirulent because they require metabolites not found in mammalian tissues, i.e., p-aminobenzoate and 2,3-dihydroxybenzoate. The strains are constructed using the aro:A554::Tn10 transposon, and, because it can cause deletion or deletion-inversion mutations, one can generate non-reverting mutants. These mutants synthesize a complete smooth LPS, are able to effectively colonize the Peyer's patches and gut, and are highly immunogenic. In mice of the Salmonella-susceptible line BALB/c, intraperitoneal injection of as few as $2 \times 10^5$ aro$^-$ S. typhimunum protected against an i.p. challenge of $5 \times 10^5$ virulent parent cells 30 days later (>25,000 i.p.LD$_{50}$). Oral immunization with $2 \times 10^8$ aro$^-$ cells protected mice against an oral challenge of $3 \times 10^7$ virulent organisms (ca. 100 oral LD$_{50}$).

Because live Salmonella is such an efficient stimulator of mucosal immunity it can be used as a carrier to deliver recombinant gene products cloned from other pathogens directly to the tissues (i.e., Peyer's patches) which most efficiently generate an immune response in the gut, and through the common mucosal immune system, to other distant secretory sites. At the same time a humoral immune response is stimulated which may further help prevent or abort invasion. Using cloned antigens in a Salmonella carrier system gives one the ability to target the immune response to important virulence antigens leading to a protective immune response.

Chromosomal DNA was isolated from P. gingivalis strain 381 by the following method: One to three liters of cells were pelleted by centrifugation and washed (on ice) in 1/50 volume of 1× SSC buffer (0.87% NaCl, 0.04% Na citrate) containing 27% sucrose and 10 mM EDTA. The cells were again pelleted and resuspended to $10^{10}$ cells/ml in the same buffer. Lysozyme (5 mg/mil in 1× SSC buffer) was added to 0.5 mg/ml, the cells were mixed thoroughly and incubated at 37° C. for 10 minutes. Nine volumes of 1× SSC containing 27% sucrose, 10 mM EDTA and 1.11% SDS (prewarmed to 39° C.) were added to the cells and incubated at 37° C. until cell lysis was complete (10–30 minutes). The lysed cells were mixed gently and incubated at 37° C. for 30 minutes. Proteinase K (Sigma, St. Louis, Mo.) was added to a final concentration of 1 mg/ml and the lysate was incubated at 37° C. for 4 hours. An equal volume of phenol-Tris (9:1 freshly distilled phenol:1M Tris-HCl, pH 7.5) was added to the Proteinase K-treated mixture and the mixture was agitated gently at room temperature for 30 minutes. The DNA mixture was then centrifuged in 150 ml Corex tubes at 3000 rpm. The top (phenol) layer was removed and discarded. The phenol extraction was repeated and the DNA (aqueous) layer was dialyzed extensively against 10 mM Tris-HCl, pH 8.0, 1 mM EDTA. Finally, the DNA was incubated with RNase at 37° C. for 1 hour.

Expression vectors which contain a promoter upstream from the cloning site were used to help insure that cloned DNA was expressed whether or not a structural gene was cloned with its own promoter. The expression plasmid pUC9 (2.7 kb) contains the origin of replication, ampicillin resistance gene, and lac gene of pBR 322. The lac HaeII fragment (lac gene) contains a polylinker region from M12mp9 which has multiple unique cloning sites in the gene that encodes for the peptide of β-galactosidase. Thus, recombinant vectors that contain an insert in any of the cloning sites generate white colonies on X-GAL plates since they are not able to degrade the lactose analog, X-GAL. Vectors without an insert degrade X-GAL and result in blue colonies on X-GAL plates since the gene is not interrupted by an insert. Other plasmid vectors are available and could be used. One such plasmid is pAD 230.

The chromosomal DNA and vector DNA were ligated with T4 DNA ligase at ratios of 2:1 and 5:1. The ligated DNA was phenol-chloroform (24:1 isoamyl alcohol) extracted, ethanol precipitated, washed, dried, and redissolved in TE. Early log-phase cells (OD=0.2 to 0.5) were washed with transformation buffer 1 (TFM 1, 10 mM Tris-Cl, pH 7.5, 0.15M NaCl). The cells were pelleted, resuspended, and incubated on ice for 45 minutes in TFM 2 (50 mM CaCl$_2$). After the cells are again pelleted, they are gently resuspended once more in TFM 2. A 0.2 ml volume of cells were added to 0.1 ml TFM 3 (10 mM Tris-HCl, pH 7.5, 50 mM CaCl$_2$, 10 mM MgSO$_4$.7H$_2$O) on ice. Varying amounts of DNA were added to the cells. The tubes were incubated on ice for 45 minutes, at which time the cells were heat shocked at 37° C. for 2 minutes. A 0.5 ml volume of LB broth was added per tube and the cells were incubated at 37° C. for 30 to 60 minutes to allow expression of antibiotic resistance. Finally, the cells were spread on plates of LB+antibiotic (50 μg /ml ampicillin) and X-GAL and incubated 24 to 48 hours at 37° C.

Any colonies which appeared on the LB+ampicillin+X-GAL plates after 24–36 hours of incubation were transformants which contained and expressed pUC9. A large number (80–90%) of these were white colonies which contain a plasmid with inserted P. gingivalis DNA. Once a transformant was identified which expressed P. gingivalis SHA adhesin, the protein was identified by Western blotting cell lysates of the transformant.

Because the initial cloning was done in E. coli, the recombinant plasmids may be modified by the E. coli modification system. These modified recombinant plasmids were used to transform strains of Salmonella. Initially, recombinant plasmids were passed into Salmonella typhimurium strain LB 5000, which is restriction$^-$ (is not able to restrict foreign DNA) but modification$^+$. This modifies the plasmid DNA according to the Salmonella system.

Recombinant P. gingivalis plasmids encoding for the Porphyromonas (SHA) adhesin can be isolated and purified as described above. The identity and purity of the preparation can be monitored by restriction analysis and agarose gel electrophoresis. Cells of Salmonella strain LB 5000 can be made competent and transformed with the recombinant plasmid as described above. Transformants can be selected by growth in the presence of ampicillin and are tested for the expression of the Porphyromonas antigen also by procedures described above.

The recombinant plasmid can be isolated from strain LB 5000 and the identity of the plasmid verified. The purified plasmid can be used to transform nonreverting nonvirulent mutants of various Salmonella spp. These strains include (but are not limited to)S. enteriditis (typhimunium) SL 3261 (WRAY his G46 aro A), SL 1479 (UCD his C527 aro A), SL 3237 (FIRN rps L120 aro A), and S. dublin SL 3261 (his 646 aro A). Transforrnants can be screened for resistance to ampicillin and assayed for expression of the Porphyromonas antigen by enzyme-linked immunosorbent assay as described above. In addition, SDS-PAGE and Western blotting can be done to confirm the presence of the antigen in the Salmonella transformants.

The P. gingivalis hemagglutinin protein was expressed in nonvirulent Salmonella typhimunum strain SL3261/CL7 and tested for activity as a competitive inhibitor of hemagglutination. The S. typhimurium cells were broken by sonic disruption, whole cells and debris removed by centrifugation and the supernatant adjusted to 40% saturation with NH$_4$SO$_3$. The supernatant was collected, dialyzed, and fractionated on a CM-Sephadex column using a 50–450 mM NaCl gradient. Fractions were evaluated via Western blot analysis for reactivity with absorbed sera directed against P. gingivalis. The peak fraction was found to inhibit hemagglutination of erythrocytes by whole P. gingivalis cells. This same material was analyzed for the N-terminal amino acid sequence and found to match the sequence predicted from the cloned gene.

The gene for the Porphyromonas antigen can also be transduced into the Salmonella carrier strains by P22 transduction. Transductants can be selected by growth in the presence of ampicillin and by the expression of the Porphyromonas antigen, as detected by immunoblotting using the monospecific or monoclonal antibody.

Additional carrier strains can be generated from other Salmonella serotypes. These strains can be derived from virulent strains by the introduction of mutations such as (auxotrophic) arc A or gal E. In addition, the "O" antigen may be altered or mutated to a rough LPS in strains already avirulent by $P_1$ transduction.

EXAMPLE 18

Monoclonal Antibodies

Appropriate mice can be immunized with antigens of, or cells expressing antigens of, *Porphyromonas gingivalis*. The antigens used for this immunization can be those which are identified and described in the previous examples. The techniques employed to accomplish this immunization procedure are familiar to those skilled in this art. The spleens can then be removed from the immunized mice and the cells therefrom fused to SP-2 myeloma cells using polyethylene glycol. The desired hybrid cells can then be selected by adding hypozanthine-aminopterin-thymidine to the medium. The surviving cells can then be tested for antibody production. The testing for antibody production can be accomplished using ELISA, immunoblot, and/or Western blot procedures as described in the previous examples.

The monoclonal antibodies produced by the procedure just described can be used to test for the presence of *P. gingivalis* antigens in a sample of biological fluid. The testing procedure involves contacting the biological fluid with a composition containing one or more of the monoclonal antibodies. If *P. gingivalis* antigens are present in the biological fluid, then a reaction will occur and this reaction can be detected and quantified by fluorescence or other means.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for the detection of the presence of *Porphyromonas gingivalis* DNA in human or animal tissue or fluid samples, said method comprising contacting said sample with a detectably labeled DNA probe wherein said probe comprises a detectable single-stranded DNA having a nucleotide sequence which specifically and selectively hybridizes with DNA of *Porphyromonas gingivalis*, said DNA probe comprising a nucleotide sequence selected. from the group consisting of SEQ ID NO.1, SEQ ID NO.3, SEQ ID NO.5, SEQ ID NO.7, and SEQ ID NO.9, whereby the presence of said DNA is indicative of a *Porphyromonas gingivalis* infection.

2. A kit for detecting infection by *Porphyromonas gingivalis*, wherein said kit comprises a detectably labeled *Porphyromonas gingivalis*-specific component, said component being selected from the group consisting of:(1) a nucleotide sequence comprising SEQ ID NO.1, SEQ ID NO.3, SEQ ID NO.5, SEQ ID NO.7, or SEQ ID NO.9; and (2) a polypeptide product of said nucleotide sequence comprising SEQ ID NO.2, SEQ ID NO.4, SEQ ID NO.6, SEQ ID NO.8, OR SEQ ID NO.10, and an antibody to said polypeptide product.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 4510 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 27..1518

( x i ) SEQUENCE DESCRIPTION: SEQ ID NO:1:

```
ATTAATCTTT AATACTTTCA AAAGGT ATG AGA AAA TTG AAT TCT TTA TTT TCG         53
                             Met Arg Lys Leu Asn Ser Leu Phe Ser
                              1               5

CTC GCC GTC CTA TTA TCC CTA TTG TGT TGG GGA CAG ACG GCT GCC GCA         101
Leu Ala Val Leu Leu Ser Leu Leu Cys Trp Gly Gln Thr Ala Ala Ala
 10              15                  20                  25

CAG GGA GGG CCG AAG ACT GCT CCT TCT GTG ACG CAC CAA GCG GTG CAG         149
Gln Gly Gly Pro Lys Thr Ala Pro Ser Val Thr His Gln Ala Val Gln
                 30                  35                  40

AAA GGT ATT CGA ACA TCC AAG GTT AAG GAT CTC CGA GAT CCG ATT CCT         197
Lys Gly Ile Arg Thr Ser Lys Val Lys Asp Leu Arg Asp Pro Ile Pro
             45                  50                  55

GCC GGT ATG GCA CGA ATT ATC TTG GAG GCT CAC GAT GTA TGG GAA GAC         245
Ala Gly Met Ala Arg Ile Ile Leu Glu Ala His Asp Val Trp Glu Asp
         60                  65                  70

GGC ACA GGC TAT CAA ATG CTT TGG GAT GCA GAT CAC AAT CAG TAC GGC         293
Gly Thr Gly Tyr Gln Met Leu Trp Asp Ala Asp His Asn Gln Tyr Gly
     75                  80                  85

GCA TCC ATT CCC GAA GAA TCT TTT TGG TTT GCC AAC GGA ACG ATC CCG         341
Ala Ser Ile Pro Glu Glu Ser Phe Trp Phe Ala Asn Gly Thr Ile Pro
```

-continued

| | | | | 90 | | | | | 95 | | | | | 100 | | | | | 105 | | |
|---|---|---|---|---|---|---|---|---|---|---|---|---|---|---|---|---|---|---|---|---|---|
| GCC | GGT | CTT | TAC | GAT | CCT | TTC | GAG | TAT | AAA | GTT | CCG | GTC | AAT | GCC | GAT | | | | | | 389 |
| Ala | Gly | Leu | Tyr | Asp | Pro | Phe | Glu | Tyr | Lys | Val | Pro | Val | Asn | Ala | Asp | | | | | | |
| | | | 110 | | | | | 115 | | | | | | 120 | | | | | | | |
| GCA | TCT | TTT | TCT | CCC | ACG | AAT | TTC | GTG | CTT | GAT | GGA | ACA | GCA | TCA | GCC | | | | | | 437 |
| Ala | Ser | Phe | Ser | Pro | Thr | Asn | Phe | Val | Leu | Asp | Gly | Thr | Ala | Ser | Ala | | | | | | |
| | | | 125 | | | | | 130 | | | | | | 135 | | | | | | | |
| GAT | ATT | CCT | GCC | GGC | ACT | TAT | GAC | TAT | GTA | ATC | ATT | AAC | CCC | AAT | CCT | | | | | | 485 |
| Asp | Ile | Pro | Ala | Gly | Thr | Tyr | Asp | Tyr | Val | Ile | Ile | Asn | Pro | Asn | Pro | | | | | | |
| | | 140 | | | | | 145 | | | | | | 150 | | | | | | | | |
| GGC | ATA | ATA | TAT | ATA | GTA | GGA | GAG | GGT | GTC | TCC | AAA | GGT | AAC | GAT | TAT | | | | | | 533 |
| Gly | Ile | Ile | Tyr | Ile | Val | Gly | Glu | Gly | Val | Ser | Lys | Gly | Asn | Asp | Tyr | | | | | | |
| | 155 | | | | | 160 | | | | | | 165 | | | | | | | | | |
| GTG | GTA | GAG | GCC | GGT | AAG | ACT | TAT | CAT | TTC | ACT | GTC | CAA | CGA | CAA | GGC | | | | | | 581 |
| Val | Val | Glu | Ala | Gly | Lys | Thr | Tyr | His | Phe | Thr | Val | Gln | Arg | Gln | Gly | | | | | | |
| 170 | | | | | 175 | | | | | 180 | | | | | 185 | | | | | | |
| CCC | GGC | GAT | GCT | GCG | TCC | GTT | GTA | GTG | ACC | GGA | GAA | GGT | GGC | AAT | GAA | | | | | | 629 |
| Pro | Gly | Asp | Ala | Ala | Ser | Val | Val | Val | Thr | Gly | Glu | Gly | Gly | Asn | Glu | | | | | | |
| | | | | 190 | | | | | 195 | | | | | 200 | | | | | | | |
| TTC | GCT | CCC | GTA | CAG | AAT | CTC | CAA | TGG | TCT | GTA | TCT | GGG | CAG | ACA | GTG | | | | | | 677 |
| Phe | Ala | Pro | Val | Gln | Asn | Leu | Gln | Trp | Ser | Val | Ser | Gly | Gln | Thr | Val | | | | | | |
| | | | 205 | | | | | 210 | | | | | 215 | | | | | | | | |
| ACC | CTC | ACT | TGG | CAA | GCC | CCC | GCA | TCC | GAC | AAA | CGG | ACT | TAT | GTG | TTG | | | | | | 725 |
| Thr | Leu | Thr | Trp | Gln | Ala | Pro | Ala | Ser | Asp | Lys | Arg | Thr | Tyr | Val | Leu | | | | | | |
| | | 220 | | | | | 225 | | | | | 230 | | | | | | | | | |
| AAC | GAA | AGC | TTC | GAT | ACG | CAA | ACG | CTT | CCT | AAC | GGC | TGG | ACA | ATG | ATC | | | | | | 773 |
| Asn | Glu | Ser | Phe | Asp | Thr | Gln | Thr | Leu | Pro | Asn | Gly | Trp | Thr | Met | Ile | | | | | | |
| | | 235 | | | | | 240 | | | | | 245 | | | | | | | | | |
| GAT | GCT | GAT | GGT | GAT | GGT | CAC | AAT | TGG | CTA | TCT | ACA | ATA | AAC | GTT | TAC | | | | | | 821 |
| Asp | Ala | Asp | Gly | Asp | Gly | His | Asn | Trp | Leu | Ser | Thr | Ile | Asn | Val | Tyr | | | | | | |
| 250 | | | | | 255 | | | | | 260 | | | | | 265 | | | | | | |
| AAC | ACT | GCT | ACT | CAT | ACA | GGT | GAC | GGT | GCT | ATG | TTT | AGC | AAA | TCA | TGG | | | | | | 869 |
| Asn | Thr | Ala | Thr | His | Thr | Gly | Asp | Gly | Ala | Met | Phe | Ser | Lys | Ser | Trp | | | | | | |
| | | | | 270 | | | | | 275 | | | | | 280 | | | | | | | |
| ACT | GCT | AGC | GGT | GGT | GCA | AAA | ATT | GAT | TTG | AGT | CCT | GAC | AAC | TAT | TTG | | | | | | 917 |
| Thr | Ala | Ser | Gly | Gly | Ala | Lys | Ile | Asp | Leu | Ser | Pro | Asp | Asn | Tyr | Leu | | | | | | |
| | | | 285 | | | | | 290 | | | | | 295 | | | | | | | | |
| GTA | ACT | CCA | AAG | GTT | ACG | GTT | CCT | GAG | AAT | GGT | AAA | CTT | TCT | TAT | TGG | | | | | | 965 |
| Val | Thr | Pro | Lys | Val | Thr | Val | Pro | Glu | Asn | Gly | Lys | Leu | Ser | Tyr | Trp | | | | | | |
| | | 300 | | | | | 305 | | | | | 310 | | | | | | | | | |
| GTT | TCA | TCT | CAA | GTG | CCT | TGG | ACT | AAT | GAG | CAT | TAT | GGA | GTG | TTC | TTG | | | | | | 1013 |
| Val | Ser | Ser | Gln | Val | Pro | Trp | Thr | Asn | Glu | His | Tyr | Gly | Val | Phe | Leu | | | | | | |
| | 315 | | | | | 320 | | | | | 325 | | | | | | | | | | |
| TCC | ACA | ACC | GGA | AAC | GAG | GCT | GCA | AAC | TTT | ACG | ATA | AAG | CTA | CTG | GAA | | | | | | 1061 |
| Ser | Thr | Thr | Gly | Asn | Glu | Ala | Ala | Asn | Phe | Thr | Ile | Lys | Leu | Leu | Glu | | | | | | |
| 330 | | | | | 335 | | | | | 340 | | | | | 345 | | | | | | |
| GAA | ACC | CTC | GGA | TCC | GAC | AAA | CCT | GCT | CCG | ATG | AAC | TTG | GTG | AAG | AGT | | | | | | 1109 |
| Glu | Thr | Leu | Gly | Ser | Asp | Lys | Pro | Ala | Pro | Met | Asn | Leu | Val | Lys | Ser | | | | | | |
| | | | | 350 | | | | | 355 | | | | | 360 | | | | | | | |
| GAA | GGA | GTA | AAG | CTT | CCT | GCA | CCT | TAT | CAG | GAA | AGA | ACC | ATC | GAT | CTC | | | | | | 1157 |
| Glu | Gly | Val | Lys | Leu | Pro | Ala | Pro | Tyr | Gln | Glu | Arg | Thr | Ile | Asp | Leu | | | | | | |
| | | | 365 | | | | | 370 | | | | | 375 | | | | | | | | |
| TCT | GCC | TAT | GCC | GGA | CAA | CAG | GTG | TAC | TTG | GCA | TTC | CGT | CAT | TTC | AAC | | | | | | 1205 |
| Ser | Ala | Tyr | Ala | Gly | Gln | Gln | Val | Tyr | Leu | Ala | Phe | Arg | His | Phe | Asn | | | | | | |
| | | 380 | | | | | 385 | | | | | 390 | | | | | | | | | |
| TCT | ACA | GGT | ATA | TTC | CGT | CTT | TAT | CTT | GAT | GAT | GTG | GCT | GTT | TCT | GGT | | | | | | 1253 |
| Ser | Thr | Gly | Ile | Phe | Arg | Leu | Tyr | Leu | Asp | Asp | Val | Ala | Val | Ser | Gly | | | | | | |
| | | 395 | | | | | 400 | | | | | 405 | | | | | | | | | |
| GAA | GGT | TCT | TCC | AAC | GAC | TAC | ACG | TAC | ACG | GTA | TAT | CGT | GAC | AAT | GTT | | | | | | 1301 |
| Glu | Gly | Ser | Ser | Asn | Asp | Tyr | Thr | Tyr | Thr | Val | Tyr | Arg | Asp | Asn | Val | | | | | | |

-continued

```
          410                    415                    420                    425
GTT ATT GCC CAG AAT CTC GCG GCA ACG ACA TTC AAT CAG GAA AAT GTA              1349
Val Ile Ala Gln Asn Leu Ala Ala Thr Thr Phe Asn Gln Glu Asn Val
                430                 435                 440

GCT CCC GGC CAG TAT AAC TAC TGT GTT GAA GTT AAG TAC ACA GCC GGC              1397
Ala Pro Gly Gln Tyr Asn Tyr Cys Val Glu Val Lys Tyr Thr Ala Gly
            445                 450                 455

GTA TCT CCG AAG GTA TGT AAA GAC GTT ACG GTA GAA GGA TCC AAC GAA              1445
Val Ser Pro Lys Val Cys Lys Asp Val Thr Val Glu Gly Ser Asn Glu
        460                 465                 470

TTT GCT CAT GTA CAG AAC CTG ACC GGT AGT GCA GTA GGT CAG AAA GTA              1493
Phe Ala His Val Gln Asn Leu Thr Gly Ser Ala Val Gly Gln Lys Val
    475                 480                 485

ACG CTT AAG TGG GAT GCA CCT AAT G GTACCCCGAA TCCGAATCCC                      1538
Thr Leu Lys Trp Asp Ala Pro Asn
490                 495

GGAACAACAA CACTTTCCGA ATCATTCGAA AATGGTATTC CTGCCTCATG GAAGACGATC            1598

GATGCAGACG GTGACGGCAA CAATTGGACG ACGACCCCTC CTCCCGGAGG CACCTCTTTT            1658

GCAGGTCACA ACAGTGCAAT CTGTGCCTCT TCGGCTTCTT ATATCAACTT TGAAGGTCCT            1718

CAGAACCCTG ATAACTATCT GGTTACACCG GAGCTATCTC TTCCTAACGG AGGAACGCTT            1778

ACTTTCTGGG TATGTGCACA AGATGCCAAT TATGCATCAG AGCACTATGC CGTGTACGCA            1838

TCTTCTACGG GTAACGACGC TTCCAACTTC GCCAACGCTT TGTTGGAAGA AGTGCTGACG            1898

GCCAAGACAG TTGTTACGGC ACCTGAAGCC ATTCGTGGCA CTCGTGTTCA GGGCACCTGG            1958

TATCAAAAGA CGGTACAGTT GCCTGCGGGT ACTAAGTATG TTGCTTTCCG TCACTTCGGC            2018

TGTACGGACT TCTTCTGGAT TAACCTTGAT GATGTTGAGA TCAAGGCCAA CGGCAAGCGC            2078

GCAGACTTCA CGGAAACGTT CGAGTCTTCT ACTCATGGAG AGGCACCGGC GGAATGGACT            2138

ACTATCGATG CCGATGGCGA TGGTCAGGGT TGGCTCTGTC TGTCTTCCGG ACAATTGGAC            2198

TGGCTGACAG CTCATGGCGG CACCAACGTA GTAGCCTCTT TCTCATGGAA TGGAATGGCT            2258

TTGAATCCTG ATAACTATCT CATCTCAAAG GATGTTACAG GCGCAACTAA GGTAAAGTAC            2318

TACTATGCAG TCAACGACGG TTTTCCCGGG GATCACTATG CGGTGATGAT CTCCAAGACG            2378

GGCACGAACG CCGGAGACTT CACGGTTGTT TTCGAAGAAA CGCCTAACGG AATAAATAAG            2438

GGCGGAGCAA GATTCGGTCT TTCCACGGAA GCCGATGGCG CCAAACCTCA AAGTGTATGG            2498

ATCGAGCGTA CGGTAGATTT GCCTGCGGGT ACTAAGTATG TTGCTTTCCG TCACTACAAT            2558

TGCTCGGATT TGAACTACAT TCTTTTGGAT GATATTCAGT TCACCATGGG TGGCAGCCCC            2618

ACCCCGACCG ATTATACCTA CACGGTGTAT CGTGACGGTA CGAAGATCAA GGAAGGTCTG            2678

ACCGAAACGA CCTTCGAAGA AGACGGTGTA GCTACGGGCA ACCATGAGTA TTGCGTGGAA            2738

GTGAAGTACA CAGCCGGCGT ATCTCCGAAA GAGTGTGTAA ACGTAACTGT TGATCCTGTG            2798

CAGTTCAATC CTGTACAGAA CCTGACCGGT AGTGCAGTCG GCCAGAAAGT AACGCTTAAG            2858

TGGGATGCAC CTAATGGTAC CCCGAATCCA AATCCAAATC CGAATCCGGG AACAACAACA            2918

CTTTCCGAAT CATTCGAAAA TGGTATTCCT GCCTCATGGA AGACGATCGA TGCAGACGGT            2978

GACGGCAACA ATTGGACGAC GACCCCTCCT CCCGGAGGCA CCTCTTTTGC AGGTCACAAC            3038

AGTGCGATCT GTGCCTCTTC GGCTTCTTAT ATCAACTTTG AAGGCCCTCA GAACCCTGAT            3098

AACTATCTGG TTACACCGGA GCTATCTCTT CCTAACGGAG GAACGCTTAC TTTCTGGGTA            3158

TGTGCACAAG ATGCCAATTA TGCATCAGAG CACTATGCCG TGTATGCATC TTCTACGGGT            3218

AACGACGCTT CCAACTTCGC CAACGCTTTG TTGGAAGAAG TGCTGACGGC CAAGACAGTT            3278
```

-continued

```
GTTACGGCAC CTGAAGCCAT TCGTGGCACT CGTGTTCAGG GCACCTGGTA TCAAAAGACG      3338
GTACAGTTGC CTGCGGGTAC TAAGTATGTT GCTTTCCGTC ACTTCGGCTG TACGGACTTC      3398
TTCTGGATCA ACCTTGATGA TGTTGAGATC AAGGCCAACG GCAAGCGCGC AGACTTCACG      3458
GAAACGTTCG AGTCTTCTAC TCATGGAGAG GCACCGGCGG AATGGACTAC TATCGATGCC      3518
GATGGCGATG GTCAGGGTTG GCTCTGTCTG TCTTCCGGAC AATTGGGCTG GCTGACAGCT      3578
CATGGCGGCA CCAACGTAGT AGCCTCTTTC TCATGGAATG GAATGGCTTT GAATCCTGAT      3638
AACTATCTCA TCTCAAAGGA TGTTACAGGC GCAACTAAGG TAAAGTACTA CTATGCAGTC      3698
AACGACGGTT TTCCCGGGGA TCACTATGCG GTGATGTTCT CCAAGACGGG CACGAACGCC      3758
GGAGACTTCA CGGTTGTTTT CGAAGAAACG CCTAACGGAA TAAATAAGGG CGGAGCAAGA      3818
TTCGGTCTTT CCACGGAAGC CGATGGCGCC AAACCTCAAA GTGTATGGTT CGAGCGTACG      3878
GTAGATTTGC CTGCGGGTAC TAAGTATGTT GCTTTCCGTC ACTACAATTG CTCGGATTTG      3938
AACTACATTC TTTTGGATGA TATTCAGTTC ACCATGGGTG GCAGCCCCAC CCCGACCGAT      3998
TATACCTACA CGGTGTATCG TGACGGTACG AAGATCAAGG AAGGTCTGAC CGAAACGACC      4058
TTCGAAGAAG ACGGTGTAGC TACGGGCAAC CATGAGTATT GCGTGGAAGT GAAGTACACA      4118
GCCGGCGTAT CTCCGAAAGA GTGTGTAAAC GTAACTGTTG ATCCTGTGCA GTTCAATCCT      4178
GTACAGAACC TGACCGGTAG TGCAGTCGGC CAGAAAGTAA CGCTTAAGTG GGATGCACCT      4238
AATGGTACCC CGAATCCAAA TCCAAATCCG AATCCGGGAA CAACAACACT TTCCGAATCA      4298
TTCGAAAATG GTATTCCTGC CTCATGGAAG ACGATCGATG CAGACGGTGA CGGCAACAAT      4358
TGGACGACGA CCCCTCCTCC CGGAGGCACC TCTTTTGCAG GTCACAACAG TGCGATCTGT      4418
GTCTCTTCGG CTTCTTATAT CAACTTTGAA GGCCCTCAGA ACCCTGATAA CTATCTGGTT      4478
ACACCGGAGC TATCTCTTCC TGGCGGATTA AT                                   4510
```

(2) INFORMATION FOR SEQ ID NO:2:

(i) SEQUENCE CHARACTERISTICS:
        (A) LENGTH: 497 amino acids
        (B) TYPE: amino acid
        (D) TOPOLOGY: linear (ii) MOLECULE TYPE: protein (xi) SEQUENCE DESCRIPTION: SEQ ID NO:2:

```
Met Arg Lys Leu Asn Ser Leu Phe Ser Leu Ala Val Leu Leu Ser Leu
 1               5                  10                  15

Leu Cys Trp Gly Gln Thr Ala Ala Gln Gly Gly Pro Lys Thr Ala
            20                  25                  30

Pro Ser Val Thr His Gln Ala Val Gln Lys Gly Ile Arg Thr Ser Lys
        35                  40                  45

Val Lys Asp Leu Arg Asp Pro Ile Pro Ala Gly Met Ala Arg Ile Ile
    50                  55                  60

Leu Glu Ala His Asp Val Trp Glu Asp Gly Thr Gly Tyr Gln Met Leu
65                  70                  75                  80

Trp Asp Ala Asp His Asn Gln Tyr Gly Ala Ser Ile Pro Glu Glu Ser
                85                  90                  95

Phe Trp Phe Ala Asn Gly Thr Ile Pro Ala Gly Leu Tyr Asp Pro Phe
            100                 105                 110

Glu Tyr Lys Val Pro Val Asn Ala Asp Ala Ser Phe Ser Pro Thr Asn
        115                 120                 125

Phe Val Leu Asp Gly Thr Ala Ser Ala Asp Ile Pro Ala Gly Thr Tyr
    130                 135                 140
```

```
Asp  Tyr  Val  Ile  Ile  Asn  Pro  Asn  Pro  Gly  Ile  Ile  Tyr  Ile  Val  Gly
145            150                     155                     160

Glu  Gly  Val  Ser  Lys  Gly  Asn  Asp  Tyr  Val  Glu  Ala  Gly  Lys  Thr
                165                     170                     175

Tyr  His  Phe  Thr  Val  Gln  Arg  Gln  Gly  Pro  Gly  Asp  Ala  Ala  Ser  Val
               180                185                     190

Val  Val  Thr  Gly  Glu  Gly  Gly  Asn  Glu  Phe  Ala  Pro  Val  Gln  Asn  Leu
          195                200                          205

Gln  Trp  Ser  Val  Ser  Gly  Gln  Thr  Val  Thr  Leu  Thr  Trp  Gln  Ala  Pro
     210                     215                     220

Ala  Ser  Asp  Lys  Arg  Thr  Tyr  Val  Leu  Asn  Glu  Ser  Phe  Asp  Thr  Gln
225                      230                235                          240

Thr  Leu  Pro  Asn  Gly  Trp  Thr  Met  Ile  Asp  Ala  Asp  Gly  Asp  Gly  His
               245                          250                255

Asn  Trp  Leu  Ser  Thr  Ile  Asn  Val  Tyr  Asn  Thr  Ala  Thr  His  Thr  Gly
               260                     265                     270

Asp  Gly  Ala  Met  Phe  Ser  Lys  Ser  Trp  Thr  Ala  Ser  Gly  Gly  Ala  Lys
               275                     280                285

Ile  Asp  Leu  Ser  Pro  Asp  Asn  Tyr  Leu  Val  Thr  Pro  Lys  Val  Thr  Val
     290                     295                     300

Pro  Glu  Asn  Gly  Lys  Leu  Ser  Tyr  Trp  Val  Ser  Ser  Gln  Val  Pro  Trp
305                           310                     315                     320

Thr  Asn  Glu  His  Tyr  Gly  Val  Phe  Leu  Ser  Thr  Thr  Gly  Asn  Glu  Ala
                325                          330                     335

Ala  Asn  Phe  Thr  Ile  Lys  Leu  Leu  Glu  Glu  Thr  Leu  Gly  Ser  Asp  Lys
               340                     345                     350

Pro  Ala  Pro  Met  Asn  Leu  Val  Lys  Ser  Glu  Gly  Val  Lys  Leu  Pro  Ala
               355                     360                     365

Pro  Tyr  Gln  Glu  Arg  Thr  Ile  Asp  Leu  Ser  Ala  Tyr  Ala  Gly  Gln  Gln
     370                     375                     380

Val  Tyr  Leu  Ala  Phe  Arg  His  Phe  Asn  Ser  Thr  Gly  Ile  Phe  Arg  Leu
385                      390                     395                          400

Tyr  Leu  Asp  Asp  Val  Ala  Val  Ser  Gly  Glu  Gly  Ser  Ser  Asn  Asp  Tyr
               405                     410                          415

Thr  Tyr  Thr  Val  Tyr  Arg  Asp  Asn  Val  Val  Ile  Ala  Gln  Asn  Leu  Ala
               420                     425                     430

Ala  Thr  Thr  Phe  Asn  Gln  Glu  Asn  Val  Ala  Pro  Gly  Gln  Tyr  Asn  Tyr
          435                     440                     445

Cys  Val  Glu  Val  Lys  Tyr  Thr  Ala  Gly  Val  Ser  Pro  Lys  Val  Cys  Lys
     450                     455                     460

Asp  Val  Thr  Val  Glu  Gly  Ser  Asn  Glu  Phe  Ala  His  Val  Gln  Asn  Leu
465                      470                     475                          480

Thr  Gly  Ser  Ala  Val  Gly  Gln  Lys  Val  Thr  Leu  Lys  Trp  Asp  Ala  Pro
                485                     490                     495

Asn
```

( 2 ) INFORMATION FOR SEQ ID NO:3:

( i ) SEQUENCE CHARACTERISTICS:
        ( A ) LENGTH: 1470 base pairs
        ( B ) TYPE: nucleic acid
        ( C ) STRANDEDNESS: single
        ( D ) TOPOLOGY: linear ( i i ) MOLECULE TYPE: DNA (genomic)

(iii) HYPOTHETICAL: NO (iv) ANTI-SENSE: NO (vi) ORIGINAL SOURCE:
 (A) ORGANISM: Porphyromonas gingivalis
 (B) STRAIN: FDC381

(vii) IMMEDIATE SOURCE:
 (A) LIBRARY: genomic
 (B) CLONE: ST7

(ix) FEATURE:
 (A) NAME/KEY: CDS
 (B) LOCATION: 310..1359

(xi) SEQUENCE DESCRIPTION: SEQ ID NO:3:

| | | | | | | | | | | | |
|---|---|---|---|---|---|---|---|---|---|---|---|
| GTTTCTTGCT | CCCTGCACGA | TGTAGGAAGC | CGTTGTCACG | TGACAATCAC | TCCGTGCATG | | | | | | 60 |
| ATGCAGGAAG | CCGTTGTCAC | GTGACAATCA | CTCCGTGCAC | GATGCAGGAA | GCTGTCGTCA | | | | | | 120 |
| CGTGACAATC | ACGTCCTGCA | CGATGCAGGA | AACGATTGTC | AGCCGACAAT | CGTTTCGCGC | | | | | | 180 |
| ACGGCTGTTT | TGACCTTTCG | TCGCCTGACA | ATGCTTATAT | AAAAGCTGTT | TCAGGGGCA | | | | | | 240 |
| GTGTCACTTG | ACACTGCTAC | CAATAACAGA | TTAATAATCA | ATCAAATACA | ACAAAAAAG | | | | | | 300 |

```
GAAAAACAA  ATG ACT GTA GAA AAT TTG CGT CTG CAG CGG CTC CAA AAT                348
           Met Thr Val Glu Asn Leu Arg Leu Gln Arg Leu Gln Asn
            1               5                      10

TTG GAG CAC TAC CGT TTT GCC AAG AAT GTG CTG ACG CTC TGT CGC ACG                396
Leu Glu His Tyr Arg Phe Ala Lys Asn Val Leu Thr Leu Cys Arg Thr
     15              20                  25

GCA AAT ATC GCT AAA CTG AAT CCC AAA CTG CCC GAG CTG GAA AAG GCT                444
Ala Asn Ile Ala Lys Leu Asn Pro Lys Leu Pro Glu Leu Glu Lys Ala
 30              35                  40                      45

ATC GAA ATG GAG GAT TTG GCT CTG AAT CCG CCC GTC GCG AAC GAG CTG                492
Ile Glu Met Glu Asp Leu Ala Leu Asn Pro Pro Val Ala Asn Glu Leu
                 50                  55                  60

ACG CCT CAG GTC ATA GCC CTC GAC GAG GAA CGC GAC AGA GCC TAT CAG                540
Thr Pro Gln Val Ile Ala Leu Asp Glu Glu Arg Asp Arg Ala Tyr Gln
                     65                  70                  75

GCG CTG ATG TCG CGC GTG CGT TCG TAT GCT TTC GAC GAG GAC AGC CAG                588
Ala Leu Met Ser Arg Val Arg Ser Tyr Ala Phe Asp Glu Asp Ser Gln
             80                  85                  90

CTG CGC AAC GCG GCA GCC AGA ATC GAA GAC GTG GCC GCT CGC TAC GGC                636
Leu Arg Asn Ala Ala Ala Arg Ile Glu Asp Val Ala Ala Arg Tyr Gly
     95                 100                 105

AAC GTG ATC CGA ATG AAC TAT GAC AAG GAG ACG GCC GCG ATA GAG AAT                684
Asn Val Ile Arg Met Asn Tyr Asp Lys Glu Thr Ala Ala Ile Glu Asn
110                 115                 120                 125

TTC CTC ACC GAT CTC AAG GGC GAG AAC ATT CGC CCC CTC GTA ACG AAA                732
Phe Leu Thr Asp Leu Lys Gly Glu Asn Ile Arg Pro Leu Val Thr Lys
                130                 135                 140

CTC GGC GTG ACG GCA CTC GTT GAC AGA CTG GAA AAG AAC AAT AAG GCC                780
Leu Gly Val Thr Ala Leu Val Asp Arg Leu Glu Lys Asn Asn Lys Ala
                145                 150                 155

TTC GCC GAC TTC TTC CTC CGC CGT CTG AGC ACC GAC CAA CGA GGC AAA                828
Phe Ala Asp Phe Phe Leu Arg Arg Leu Ser Thr Asp Gln Arg Gly Lys
         160                 165                 170

TAT GAC GTG AAG GCA CTC CGT GCC GAG ACC GAC CGC ACA TTG GTA GCC                876
Tyr Asp Val Lys Ala Leu Arg Ala Glu Thr Asp Arg Thr Leu Val Ala
     175                 180                 185

GTG GTG CGC CGC ATG GAC TCC ATC GAC GAC ATG GAG CCG AGC CCG GAG                924
Val Val Arg Arg Met Asp Ser Ile Asp Asp Met Glu Pro Ser Pro Glu
190                 195                 200                 205
```

| | | | | | | | | | | | | | | | | |
|---|---|---|---|---|---|---|---|---|---|---|---|---|---|---|---|---|
| ATC | CGT | GCG | CTC | ATC | GAG | CTC | TAC | AAC | CGA | CTC | GTG | GCC | AAT | CGC | CGC | 972 |
| Ile | Arg | Ala | Leu | Ile | Glu | Leu | Tyr | Asn | Arg | Leu | Val | Ala | Asn | Arg | Arg | |
| | | | | 210 | | | | 215 | | | | | | 220 | | |
| GCT | CTC | TTG | GCT | CGT | CGC | GCC | AGC | TAC | GGA | GAA | GCA | GCC | GTG | GAG | AAG | 1020 |
| Ala | Leu | Leu | Ala | Arg | Arg | Ala | Ser | Tyr | Gly | Glu | Ala | Ala | Val | Glu | Lys | |
| | | | | 225 | | | | 230 | | | | | | 235 | | |
| CGT | CGT | GCC | GAG | ATC | GCC | GAG | ATG | CTC | CGC | CCC | CTG | CTC | GCC | CGG | ATC | 1068 |
| Arg | Arg | Ala | Glu | Ile | Ala | Glu | Met | Leu | Arg | Pro | Leu | Leu | Ala | Arg | Ile | |
| | | | 240 | | | | 245 | | | | | 250 | | | | |
| GTG | GAG | GAG | AAG | AAG | ACG | GCC | GTC | TTT | GCC | GGT | CGC | ACC | CTC | GGC | ACG | 1116 |
| Val | Glu | Glu | Lys | Lys | Thr | Ala | Val | Phe | Ala | Gly | Arg | Thr | Leu | Gly | Thr | |
| | | 255 | | | | 260 | | | | | 265 | | | | | |
| GGC | AAG | AAC | CGC | CAC | TAT | CTC | ATC | ACA | TTC | GTA | GCC | GAG | AAC | GGC | GAC | 1164 |
| Gly | Lys | Asn | Arg | His | Tyr | Leu | Ile | Thr | Phe | Val | Ala | Glu | Asn | Gly | Asp | |
| 270 | | | | | 275 | | | | 280 | | | | | | 285 | |
| GAG | GAG | GAT | CGC | TGG | TAC | CGC | ATC | AAC | GGG | GAG | CAA | CTC | GTC | TAT | GTG | 1212 |
| Glu | Glu | Asp | Arg | Trp | Tyr | Arg | Ile | Asn | Gly | Glu | Gln | Leu | Val | Tyr | Val | |
| | | | | 290 | | | | 295 | | | | | | 300 | | |
| CCC | GAA | GAC | GAA | CTC | CCC | AAG | CCG | AAG | AAA | AAG | AAG | AAA | CCC | GCA | AGC | 1260 |
| Pro | Glu | Asp | Glu | Leu | Pro | Lys | Pro | Lys | Lys | Lys | Lys | Lys | Pro | Ala | Ser | |
| | | | 305 | | | | 310 | | | | | 315 | | | | |
| AGC | ACG | GAC | ACT | CCA | TCC | GAG | CCG | CCC | GTC | CTG | CCG | GAT | CCA | TCG | CAA | 1308 |
| Ser | Thr | Asp | Thr | Pro | Ser | Glu | Pro | Pro | Val | Leu | Pro | Asp | Pro | Ser | Gln | |
| | | 320 | | | | 325 | | | | | 330 | | | | | |
| GGA | GGC | AGC | AGT | AGC | GGC | GGT | GGC | GAG | CAA | GGC | TCT | ACC | GGC | GGC | GGA | 1356 |
| Gly | Gly | Ser | Ser | Ser | Gly | Gly | Gly | Glu | Gln | Gly | Ser | Thr | Gly | Gly | Gly | |
| | | 335 | | | | 340 | | | | | 345 | | | | | |
| CTC | TGATCCCCCC | GTGCCGTCCT | GCCGGCCGCA | GCAGCACAGG | CAACCGAGTA | | | | | | | | | | | 1409 |
| Leu | | | | | | | | | | | | | | | | |
| 350 | | | | | | | | | | | | | | | | |

TAAAAGACAA AGGGGCTGTG ACCAAATTCA TTTTTGGCAC AGCCCCTTGT ATATTCGAAA    1469

A                                                                   1470

( 2 ) INFORMATION FOR SEQ ID NO:4:

( i ) SEQUENCE CHARACTERISTICS:
        ( A ) LENGTH: 350 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met | Thr | Val | Glu | Asn | Leu | Arg | Leu | Gln | Arg | Leu | Gln | Asn | Leu | Glu | His |
| 1 | | | | 5 | | | | | 10 | | | | | 15 | |
| Tyr | Arg | Phe | Ala | Lys | Asn | Val | Leu | Thr | Leu | Cys | Arg | Thr | Ala | Asn | Ile |
| | | | 20 | | | | | 25 | | | | | 30 | | |
| Ala | Lys | Leu | Asn | Pro | Lys | Leu | Pro | Glu | Leu | Glu | Lys | Ala | Ile | Glu | Met |
| | | | | 35 | | | | 40 | | | | | 45 | | |
| Glu | Asp | Leu | Ala | Leu | Asn | Pro | Pro | Val | Ala | Asn | Glu | Leu | Thr | Pro | Gln |
| | | 50 | | | | | 55 | | | | | 60 | | | |
| Val | Ile | Ala | Leu | Asp | Glu | Glu | Arg | Asp | Arg | Ala | Tyr | Gln | Ala | Leu | Met |
| 65 | | | | | 70 | | | | | 75 | | | | | 80 |
| Ser | Arg | Val | Arg | Ser | Tyr | Ala | Phe | Asp | Glu | Asp | Ser | Gln | Leu | Arg | Asn |
| | | | | 85 | | | | | 90 | | | | | 95 | |
| Ala | Ala | Ala | Arg | Ile | Glu | Asp | Val | Ala | Ala | Arg | Tyr | Gly | Asn | Val | Ile |
| | | | | 100 | | | | | 105 | | | | | 110 | |
| Arg | Met | Asn | Tyr | Asp | Lys | Glu | Thr | Ala | Ala | Ile | Glu | Asn | Phe | Leu | Thr |
| | | | 115 | | | | | 120 | | | | | 125 | | |

| | | | | | | | | | | | | | | |
|---|---|---|---|---|---|---|---|---|---|---|---|---|---|---|
|Asp|Leu|Lys|Gly|Glu|Asn|Ile|Arg|Pro|Leu|Val|Thr|Lys|Leu|Gly|Val|
| | |130| | | |135| | | |140| | | | | |
|Thr|Ala|Leu|Val|Asp|Arg|Leu|Glu|Lys|Asn|Asn|Lys|Ala|Phe|Ala|Asp|
|145| | | | |150| | | |155| | | | | |160|
|Phe|Phe|Leu|Arg|Arg|Leu|Ser|Thr|Asp|Gln|Arg|Gly|Lys|Tyr|Asp|Val|
| | | | |165| | | | |170| | | | |175| |
|Lys|Ala|Leu|Arg|Ala|Glu|Thr|Asp|Arg|Thr|Leu|Val|Ala|Val|Val|Arg|
| | | |180| | | | |185| | | | |190| | |
|Arg|Met|Asp|Ser|Ile|Asp|Asp|Met|Glu|Pro|Ser|Pro|Glu|Ile|Arg|Ala|
| | |195| | | | |200| | | | |205| | | |
|Leu|Ile|Glu|Leu|Tyr|Asn|Arg|Leu|Val|Ala|Asn|Arg|Ala|Leu|Leu| |
| |210| | | | |215| | | | |220| | | | |
|Ala|Arg|Arg|Ala|Ser|Tyr|Gly|Glu|Ala|Ala|Val|Glu|Lys|Arg|Arg|Ala|
|225| | | | |230| | | | |235| | | | |240|
|Glu|Ile|Ala|Glu|Met|Leu|Arg|Pro|Leu|Leu|Ala|Arg|Ile|Val|Glu|Glu|
| | | | |245| | | | |250| | | | |255| |
|Lys|Lys|Thr|Ala|Val|Phe|Ala|Gly|Arg|Thr|Leu|Gly|Thr|Gly|Lys|Asn|
| | | |260| | | | |265| | | | |270| | |
|Arg|His|Tyr|Leu|Ile|Thr|Phe|Val|Ala|Glu|Asn|Gly|Asp|Glu|Glu|Asp|
| | |275| | | | |280| | | | |285| | | |
|Arg|Trp|Tyr|Arg|Ile|Asn|Gly|Glu|Gln|Leu|Val|Tyr|Val|Pro|Glu|Asp|
| |290| | | | |295| | | | |300| | | | |
|Glu|Leu|Pro|Lys|Pro|Lys|Lys|Lys|Lys|Pro|Ala|Ser|Ser|Thr|Asp| |
|305| | | |310| | | |315| | | | |320| | |
|Thr|Pro|Ser|Glu|Pro|Pro|Val|Leu|Pro|Asp|Pro|Ser|Gln|Gly|Gly|Ser|
| | | | |325| | | |330| | | | |335| | |
|Ser|Ser|Gly|Gly|Gly|Glu|Gln|Gly|Ser|Thr|Gly|Gly|Gly|Leu| | |
| | | |340| | | | |345| | | | |350| | |

( 2 ) INFORMATION FOR SEQ ID NO:5:

( i ) SEQUENCE CHARACTERISTICS:
        ( A ) LENGTH: 1841 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 374..1424

( x i ) SEQUENCE DESCRIPTION: SEQ ID NO:5:

```
AAGCTTGCAC CTACGACAAA AGATTTTTTC ATCTTACTAT ATTTTGGGAT TATATTTCTA        60

CACCTCCTTA TCCGGAATTT GGAAATGCGG GGCAAAAGTA GAAAAATTTT ATTTCCATCA       120

AAAAAAATCT TCAAATTTTT TTCACTTTGC GCATTCTGCA TATAAATGCT GCTACGTCGG       180

CAGATTATTC TGGTTAAAAA GTTATAGATG CAGCTCTTGG TTATAGTGTC CTAAGATCGC       240

TATGCAACCT GTAAGAAACG ATTGTAGGGT GTTTCTTGCT TCCTGCACGA ATGCAGGAGA       300

GCAGAAACGC CCGTTGCTGC TCCCGTCAAT ACACTAATTA TTATCGACTT AACCCCTTAA       360

TTCAAAAACT AAA ATG ACT GCA GAA ATT TTC TCG TTT TCC CGG CTC CAA         409
               Met Thr Ala Glu Ile Phe Ser Phe Ser Arg Leu Gln
                 1               5                  10

AAT TTG GAG CAC TAC CGT TTT GCC AAG AAT GTG CTG ACG CTC TGT CGC         457
Asn Leu Glu His Tyr Arg Phe Ala Lys Asn Val Leu Thr Leu Cys Arg
         15                  20                  25

ACG GCA AAT ATC GCT AAA CTG AAT CCC AAA CTG CCC GAG CTG AAA AAG         505
```

```
                Thr Ala Asn Ile Ala Lys Leu Asn Pro Lys Leu Pro Glu Leu Glu Lys
                    30                      35                      40

GCT ATC GAA ATG GAG GAT TTG GCT CTG AAT CCG CCC GTC GCG AAC GAG           553
Ala Ile Glu Met Glu Asp Leu Ala Leu Asn Pro Pro Val Ala Asn Glu
45                      50                      55                      60

CTG ACG CCT CAG GTC ATA GCC CTC GAC GAG GAA CGC GAC AGA GCC TAT           601
Leu Thr Pro Gln Val Ile Ala Leu Asp Glu Glu Arg Asp Arg Ala Tyr
                        65                      70                      75

CAG GCG CTG ATG TCG CGC GTG CGT TCG TAT GCT TTC GAC GAG GAC AGC           649
Gln Ala Leu Met Ser Arg Val Arg Ser Tyr Ala Phe Asp Glu Asp Ser
                80                      85                      90

CAG CTG CGC AAC GCG GCA GCC AGA ATC GAA GAC GTG GCC GCT CGC TAC           697
Gln Leu Arg Asn Ala Ala Ala Arg Ile Glu Asp Val Ala Ala Arg Tyr
        95                      100                     105

GGC AAC GTG ATC CGA ATG AAC TAT GAC AAG GAG ACG GCC GCG ATA GAG           745
Gly Asn Val Ile Arg Met Asn Tyr Asp Lys Glu Thr Ala Ala Ile Glu
    110                     115                     120

AAT TTC CTC ACC GAT CTC AAG GGC GAG AAC ATT CGC CCC CTC GTA ACG           793
Asn Phe Leu Thr Asp Leu Lys Gly Glu Asn Ile Arg Pro Leu Val Thr
125                     130                     135                     140

AAA CTC GGC GTG ACG GCA CTC GTT GAC AGA CTG GAA AAG AAC AAT AAG           841
Lys Leu Gly Val Thr Ala Leu Val Asp Arg Leu Glu Lys Asn Asn Lys
                        145                     150                     155

GCC TTC GCC GAC TTC TTC CTC CGC CGT CTG AGC ACC GAC CAA CGA GGC           889
Ala Phe Ala Asp Phe Phe Leu Arg Arg Leu Ser Thr Asp Gln Arg Gly
                160                     165                     170

AAA TAT GAC GTG AAG GCA CTC CGT GCC GAG ACC GAC CGC ACA TTG GTA           937
Lys Tyr Asp Val Lys Ala Leu Arg Ala Glu Thr Asp Arg Thr Leu Val
        175                     180                     185

GCC GTG GTG CGC CGC ATG GAC TCC ATC GAC GAC ATG GAG CCG AGC CCG           985
Ala Val Val Arg Arg Met Asp Ser Ile Asp Asp Met Glu Pro Ser Pro
    190                     195                     200

GAG ATC CGT GCG CTC ATC GAG CTC TAC AAC CGA CTC GTG GCC AAT CGC          1033
Glu Ile Arg Ala Leu Ile Glu Leu Tyr Asn Arg Leu Val Ala Asn Arg
205                     210                     215                     220

CGC GCT CTC TTG GCT CGT CGC GCC AGC TAC GGA GAA GCA GCC GTG GAG          1081
Arg Ala Leu Leu Ala Arg Arg Ala Ser Tyr Gly Glu Ala Ala Val Glu
                        225                     230                     235

AAG CGT CGT GCC GAG ATC GCC GAG ATG CTC CGC CCC CTG CTC GCC CGG          1129
Lys Arg Arg Ala Glu Ile Ala Glu Met Leu Arg Pro Leu Leu Ala Arg
                240                     245                     250

ATC GTG GAG GAG AAG AAG ACG GCC GTC TTT GCC GGT CGC ACC CTC GGC          1177
Ile Val Glu Glu Lys Lys Thr Ala Val Phe Ala Gly Arg Thr Leu Gly
        255                     260                     265

ACG GGC AAG AAC CGC CAC TAT CTC ATC ACA TTC GTA GCC GAG AAC GGC          1225
Thr Gly Lys Asn Arg His Tyr Leu Ile Thr Phe Val Ala Glu Asn Gly
    270                     275                     280

GAC GAG GAG GAT CGC TGG TAC CGC ATC AAC GGG GAG CAA CTC GTC TAT          1273
Asp Glu Glu Asp Arg Trp Tyr Arg Ile Asn Gly Glu Gln Leu Val Tyr
285                     290                     295                     300

GTG CCC GAA GAC GAA CTC CCC AAG CCG AAG AAA AAG AAG AAA CCC GCA          1321
Val Pro Glu Asp Glu Leu Pro Lys Pro Lys Lys Lys Lys Lys Pro Ala
                        305                     310                     315

AGC AGC ACG GAC ACT CCA TCC GAG CCG CCC GTC CTG CCG GAT CCA TCG          1369
Ser Ser Thr Asp Thr Pro Ser Glu Pro Pro Val Leu Pro Asp Pro Ser
                320                     325                     330

CAA GGA GGC AGC AGT AGC GGC GGT GGC GAG CAA GGC TCT ACC GGC GGC          1417
Gln Gly Gly Ser Ser Ser Gly Gly Gly Glu Gln Gly Ser Thr Gly Gly
        335                     340                     345

GGA CTC T GATCCGCACT CCCCCGTGCC GTCCTGTCGG CCGCAGCAGC ACAGGCAACC         1474
Gly Leu
```

Gly Leu
350

| GAGTATAAAA | GACAAAGGGG | CTGTGACCAA | ATTCATTTTT | GGCACAGCCC | CTTTCAGGTG | 1534 |
| CATAAGAATC | TATATTACGG | GAGAACAATC | CCTGTAAGAG | CAGTCACGAT | GCCGTTTTCC | 1594 |
| TCATATACAG | TAATCCGGAA | GACGTCTTCC | AGCAGATCGG | GATGTCTCAG | AACCCATGCT | 1654 |
| CCTTTTATGG | GCTGGGGTTT | TGGTTTGGCT | CTGTAAATTT | TTCCAAGGGA | TCTAGTTTTT | 1714 |
| AGCTCTCAAT | GGGCCAGATC | CCCCCTCAAG | TGCAATTCGA | GAGAGGATAA | AAGGGATAAT | 1774 |
| CCGTGAACGC | TCTGCGGTCT | ATCGGTAGCG | TACGGTCATG | AACAGGTGTG | TACGTGCCTG | 1834 |
| TCCGCGG | | | | | | 1841 |

( 2 ) INFORMATION FOR SEQ ID NO:6:

( i ) SEQUENCE CHARACTERISTICS:
        ( A ) LENGTH: 350 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Thr  Ala  Glu  Ile  Phe  Ser  Phe  Ser  Arg  Leu  Gln  Asn  Leu  Glu  His
 1                   5                        10                       15

Tyr  Arg  Phe  Ala  Lys  Asn  Val  Leu  Thr  Leu  Cys  Arg  Thr  Ala  Asn  Ile
               20                       25                       30

Ala  Lys  Leu  Asn  Pro  Lys  Leu  Pro  Glu  Leu  Glu  Lys  Ala  Ile  Glu  Met
          35                        40                       45

Glu  Asp  Leu  Ala  Leu  Asn  Pro  Pro  Val  Ala  Asn  Glu  Leu  Thr  Pro  Gln
     50                        55                       60

Val  Ile  Ala  Leu  Asp  Glu  Glu  Arg  Asp  Arg  Ala  Tyr  Gln  Ala  Leu  Met
65                       70                       75                       80

Ser  Arg  Val  Arg  Ser  Tyr  Ala  Phe  Asp  Asp  Ser  Gln  Leu  Arg  Asn
                    85                       90                       95

Ala  Ala  Ala  Arg  Ile  Glu  Asp  Val  Ala  Ala  Arg  Tyr  Gly  Asn  Val  Ile
               100                      105                      110

Arg  Met  Asn  Tyr  Asp  Lys  Glu  Thr  Ala  Ala  Ile  Glu  Asn  Phe  Leu  Thr
          115                      120                      125

Asp  Leu  Lys  Gly  Glu  Asn  Ile  Arg  Pro  Leu  Val  Thr  Lys  Leu  Gly  Val
     130                      135                      140

Thr  Ala  Leu  Val  Asp  Arg  Leu  Glu  Lys  Asn  Asn  Lys  Ala  Phe  Ala  Asp
145                      150                      155                      160

Phe  Phe  Leu  Arg  Arg  Leu  Ser  Thr  Asp  Gln  Arg  Gly  Lys  Tyr  Asp  Val
                    165                      170                      175

Lys  Ala  Leu  Arg  Ala  Glu  Thr  Asp  Arg  Thr  Leu  Val  Ala  Val  Val  Arg
               180                      185                      190

Arg  Met  Asp  Ser  Ile  Asp  Asp  Met  Glu  Pro  Ser  Pro  Glu  Ile  Arg  Ala
          195                      200                      205

Leu  Ile  Glu  Leu  Tyr  Asn  Arg  Leu  Val  Ala  Asn  Arg  Arg  Ala  Leu  Leu
     210                      215                      220

Ala  Arg  Arg  Ala  Ser  Tyr  Gly  Glu  Ala  Ala  Val  Glu  Lys  Arg  Arg  Ala
225                      230                      235                      240

Glu  Ile  Ala  Glu  Met  Leu  Arg  Pro  Leu  Leu  Ala  Arg  Ile  Val  Glu  Glu
               245                      250                      255

Lys  Lys  Thr  Ala  Val  Phe  Ala  Gly  Arg  Thr  Leu  Gly  Thr  Gly  Lys  Asn
          260                      265                      270
```

```
Arg  His  Tyr  Leu  Ile  Thr  Phe  Val  Ala  Glu  Asn  Gly  Asp  Glu  Glu  Asp
          275                      280                      285

Arg  Trp  Tyr  Arg  Ile  Asn  Gly  Glu  Gln  Leu  Val  Tyr  Val  Pro  Glu  Asp
     290                      295                      300

Glu  Leu  Pro  Lys  Pro  Lys  Lys  Lys  Lys  Pro  Ala  Ser  Ser  Thr  Asp
305                      310                      315                      320

Thr  Pro  Ser  Glu  Pro  Pro  Val  Leu  Pro  Asp  Pro  Ser  Gln  Gly  Gly  Ser
               325                      330                      335

Ser  Ser  Gly  Gly  Gly  Glu  Gln  Gly  Ser  Thr  Gly  Gly  Gly  Leu
               340                      345                      350
```

( 2 ) INFORMATION FOR SEQ ID NO:7:

( i ) SEQUENCE CHARACTERISTICS:
        ( A ) LENGTH: 4080 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 87..3347

( x i ) SEQUENCE DESCRIPTION: SEQ ID NO:7:

```
TCAAGAATCA  GGCCTTCTTA  ATAACCAATT  CAGGCCTTCC  TCCGGGTTCT  TACCGTAAAC         60

TAATTTACTA  AAAGTTGGAG  TTTTGT ATG GGA ACA GTT GTT GCT GAT CCC ACC            113
                              Met Gly Thr Val Val Ala Asp Pro Thr
                               1               5

GTT  GCT  GCG  CCT  GTG  AAA  ATG  GCT  AAA  CAG  ATA  GCC  GAA  AAT  GGT  AAT    161
Val  Ala  Ala  Pro  Val  Lys  Met  Ala  Lys  Gln  Ile  Ala  Glu  Asn  Gly  Asn
10                   15                        20                        25

TAT  GAT  GTA  GTG  ATG  ACT  CGC  TCT  AAC  TAT  CTT  CCT  GTG  ATC  AAC  CAA    209
Tyr  Asp  Val  Val  Met  Thr  Arg  Ser  Asn  Tyr  Leu  Pro  Val  Ile  Asn  Gln
                    30                        35                        40

ATT  CAG  GCA  GGA  GAG  CCT  AGC  CCC  TAC  CAG  CCT  GTT  AAC  AAC  TTG  ACT    257
Ile  Gln  Ala  Gly  Glu  Pro  Ser  Pro  Tyr  Gln  Pro  Val  Asn  Asn  Leu  Thr
               45                        50                        55

GCT  CCA  CCG  GAG  GGT  GAG  GAA  GTG  GCG  CTC  AAG  TGG  GAT  ACC  CCG  AGC    305
Ala  Pro  Pro  Glu  Gly  Glu  Glu  Val  Ala  Leu  Lys  Trp  Asp  Thr  Pro  Ser
          60                        65                        70

GCA  AAG  AAG  GCA  GAA  GCT  TCC  CGT  GAA  GTA  AAA  CGG  ATC  GGA  GAC  GGT    353
Ala  Lys  Lys  Ala  Glu  Ala  Ser  Arg  Glu  Val  Lys  Arg  Ile  Gly  Asp  Gly
     75                        80                        85

CTT  TTC  GTT  ACG  ATC  GAA  CCT  GCA  AAC  GAT  GTA  CGT  GCC  AAC  GAA  GCC    401
Leu  Phe  Val  Thr  Ile  Glu  Pro  Ala  Asn  Asp  Val  Arg  Ala  Asn  Glu  Ala
90                   95                        100                       105

AAG  GTT  GTG  CTC  GCA  GCA  GAC  AAC  GTA  TGG  GGA  GAC  AAT  ACG  GGT  TAC    449
Lys  Val  Val  Leu  Ala  Ala  Asp  Asn  Val  Trp  Gly  Asp  Asn  Thr  Gly  Tyr
                    110                       115                       120

CAG  TTC  TTG  TTG  GAT  GCC  GAT  CAC  AAT  ACA  TTC  GGA  AGT  GTC  ATT  CCG    497
Gln  Phe  Leu  Leu  Asp  Ala  Asp  His  Asn  Thr  Phe  Gly  Ser  Val  Ile  Pro
               125                       130                       135

GCA  ACC  GGT  CCT  CTC  TTT  ACC  GGA  ACA  GCT  TCT  TCC  AAT  CTT  TAC  AGT    545
Ala  Thr  Gly  Pro  Leu  Phe  Thr  Gly  Thr  Ala  Ser  Ser  Asn  Leu  Tyr  Ser
          140                       145                       150

GCG  AAC  TTC  GAG  TAT  TTG  ATC  CCG  GCC  AAT  GCC  GAT  CCT  GTT  GTT  ACT    593
Ala  Asn  Phe  Glu  Tyr  Leu  Ile  Pro  Ala  Asn  Ala  Asp  Pro  Val  Val  Thr
     155                       160                       165

ACA  CAG  AAT  ATT  ATC  GTT  ACA  GGA  CAG  GGT  GAA  GTT  GTA  ATC  CCC  GGT    641
Thr  Gln  Asn  Ile  Ile  Val  Thr  Gly  Gln  Gly  Glu  Val  Val  Ile  Pro  Gly
```

-continued

```
170                              175                              180                              185
GGT GTT TAC GAC TAT TGC ATT ACG AAC CCG GAA CCT GCA TCC GGA AAG                689
Gly Val Tyr Asp Tyr Cys Ile Thr Asn Pro Glu Pro Ala Ser Gly Lys
            190                     195                     200

ATG TGG ATC GCA GGA GAT GGA GAC AAC CAG CCT GCA CGT TAT GAC GAT                737
Met Trp Ile Ala Gly Asp Gly Asp Asn Gln Pro Ala Arg Tyr Asp Asp
            205                     210                     215

TTC ACA TTC GAA GCA GGC AAG AAG TAC ACC TTC ACG ATG CGT CGC GCC                785
Phe Thr Phe Glu Ala Gly Lys Lys Tyr Thr Phe Thr Met Arg Arg Ala
            220                     225                     230

GGA ATG GGA GAT GGA ACT GAT ATG GAA GTC GAA GAC GAT TCA CCT GCA                833
Gly Met Gly Asp Gly Thr Asp Met Glu Val Glu Asp Asp Ser Pro Ala
235                     240                     245

AGC TAT ACC TAT ACA GTC TAT CGT GAC GGC ACG AAG ATC AAG GAA GGT                881
Ser Tyr Thr Tyr Thr Val Tyr Arg Asp Gly Thr Lys Ile Lys Glu Gly
250                     255                     260                     265

CTG ACG GCT ACG ACA TTC GAA GAA GAC GGT GTA GCT GCA GGC AAT CAT                929
Leu Thr Ala Thr Thr Phe Glu Glu Asp Gly Val Ala Ala Gly Asn His
                        270                     275                     280

GAG TAT TGC GTG GAA GTT AAG TAC ACA GCC GGC GTA TCT CCG AAG GTA                977
Glu Tyr Cys Val Glu Val Lys Tyr Thr Ala Gly Val Ser Pro Lys Val
                285                     290                     295

TGT AAA GAC GTT ACG GTA GAA GGA TCC AAT GAA TTT GCT CCT GTA CAG               1025
Cys Lys Asp Val Thr Val Glu Gly Ser Asn Glu Phe Ala Pro Val Gln
            300                     305                     310

AAC CTG ACC GGT AGT GCA GTC GGC CAG AAA GTA ACG CTT AAG TGG GAT               1073
Asn Leu Thr Gly Ser Ala Val Gly Gln Lys Val Thr Leu Lys Trp Asp
            315                     320                     325

GCA CCT AAT GGT ACC CCA AAT CCG AAT CCG AAT CCG AAT CCG GGA ACA               1121
Ala Pro Asn Gly Thr Pro Asn Pro Asn Pro Asn Pro Asn Pro Gly Thr
330                     335                     340                     345

ACA ACA CTT TCC GAA TCA TTC GAA AAT GGT ATT CCT GCC TCA TGG AAG               1169
Thr Thr Leu Ser Glu Ser Phe Glu Asn Gly Ile Pro Ala Ser Trp Lys
                        350                     355                     360

ACG ATC GAT GCA GAC GGT GAC GGG CAT GGC TGG AAA CCT GGA AAT GCT               1217
Thr Ile Asp Ala Asp Gly Asp Gly His Gly Trp Lys Pro Gly Asn Ala
                365                     370                     375

CCC GGA ATC GCT GGC TAC AAT AGC AAT GGT TGT GTA TAT TCA GAG TCA               1265
Pro Gly Ile Ala Gly Tyr Asn Ser Asn Gly Cys Val Tyr Ser Glu Ser
            380                     385                     390

TTC GGT CTT GGT GGT ATA GGA GTT CTT ACC CCT GAC AAC TAT CTG ATA               1313
Phe Gly Leu Gly Gly Ile Gly Val Leu Thr Pro Asp Asn Tyr Leu Ile
            395                     400                     405

ACA CCG GCA TTG GAT TTG GCT AAC GGA GGT AAG TTG ACT TTC TGG GTA               1361
Thr Pro Ala Leu Asp Leu Ala Asn Gly Gly Lys Leu Thr Phe Trp Val
410                     415                     420                     425

TGC GCA CAG GAT GCT AAT TAT GCA TCC GAG CAC TAT GCG GTG TAT GCA               1409
Cys Ala Gln Asp Ala Asn Tyr Ala Ser Glu His Tyr Ala Val Tyr Ala
                430                     435                     440

TCT TCG ACC GGT AAC GAT GCA TCC AAC TTC ACG AAT GCT TTG TTG GAA               1457
Ser Ser Thr Gly Asn Asp Ala Ser Asn Phe Thr Asn Ala Leu Leu Glu
                        445                     450                     455

GAG ACG ATT ACG GCA AAA GGT GTT CGC TCG CCG GAA GCT ATT CGT GGT               1505
Glu Thr Ile Thr Ala Lys Gly Val Arg Ser Pro Glu Ala Ile Arg Gly
            460                     465                     470

CGT ATA CAG GGT ACT TGG CGC CAG AAG ACG GTA GAC CTT CCC GCA GGT               1553
Arg Ile Gln Gly Thr Trp Arg Gln Lys Thr Val Asp Leu Pro Ala Gly
            475                     480                     485

ACG AAA TAT GTT GCT TTC CGT CAC TTC CAA AGC ACG GAT ATG TTC TAC               1601
Thr Lys Tyr Val Ala Phe Arg His Phe Gln Ser Thr Asp Met Phe Tyr
```

-continued

| 490 | | | | | 495 | | | | | 500 | | | | | 505 | | | |
|---|---|---|---|---|---|---|---|---|---|---|---|---|---|---|---|---|---|---|
| ATC | GAC | CTT | GAT | GAG | GTT | GAG | ATC | AAG | GCC | AAT | GGC | AAG | CGC | GCA | GAC | | | 1649 |
| Ile | Asp | Leu | Asp | Glu | Val | Glu | Ile | Lys | Ala | Asn | Gly | Lys | Arg | Ala | Asp | | | |
| | | | | 510 | | | | 515 | | | | | 520 | | | | | |
| TTC | ACG | GAA | ACG | TTC | GAG | TCT | TCT | ACT | CAT | GGA | GAG | GCA | CCA | GCG | GAA | | | 1697 |
| Phe | Thr | Glu | Thr | Phe | Glu | Ser | Ser | Thr | His | Gly | Glu | Ala | Pro | Ala | Glu | | | |
| | | | 525 | | | | | 530 | | | | 535 | | | | | | |
| TGG | ACT | ACT | ATC | GAT | GCC | GAT | GGC | GAT | GGT | CAG | GAT | TGG | CTC | TGT | CTG | | | 1745 |
| Trp | Thr | Thr | Ile | Asp | Ala | Asp | Gly | Asp | Gly | Gln | Asp | Trp | Leu | Cys | Leu | | | |
| | | 540 | | | | | 545 | | | | | 550 | | | | | | |
| TCT | TCC | GGA | CAA | TTG | GAC | TGG | CTG | ACA | GCT | CAT | GGC | GGC | ACC | AAC | GTA | | | 1793 |
| Ser | Ser | Gly | Gln | Leu | Asp | Trp | Leu | Thr | Ala | His | Gly | Gly | Thr | Asn | Val | | | |
| | 555 | | | | | 560 | | | | | 565 | | | | | | | |
| GTA | GCC | TCT | TTC | TCA | TGG | AAT | GGA | ATG | GCT | TTG | AAT | CCT | GAT | AAC | TAT | | | 1841 |
| Val | Ala | Ser | Phe | Ser | Trp | Asn | Gly | Met | Ala | Leu | Asn | Pro | Asp | Asn | Tyr | | | |
| 570 | | | | | 575 | | | | | 580 | | | | | 585 | | | |
| CTC | ATC | TCA | AAG | GAT | GTT | ACA | GGC | GCA | ACG | AAG | GTA | AAG | TAC | TAC | TAT | | | 1889 |
| Leu | Ile | Ser | Lys | Asp | Val | Thr | Gly | Ala | Thr | Lys | Val | Lys | Tyr | Tyr | Tyr | | | |
| | | | | 590 | | | | 595 | | | | | 600 | | | | | |
| GCA | GTC | AAC | GAC | GGT | TTT | CCC | GGG | GAT | CAC | TAT | GCG | GTG | ATG | ATC | TCC | | | 1937 |
| Ala | Val | Asn | Asp | Gly | Phe | Pro | Gly | Asp | His | Tyr | Ala | Val | Met | Ile | Ser | | | |
| | | | 605 | | | | | 610 | | | | 615 | | | | | | |
| AAG | ACG | GGC | ACG | AAC | GCC | GGA | GAC | TTC | ACG | GTT | GTT | TTC | GAA | GAA | ACG | | | 1985 |
| Lys | Thr | Gly | Thr | Asn | Ala | Gly | Asp | Phe | Thr | Val | Val | Phe | Glu | Glu | Thr | | | |
| | | 620 | | | | | 625 | | | | | 630 | | | | | | |
| CCT | AAC | GGA | ATA | AAT | AAG | GGC | GGA | GCA | AGA | TTC | GGT | CTT | TCC | ACG | GAA | | | 2033 |
| Pro | Asn | Gly | Ile | Asn | Lys | Gly | Gly | Ala | Arg | Phe | Gly | Leu | Ser | Thr | Glu | | | |
| | | 635 | | | | | 640 | | | | | 645 | | | | | | |
| GCC | AAT | GGC | GCC | AAA | CCT | CAA | AGT | GTA | TGG | ATC | GAG | CGT | ACG | GTA | GAT | | | 2081 |
| Ala | Asn | Gly | Ala | Lys | Pro | Gln | Ser | Val | Trp | Ile | Glu | Arg | Thr | Val | Asp | | | |
| 650 | | | | | 655 | | | | | 660 | | | | | 665 | | | |
| TTG | CCT | GCG | GGC | ACG | AAG | TAT | GTT | GCT | TTC | CGT | CAC | TAC | AAT | TGC | TCG | | | 2129 |
| Leu | Pro | Ala | Gly | Thr | Lys | Tyr | Val | Ala | Phe | Arg | His | Tyr | Asn | Cys | Ser | | | |
| | | | | 670 | | | | 675 | | | | | 680 | | | | | |
| GAT | TTG | GAC | TAC | ATT | CTT | TTG | GAT | GAT | ATT | CAG | TTC | ACC | ATG | GGT | GGC | | | 2177 |
| Asp | Leu | Asp | Tyr | Ile | Leu | Leu | Asp | Asp | Ile | Gln | Phe | Thr | Met | Gly | Gly | | | |
| | | | 685 | | | | | 690 | | | | 695 | | | | | | |
| AGC | CCC | ACC | CCG | ACC | GAT | TAT | ACC | TAC | ACG | GTA | TAT | CGT | GAT | GGT | ACG | | | 2225 |
| Ser | Pro | Thr | Pro | Thr | Asp | Tyr | Thr | Tyr | Thr | Val | Tyr | Arg | Asp | Gly | Thr | | | |
| | | 700 | | | | | 705 | | | | | 710 | | | | | | |
| AAG | ATC | AAG | GAA | GGT | CTG | ACC | GAA | ACG | ACC | TTC | GAA | GAA | GAC | GGC | GTA | | | 2273 |
| Lys | Ile | Lys | Glu | Gly | Leu | Thr | Glu | Thr | Thr | Phe | Glu | Glu | Asp | Gly | Val | | | |
| | 715 | | | | | 720 | | | | | 725 | | | | | | | |
| GCT | ACG | GGC | AAT | CAT | GAG | TAT | TGC | GTG | GAA | GTG | AAG | TAC | ACA | GCC | GGC | | | 2321 |
| Ala | Thr | Gly | Asn | His | Glu | Tyr | Cys | Val | Glu | Val | Lys | Tyr | Thr | Ala | Gly | | | |
| 730 | | | | | 735 | | | | | 740 | | | | | 745 | | | |
| GTA | TCT | CCG | AAG | GTG | TGT | GTA | AAC | GTA | ACT | ATT | AAT | CCG | ACT | CAG | TTC | | | 2369 |
| Val | Ser | Pro | Lys | Val | Cys | Val | Asn | Val | Thr | Ile | Asn | Pro | Thr | Gln | Phe | | | |
| | | | | 750 | | | | 755 | | | | | 760 | | | | | |
| AAT | CCT | GTA | AAG | AAC | CTG | AAG | GCA | CAA | CCG | GAT | GGC | GGC | GAC | GTG | GTT | | | 2417 |
| Asn | Pro | Val | Lys | Asn | Leu | Lys | Ala | Gln | Pro | Asp | Gly | Gly | Asp | Val | Val | | | |
| | | | 765 | | | | | 770 | | | | 775 | | | | | | |
| CTC | AAG | TGG | GAA | GCC | CCG | AGT | GGC | AAA | CGA | GGA | GAA | CTG | CTT | AAT | GAA | | | 2465 |
| Leu | Lys | Trp | Glu | Ala | Pro | Ser | Gly | Lys | Arg | Gly | Glu | Leu | Leu | Asn | Glu | | | |
| | | 780 | | | | | 785 | | | | | 790 | | | | | | |
| GAT | TTT | GAA | GGA | GAC | GCT | ATT | CCC | ACA | GGG | TGG | ACA | GCA | TTG | GAT | GCC | | | 2513 |
| Asp | Phe | Glu | Gly | Asp | Ala | Ile | Pro | Thr | Gly | Trp | Thr | Ala | Leu | Asp | Ala | | | |
| | 795 | | | | | 800 | | | | | 805 | | | | | | | |
| GAT | GGT | GAC | GGT | AAT | AAC | TGG | GAT | ATC | ACG | CTC | AAT | GAA | TTT | ACG | CGA | | | 2561 |
| Asp | Gly | Asp | Gly | Asn | Asn | Trp | Asp | Ile | Thr | Leu | Asn | Glu | Phe | Thr | Arg | | | |

```
           810                     815                     820                     825
GGA GAG CGT CAT GTT CTT TCA CCT TTA CGC GCC AGC AAC GTA GCC ATA           2609
Gly Glu Arg His Val Leu Ser Pro Leu Arg Ala Ser Asn Val Ala Ile
                    830                     835                     840

TCC TAT TCT TCT TTA CTT CAG GGT CAA GAA TAT TTG CCT CTC ACG CCG           2657
Ser Tyr Ser Ser Leu Leu Gln Gly Gln Glu Tyr Leu Pro Leu Thr Pro
                845                     850                     855

AAC AAC TTT CTG ATC ACT CCG AAG GTT GAA GGA GCA AAG AAG ATT ACT           2705
Asn Asn Phe Leu Ile Thr Pro Lys Val Glu Gly Ala Lys Lys Ile Thr
            860                     865                     870

TAT AAG GTG GGT TCA CCG GGT CTT CCT CAA TGG AGT CAT GAT CAT TAT           2753
Tyr Lys Val Gly Ser Pro Gly Leu Pro Gln Trp Ser His Asp His Tyr
        875                     880                     885

GCA CTC TGT ATC TCC AAG AGC GGA ACG GCT GCA GCC GAC TTC GAA GTA           2801
Ala Leu Cys Ile Ser Lys Ser Gly Thr Ala Ala Ala Asp Phe Glu Val
890                     895                     900                     905

ATC TTT GAA GAA ACG ATG ACC TAC ACT CAA GGA GGA GCC AAC TTG ACA           2849
Ile Phe Glu Glu Thr Met Thr Tyr Thr Gln Gly Gly Ala Asn Leu Thr
                    910                     915                     920

AGA GAA AAA GAC CTC CCT GCC GGC ACG AAA TAT GTC GCT TTC CGT CAT           2897
Arg Glu Lys Asp Leu Pro Ala Gly Thr Lys Tyr Val Ala Phe Arg His
                925                     930                     935

TAC AAT TGC ACG GAT GTT CTG GGC ATA ATG ATT GAC GAT GTA GTG ATA           2945
Tyr Asn Cys Thr Asp Val Leu Gly Ile Met Ile Asp Asp Val Val Ile
            940                     945                     950

ACA GGT GAA GGC GAA GGT CCC AGT TAC ACC TAC ACG GTG TAT CGT GAC           2993
Thr Gly Glu Gly Glu Gly Pro Ser Tyr Thr Tyr Thr Val Tyr Arg Asp
        955                     960                     965

GGC ACG AAG ATC CAG GAA GGT CTG ACC GAA ACG ACC TAC CGC GAT GCA           3041
Gly Thr Lys Ile Gln Glu Gly Leu Thr Glu Thr Thr Tyr Arg Asp Ala
970                     975                     980                     985

GGA ATG AGT GCA CAA TCT CAT GAG TAT TGC GTA GAG GTT AAG TAC GCA           3089
Gly Met Ser Ala Gln Ser His Glu Tyr Cys Val Glu Val Lys Tyr Ala
                    990                     995                     1000

GCC GGC GTA TCT CCG AAG GTT TGT GTG GAT TAT ATT CCT GAT GGA GTG           3137
Ala Gly Val Ser Pro Lys Val Cys Val Asp Tyr Ile Pro Asp Gly Val
                1005                    1010                    1015

GCA GAC GTA ACT GCT CAG AAG CCT TAC ACG CTG ACG GTT GTA GGA AAG           3185
Ala Asp Val Thr Ala Gln Lys Pro Tyr Thr Leu Thr Val Val Gly Lys
            1020                    1025                    1030

ACT ATC ACG GTA ACT TGC CAA GGC GAA GCT ATG ATC TAC GAC ATG AAC           3233
Thr Ile Thr Val Thr Cys Gln Gly Glu Ala Met Ile Tyr Asp Met Asn
        1035                    1040                    1045

GGT CGT CGT CTG GCA GCG GGT CGC AAC ACG GTT GTT TAC ACG GCT CAG           3281
Gly Arg Arg Leu Ala Ala Gly Arg Asn Thr Val Val Tyr Thr Ala Gln
1050                    1055                    1060                    1065

GGC GGC TAC TAT GCA GTC ATG GTT GTC GTT GAC GGC AAG TCT TAC GTA           3329
Gly Gly Tyr Tyr Ala Val Met Val Val Val Asp Gly Lys Ser Tyr Val
                    1070                    1075                    1080

GAG AAA CTC GCT ATC AAG TAATTCTGTC TTGGACTCGG AGACTTTGTG                  3377
Glu Lys Leu Ala Ile Lys
                    1085

CAGACACTTT TAATATAGGT CTGTAATTGT CTCAGAGTAT GAATCGGTCG CCCGACTTCC         3437

TTAAAAGGAG GTCGGGCGAC TTCGTTTTTA TTATTGCTGT CTGGTAAACT TGTCAAGAGG         3497

AGACCTTTGA AAAATGGGGC GGTCAATAAT TTTCGGTCTA TGGGTCAAAT TGCAGGCTAC         3557

TGTTTTAGGT GTATGTTGGG CTATCTTCCT ATCTTTAAGA GACCTTTGAA AAATAAGGAG         3617

ATGGAGGGAA GAGGAGTTCT TGGCATAAAA GGAGCGAGTG AAAGGGGTGG CAGTAAGGAG         3677
```

-continued

| | | | | | |
|---|---|---|---|---|---|
| TGAAAGTAGT | TGTAAATCCC | CCCTTTGAGG | AGCTACTTGT | ACGAGCTCCT | CAAGGGTGGT | 3737 |
| TATGCCTTAT | CCTACGGATG | AGGACATAAT | TATCCCCGGC | GTTCTGTATA | AATTAAAGGC | 3797 |
| GATGCTTTCA | AGAATGTTTT | GAGTATGGGT | CTTGGCAAGT | CCCCGGTATC | GACATGTCCG | 3857 |
| CCATGAAACC | ACCGGCGAAT | ACTGCCAAAG | GTGCGTTCGA | TGGTGCTCCG | TATCGGACTG | 3917 |
| ATTGCTTTGT | TTCGTTGCTT | CTCTTCCTCG | GTCAATGCCC | TGTTGCGTTG | TGCCTTGTGC | 3977 |
| ATAATGCCGT | CTTGAAGGTG | ATGGGTTTGC | AGGTAGGAAC | GATTTTCCCC | GCAAGCATAT | 4037 |
| CCTTTGTCCG | CCAAGACGGC | TGTACCTTGA | GGTATGTTTG | CAC | | 4080 |

( 2 ) INFORMATION FOR SEQ ID NO:8:

( i ) SEQUENCE CHARACTERISTICS:
        ( A ) LENGTH: 1087 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Gly Thr Val Val Ala Asp Pro Thr Val Ala Ala Pro Val Lys Met
 1               5                  10                  15

Ala Lys Gln Ile Ala Glu Asn Gly Asn Tyr Asp Val Val Met Thr Arg
                20                  25                  30

Ser Asn Tyr Leu Pro Val Ile Asn Gln Ile Gln Ala Gly Glu Pro Ser
            35                  40                  45

Pro Tyr Gln Pro Val Asn Asn Leu Thr Ala Pro Glu Gly Glu Glu
        50                  55                  60

Val Ala Leu Lys Trp Asp Thr Pro Ser Ala Lys Lys Ala Glu Ala Ser
65                  70                  75                  80

Arg Glu Val Lys Arg Ile Gly Asp Gly Leu Phe Val Thr Ile Glu Pro
                85                  90                  95

Ala Asn Asp Val Arg Ala Asn Glu Ala Lys Val Val Leu Ala Ala Asp
                100                 105                 110

Asn Val Trp Gly Asp Asn Thr Gly Tyr Gln Phe Leu Leu Asp Ala Asp
            115                 120                 125

His Asn Thr Phe Gly Ser Val Ile Pro Ala Thr Gly Pro Leu Phe Thr
130                 135                 140

Gly Thr Ala Ser Ser Asn Leu Tyr Ser Ala Asn Phe Glu Tyr Leu Ile
145                 150                 155                 160

Pro Ala Asn Ala Asp Pro Val Val Thr Thr Gln Asn Ile Ile Val Thr
                165                 170                 175

Gly Gln Gly Glu Val Val Ile Pro Gly Gly Val Tyr Asp Tyr Cys Ile
            180                 185                 190

Thr Asn Pro Glu Pro Ala Ser Gly Lys Met Trp Ile Ala Gly Asp Gly
        195                 200                 205

Asp Asn Gln Pro Ala Arg Tyr Asp Asp Phe Thr Phe Glu Ala Gly Lys
210                 215                 220

Lys Tyr Thr Phe Thr Met Arg Arg Ala Gly Met Gly Asp Gly Thr Asp
225                 230                 235                 240

Met Glu Val Glu Asp Asp Ser Pro Ala Ser Tyr Thr Tyr Thr Val Tyr
                245                 250                 255

Arg Asp Gly Thr Lys Ile Lys Glu Gly Leu Thr Ala Thr Thr Phe Glu
            260                 265                 270

Glu Asp Gly Val Ala Ala Gly Asn His Glu Tyr Cys Val Glu Val Lys
        275                 280                 285
```

```
Tyr  Thr  Ala  Gly  Val  Ser  Pro  Lys  Val  Cys  Lys  Asp  Val  Thr  Val  Glu
     290                 295                 300

Gly  Ser  Asn  Glu  Phe  Ala  Pro  Val  Gln  Asn  Leu  Thr  Gly  Ser  Ala  Val
305                      310                 315                           320

Gly  Gln  Lys  Val  Thr  Leu  Lys  Trp  Asp  Pro  Asn  Gly  Thr  Pro  Asn
                    325                      330                      335

Pro  Asn  Pro  Asn  Pro  Asn  Pro  Gly  Thr  Thr  Leu  Ser  Glu  Ser  Phe
               340                 345                      350

Glu  Asn  Gly  Ile  Pro  Ala  Ser  Trp  Lys  Thr  Ile  Asp  Ala  Asp  Gly  Asp
               355                 360                      365

Gly  His  Gly  Trp  Lys  Pro  Gly  Asn  Ala  Pro  Gly  Ile  Ala  Gly  Tyr  Asn
     370                      375                 380

Ser  Asn  Gly  Cys  Val  Tyr  Ser  Glu  Ser  Phe  Gly  Leu  Gly  Gly  Ile  Gly
385                      390                 395                           400

Val  Leu  Thr  Pro  Asp  Asn  Tyr  Leu  Ile  Thr  Pro  Ala  Leu  Asp  Leu  Ala
               405                 410                      415

Asn  Gly  Gly  Lys  Leu  Thr  Phe  Trp  Val  Cys  Ala  Gln  Asp  Ala  Asn  Tyr
               420                 425                      430

Ala  Ser  Glu  His  Tyr  Ala  Val  Tyr  Ala  Ser  Ser  Thr  Gly  Asn  Asp  Ala
          435                      440                      445

Ser  Asn  Phe  Thr  Asn  Ala  Leu  Leu  Glu  Glu  Thr  Ile  Thr  Ala  Lys  Gly
     450                      455                 460

Val  Arg  Ser  Pro  Glu  Ala  Ile  Arg  Gly  Arg  Ile  Gln  Gly  Thr  Trp  Arg
465                      470                 475                           480

Gln  Lys  Thr  Val  Asp  Leu  Pro  Ala  Gly  Thr  Lys  Tyr  Val  Ala  Phe  Arg
                    485                 490                           495

His  Phe  Gln  Ser  Thr  Asp  Met  Phe  Tyr  Ile  Asp  Leu  Asp  Glu  Val  Glu
               500                 505                      510

Ile  Lys  Ala  Asn  Gly  Lys  Arg  Ala  Asp  Phe  Thr  Glu  Thr  Phe  Glu  Ser
          515                 520                      525

Ser  Thr  His  Gly  Glu  Ala  Pro  Ala  Glu  Trp  Thr  Thr  Ile  Asp  Ala  Asp
     530                      535                 540

Gly  Asp  Gly  Gln  Asp  Trp  Leu  Cys  Leu  Ser  Ser  Gly  Gln  Leu  Asp  Trp
545                      550                 555                           560

Leu  Thr  Ala  His  Gly  Gly  Thr  Asn  Val  Val  Ala  Ser  Phe  Ser  Trp  Asn
               565                      570                      575

Gly  Met  Ala  Leu  Asn  Pro  Asp  Asn  Tyr  Leu  Ile  Ser  Lys  Asp  Val  Thr
               580                 585                      590

Gly  Ala  Thr  Lys  Val  Lys  Tyr  Tyr  Ala  Val  Asn  Asp  Gly  Phe  Pro
               595                 600                 605

Gly  Asp  His  Tyr  Ala  Val  Met  Ile  Ser  Lys  Thr  Gly  Thr  Asn  Ala  Gly
     610                      615                 620

Asp  Phe  Thr  Val  Val  Phe  Glu  Glu  Thr  Pro  Asn  Gly  Ile  Asn  Lys  Gly
625                      630                 635                           640

Gly  Ala  Arg  Phe  Gly  Leu  Ser  Thr  Glu  Ala  Asn  Gly  Ala  Lys  Pro  Gln
               645                 650                      655

Ser  Val  Trp  Ile  Glu  Arg  Thr  Val  Asp  Leu  Pro  Ala  Gly  Thr  Lys  Tyr
               660                 665                      670

Val  Ala  Phe  Arg  His  Tyr  Asn  Cys  Ser  Asp  Leu  Asp  Tyr  Ile  Leu  Leu
               675                 680                      685

Asp  Asp  Ile  Gln  Phe  Thr  Met  Gly  Gly  Ser  Pro  Thr  Pro  Thr  Asp  Tyr
               690                 695                      700

Thr  Tyr  Thr  Val  Tyr  Arg  Asp  Gly  Thr  Lys  Ile  Lys  Glu  Gly  Leu  Thr
705                      710                 715                           720
```

| Glu | Thr | Thr | Phe | Glu | Glu | Asp | Gly | Val | Ala | Thr | Gly | Asn | His | Glu | Tyr |
|---|---|---|---|---|---|---|---|---|---|---|---|---|---|---|---|
| | | | | 725 | | | | | 730 | | | | | 735 | |

| Cys | Val | Glu | Val | Lys | Tyr | Thr | Ala | Gly | Val | Ser | Pro | Lys | Val | Cys | Val |
|---|---|---|---|---|---|---|---|---|---|---|---|---|---|---|---|
| | | | 740 | | | | | 745 | | | | | 750 | | |

| Asn | Val | Thr | Ile | Asn | Pro | Thr | Gln | Phe | Asn | Pro | Val | Lys | Asn | Leu | Lys |
|---|---|---|---|---|---|---|---|---|---|---|---|---|---|---|---|
| | | 755 | | | | | 760 | | | | | 765 | | | |

| Ala | Gln | Pro | Asp | Gly | Gly | Asp | Val | Val | Leu | Lys | Trp | Glu | Ala | Pro | Ser |
|---|---|---|---|---|---|---|---|---|---|---|---|---|---|---|---|
| | 770 | | | | | 775 | | | | | | 780 | | | |

| Gly | Lys | Arg | Gly | Glu | Leu | Leu | Asn | Glu | Asp | Phe | Glu | Gly | Asp | Ala | Ile |
|---|---|---|---|---|---|---|---|---|---|---|---|---|---|---|---|
| 785 | | | | | 790 | | | | | 795 | | | | | 800 |

| Pro | Thr | Gly | Trp | Thr | Ala | Leu | Asp | Ala | Asp | Gly | Asp | Gly | Asn | Asn | Trp |
|---|---|---|---|---|---|---|---|---|---|---|---|---|---|---|---|
| | | | | 805 | | | | | 810 | | | | | 815 | |

| Asp | Ile | Thr | Leu | Asn | Glu | Phe | Thr | Arg | Gly | Glu | Arg | His | Val | Leu | Ser |
|---|---|---|---|---|---|---|---|---|---|---|---|---|---|---|---|
| | | | 820 | | | | | 825 | | | | | 830 | | |

| Pro | Leu | Arg | Ala | Ser | Asn | Val | Ala | Ile | Ser | Tyr | Ser | Ser | Leu | Leu | Gln |
|---|---|---|---|---|---|---|---|---|---|---|---|---|---|---|---|
| | | 835 | | | | | 840 | | | | | 845 | | | |

| Gly | Gln | Glu | Tyr | Leu | Pro | Leu | Thr | Pro | Asn | Asn | Phe | Leu | Ile | Thr | Pro |
|---|---|---|---|---|---|---|---|---|---|---|---|---|---|---|---|
| | 850 | | | | | 855 | | | | | 860 | | | | |

| Lys | Val | Glu | Gly | Ala | Lys | Lys | Ile | Thr | Tyr | Lys | Val | Gly | Ser | Pro | Gly |
|---|---|---|---|---|---|---|---|---|---|---|---|---|---|---|---|
| 865 | | | | | 870 | | | | | 875 | | | | | 880 |

| Leu | Pro | Gln | Trp | Ser | His | Asp | His | Tyr | Ala | Leu | Cys | Ile | Ser | Lys | Ser |
|---|---|---|---|---|---|---|---|---|---|---|---|---|---|---|---|
| | | | | 885 | | | | | 890 | | | | | 895 | |

| Gly | Thr | Ala | Ala | Ala | Asp | Phe | Glu | Val | Ile | Phe | Glu | Glu | Thr | Met | Thr |
|---|---|---|---|---|---|---|---|---|---|---|---|---|---|---|---|
| | | | 900 | | | | | 905 | | | | | 910 | | |

| Tyr | Thr | Gln | Gly | Gly | Ala | Asn | Leu | Thr | Arg | Glu | Lys | Asp | Leu | Pro | Ala |
|---|---|---|---|---|---|---|---|---|---|---|---|---|---|---|---|
| | | 915 | | | | | 920 | | | | | 925 | | | |

| Gly | Thr | Lys | Tyr | Val | Ala | Phe | Arg | His | Tyr | Asn | Cys | Thr | Asp | Val | Leu |
|---|---|---|---|---|---|---|---|---|---|---|---|---|---|---|---|
| | 930 | | | | | 935 | | | | | 940 | | | | |

| Gly | Ile | Met | Ile | Asp | Asp | Val | Val | Ile | Thr | Gly | Glu | Gly | Glu | Gly | Pro |
|---|---|---|---|---|---|---|---|---|---|---|---|---|---|---|---|
| 945 | | | | | 950 | | | | | 955 | | | | | 960 |

| Ser | Tyr | Thr | Tyr | Thr | Val | Tyr | Arg | Asp | Gly | Thr | Lys | Ile | Gln | Glu | Gly |
|---|---|---|---|---|---|---|---|---|---|---|---|---|---|---|---|
| | | | | 965 | | | | | 970 | | | | | 975 | |

| Leu | Thr | Glu | Thr | Thr | Tyr | Arg | Asp | Ala | Gly | Met | Ser | Ala | Gln | Ser | His |
|---|---|---|---|---|---|---|---|---|---|---|---|---|---|---|---|
| | | | 980 | | | | | 985 | | | | | 990 | | |

| Glu | Tyr | Cys | Val | Glu | Val | Lys | Tyr | Ala | Ala | Gly | Val | Ser | Pro | Lys | Val |
|---|---|---|---|---|---|---|---|---|---|---|---|---|---|---|---|
| | | 995 | | | | | 1000 | | | | | 1005 | | | |

| Cys | Val | Asp | Tyr | Ile | Pro | Asp | Gly | Val | Ala | Asp | Val | Thr | Ala | Gln | Lys |
|---|---|---|---|---|---|---|---|---|---|---|---|---|---|---|---|
| | 1010 | | | | | 1015 | | | | | 1020 | | | | |

| Pro | Tyr | Thr | Leu | Thr | Val | Val | Gly | Lys | Thr | Ile | Thr | Val | Thr | Cys | Gln |
|---|---|---|---|---|---|---|---|---|---|---|---|---|---|---|---|
| 1025 | | | | | 1030 | | | | | 1035 | | | | | 1040 |

| Gly | Glu | Ala | Met | Ile | Tyr | Asp | Met | Asn | Gly | Arg | Arg | Leu | Ala | Ala | Gly |
|---|---|---|---|---|---|---|---|---|---|---|---|---|---|---|---|
| | | | | 1045 | | | | | 1050 | | | | | 1055 | |

| Arg | Asn | Thr | Val | Val | Tyr | Thr | Ala | Gln | Gly | Gly | Tyr | Tyr | Ala | Val | Met |
|---|---|---|---|---|---|---|---|---|---|---|---|---|---|---|---|
| | | | 1060 | | | | | 1065 | | | | | 1070 | | |

| Val | Val | Val | Asp | Gly | Lys | Ser | Tyr | Val | Glu | Lys | Leu | Ala | Ile | Lys |
|---|---|---|---|---|---|---|---|---|---|---|---|---|---|---|
| | | 1075 | | | | | 1080 | | | | | 1085 | | |

( 2 ) INFORMATION FOR SEQ ID NO:9:

( i ) SEQUENCE CHARACTERISTICS:
        ( A ) LENGTH: 6895 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
    ( A ) NAME/KEY: CDS
    ( B ) LOCATION: 696..5894

( x i ) SEQUENCE DESCRIPTION: SEQ ID NO:9:

```
GGATCCTACG CCCGATACCC ATACTCGAAG CCTTTGCTCA GTACCATCCT GCAGAAGGTT        60

ACTCTTTCGC ATATAGTGAC CCTCTTTTCT CTCAGCATAA TGGTACCTAT CATATCAGTA       120

AGGGGCGTAT TGTCTTTTCG AACAATGTAC AGCCCGAGAA CTCTTTACTT CCACATCACA       180

CCCCCGACTC CTTAGTCAAG GATCTTTTTT CCCCTTTCCC CTCCGCTCTC TTCCTCATGC       240

TGGACTGACT TAACCTTGGT CTGCTCTACT TTTCGGTTGT AAATACATGC AACACAATAA       300

CTTTAAGTGT TGTTAGACAA CACTTTTACA AGACTCTGAC TTTTAATGAG GTGGAGCATG       360

AACCTTTTCC TCTTTCATCT TCTCCTTCAG ATTACAGTCA ATATTTGGC  AAAAGGCTAA       420

TTGACAGCCT TTTATAAGGG TTAATCCCTT GTGGCTTATA TTGAAAACAT GTTCTTTATA       480

ATCCGATACT CTTCTTAAAT CGAATTTTTT CTCTAAATTG CGCCGCAACA AAACTCCTTG       540

AGAAAAGTAC CAATAGAAAT AGAAGGTAGC ATTTTGCCTT TAAATTCCTT TTCTTTTCTT       600

GGATTGTTCT TGAAATGAAT CTTATTTGTG GATTTTTTT  GTTTTTTAA  CCCGGCCGTG       660

GTTCTCTGAA TCACGACCAT AAATTGTTTT AAAGT ATG AGG AAA TTA TTA TTG          713
                                     Met Arg Lys Leu Leu Leu
                                       1               5
```

```
CTG ATC GCG GCG TCC CTT TTG GGA GTT GGT CTT TAC GCC CAA AGC GCC         761
Leu Ile Ala Ala Ser Leu Leu Gly Val Gly Leu Tyr Ala Gln Ser Ala
         10                  15                  20

AAG ATT AAG CTT GAT GCT CCG ACT ACT CGA ACG ACA TGT ACG AAC AAT         809
Lys Ile Lys Leu Asp Ala Pro Thr Thr Arg Thr Thr Cys Thr Asn Asn
     25                  30                  35

AGC TTC AAG CAG TTC GAT GCA AGC TTT TCG TTC AAT GAA GTC GAG CTG         857
Ser Phe Lys Gln Phe Asp Ala Ser Phe Ser Phe Asn Glu Val Glu Leu
 40                  45                  50

ACA AAG GTG GAG ACC AAA GGT GGT ACT TTC GCC TCA GTG TCA ATT CCG         905
Thr Lys Val Glu Thr Lys Gly Gly Thr Phe Ala Ser Val Ser Ile Pro
 55                  60                  65                  70

GGT GCA TTC CCG ACC GGT GAG GTT GGT TCT CCC GAA GTG CCA GCA GTT         953
Gly Ala Phe Pro Thr Gly Glu Val Gly Ser Pro Glu Val Pro Ala Val
             75                  80                  85

AGG AAG TTG ATT GCT GTG CCT GTC GGA GCC ACA CCT GTT GTT CGC GTG        1001
Arg Lys Leu Ile Ala Val Pro Val Gly Ala Thr Pro Val Val Arg Val
         90                  95                 100

AAA AGT TTT ACC GAG CAA GTT TAC TCT CTG AAC CAA TAC GGT TCC GAA        1049
Lys Ser Phe Thr Glu Gln Val Tyr Ser Leu Asn Gln Tyr Gly Ser Glu
     105                 110                 115

AAA CTC ATG CCA CAT CAA CCC TCT ATG AGC AAG AGT GAT GAT CCC GAA        1097
Lys Leu Met Pro His Gln Pro Ser Met Ser Lys Ser Asp Asp Pro Glu
 120                 125                 130

AAG GTT CCC TTC GTT TAC AAT GCT GCT GCT TAT GCA CGC AAA GGT TTT        1145
Lys Val Pro Phe Val Tyr Asn Ala Ala Ala Tyr Ala Arg Lys Gly Phe
 135             140                 145                 150

GTC GGA CAA GAA CTG ACC CAA GTA GAA ATG TTG GGG ACA ATG CGT GGT        1193
Val Gly Gln Glu Leu Thr Gln Val Glu Met Leu Gly Thr Met Arg Gly
             155                 160                 165

GTT CGC ATT GCA GCT CTT ACC ATT AAT CCT GTT CAG TAT GAT GTG GTT        1241
Val Arg Ile Ala Ala Leu Thr Ile Asn Pro Val Gln Tyr Asp Val Val
         170                 175                 180

GCA AAC CAA TTG AAG GTT AGA AAC AAC ATC GAA ATT GAA GTA AGC TTT        1289
Ala Asn Gln Leu Lys Val Arg Asn Asn Ile Glu Ile Glu Val Ser Phe
     185                 190                 195
```

| | | | | | | | | | | | | | | | | |
|---|---|---|---|---|---|---|---|---|---|---|---|---|---|---|---|---|
| CAA | GGA | GCT | GAT | GAA | GTA | GCT | ACA | CAA | CGT | TTG | TAT | GAT | GCT | TCT | TTT | 1337 |
| Gln | Gly | Ala | Asp | Glu | Val | Ala | Thr | Gln | Arg | Leu | Tyr | Asp | Ala | Ser | Phe | |
| | 200 | | | | 205 | | | | | | 210 | | | | | |
| AGC | CCT | TAT | TTC | GAA | ACA | GCT | TAT | AAA | CAG | CTC | TTC | AAT | AGA | GAT | GTT | 1385 |
| Ser | Pro | Tyr | Phe | Glu | Thr | Ala | Tyr | Lys | Gln | Leu | Phe | Asn | Arg | Asp | Val | |
| 215 | | | | | 220 | | | | | 225 | | | | | 230 | |
| TAT | ACA | GAT | CAT | GGC | GAC | TTG | TAT | AAT | ACG | CCG | GTT | CGT | ATG | CTT | GTT | 1433 |
| Tyr | Thr | Asp | His | Gly | Asp | Leu | Tyr | Asn | Thr | Pro | Val | Arg | Met | Leu | Val | |
| | | | | 235 | | | | | 240 | | | | | 245 | | |
| GTT | GCA | GGT | GCA | AAA | TTC | AAA | GAA | GCT | CTC | AAG | CCT | TGG | CTC | ACT | TGG | 1481 |
| Val | Ala | Gly | Ala | Lys | Phe | Lys | Glu | Ala | Leu | Lys | Pro | Trp | Leu | Thr | Trp | |
| | | | 250 | | | | | 255 | | | | | 260 | | | |
| AAG | GCT | CAA | AAG | GGC | TTC | TAT | CTG | GAT | GTG | CAT | TAC | ACA | GAC | GAA | GCT | 1529 |
| Lys | Ala | Gln | Lys | Gly | Phe | Tyr | Leu | Asp | Val | His | Tyr | Thr | Asp | Glu | Ala | |
| | | 265 | | | | | 270 | | | | | 275 | | | | |
| GAA | GTA | GGA | ACG | ACA | AAC | GCC | TCT | ATC | AAG | GCA | TTT | ATT | CAC | AAG | AAA | 1577 |
| Glu | Val | Gly | Thr | Thr | Asn | Ala | Ser | Ile | Lys | Ala | Phe | Ile | His | Lys | Lys | |
| | 280 | | | | | 285 | | | | | 290 | | | | | |
| TAC | AAT | GAT | GGA | TTG | GCA | GCT | AGT | GCT | GCT | CCG | GTC | TTC | TTG | GCT | TTG | 1625 |
| Tyr | Asn | Asp | Gly | Leu | Ala | Ala | Ser | Ala | Ala | Pro | Val | Phe | Leu | Ala | Leu | |
| 295 | | | | | 300 | | | | | 305 | | | | | 310 | |
| GTT | GGT | GAC | ACT | GAC | GTT | ATT | AGC | GGA | GAA | AAA | GGA | AAG | AAA | ACA | AAA | 1673 |
| Val | Gly | Asp | Thr | Asp | Val | Ile | Ser | Gly | Glu | Lys | Gly | Lys | Lys | Thr | Lys | |
| | | | | 315 | | | | | 320 | | | | | 325 | | |
| AAA | GTT | ACC | GAC | TTG | TAT | TAC | AGT | GCA | GTC | GAT | GGC | GAC | TAT | TTC | CCT | 1721 |
| Lys | Val | Thr | Asp | Leu | Tyr | Tyr | Ser | Ala | Val | Asp | Gly | Asp | Tyr | Phe | Pro | |
| | | | 330 | | | | | 335 | | | | | 340 | | | |
| GAA | ATG | TAT | ACT | TTC | CGT | ATG | TCT | GCT | TCT | TCC | CCA | GAA | GAA | CTG | ACG | 1769 |
| Glu | Met | Tyr | Thr | Phe | Arg | Met | Ser | Ala | Ser | Ser | Pro | Glu | Glu | Leu | Thr | |
| | | 345 | | | | | 350 | | | | | 355 | | | | |
| AAC | ATC | ATT | GAT | AAG | GTA | TTG | ATG | TAT | GAA | AAG | GCT | ACT | ATG | CCA | GAT | 1817 |
| Asn | Ile | Ile | Asp | Lys | Val | Leu | Met | Tyr | Glu | Lys | Ala | Thr | Met | Pro | Asp | |
| | 360 | | | | | 365 | | | | | 370 | | | | | |
| AAG | AGT | TAT | TTG | GAG | AAA | GTT | CTC | TTG | ATT | GCA | GGT | GCA | GAT | TAT | AGC | 1865 |
| Lys | Ser | Tyr | Leu | Glu | Lys | Val | Leu | Leu | Ile | Ala | Gly | Ala | Asp | Tyr | Ser | |
| 375 | | | | | 380 | | | | | 385 | | | | | 390 | |
| TGG | AAT | TCC | CAG | GTA | GGT | CAG | CCA | ACC | ATT | AAA | TAC | GGT | ATG | CAG | TAC | 1913 |
| Trp | Asn | Ser | Gln | Val | Gly | Gln | Pro | Thr | Ile | Lys | Tyr | Gly | Met | Gln | Tyr | |
| | | | | 395 | | | | | 400 | | | | | 405 | | |
| TAC | TAC | AAC | CAA | GAG | CAT | GGT | TAT | ACC | GAC | GTG | TAC | AAC | TAT | CTC | AAA | 1961 |
| Tyr | Tyr | Asn | Gln | Glu | His | Gly | Tyr | Thr | Asp | Val | Tyr | Asn | Tyr | Leu | Lys | |
| | | | 410 | | | | | 415 | | | | | 420 | | | |
| GCC | CCT | TAT | ACA | GGT | TGC | TAC | AGT | CAT | TTG | AAT | ACC | GGA | GTC | AGC | TTT | 2009 |
| Ala | Pro | Tyr | Thr | Gly | Cys | Tyr | Ser | His | Leu | Asn | Thr | Gly | Val | Ser | Phe | |
| | | 425 | | | | | 430 | | | | | 435 | | | | |
| GCA | AAC | TAT | ACA | GCG | CAT | GGA | TCT | GAG | ACC | GCA | TGG | GCT | GAT | CCA | CTT | 2057 |
| Ala | Asn | Tyr | Thr | Ala | His | Gly | Ser | Glu | Thr | Ala | Trp | Ala | Asp | Pro | Leu | |
| | 440 | | | | | 445 | | | | | 450 | | | | | |
| CTG | ACT | ACT | TCT | CAA | CTG | AAA | GCA | CTC | ACT | AAT | AAG | GAC | AAA | TAC | TTC | 2105 |
| Leu | Thr | Thr | Ser | Gln | Leu | Lys | Ala | Leu | Thr | Asn | Lys | Asp | Lys | Tyr | Phe | |
| 455 | | | | | 460 | | | | | 465 | | | | | 470 | |
| TTA | GCT | ATT | GGC | AAC | TGC | TGT | ATT | ACA | GCT | CAA | TTC | GAT | TAT | GTA | CAG | 2153 |
| Leu | Ala | Ile | Gly | Asn | Cys | Cys | Ile | Thr | Ala | Gln | Phe | Asp | Tyr | Val | Gln | |
| | | | | 475 | | | | | 480 | | | | | 485 | | |
| CCT | TGC | TTC | GGA | GAG | GTA | ATA | ACT | CGC | GTT | AAG | GAG | AAA | GGG | GCT | TAT | 2201 |
| Pro | Cys | Phe | Gly | Glu | Val | Ile | Thr | Arg | Val | Lys | Glu | Lys | Gly | Ala | Tyr | |
| | | | 490 | | | | | 495 | | | | | 500 | | | |
| GCC | TAT | ATC | GGT | TCA | TCT | CCA | AAT | TCT | TAT | TGG | GGC | GAG | GAC | TAC | TAT | 2249 |
| Ala | Tyr | Ile | Gly | Ser | Ser | Pro | Asn | Ser | Tyr | Trp | Gly | Glu | Asp | Tyr | Tyr | |
| | | 505 | | | | | 510 | | | | | 515 | | | | |

```
TGG  AGT  GTG  GGT  GCT  AAT  GCC  GTA  TTT  GGT  GTT  CAG  CCT  ACT  TTT  GAA   2297
Trp  Ser  Val  Gly  Ala  Asn  Ala  Val  Phe  Gly  Val  Gln  Pro  Thr  Phe  Glu
     520                 525                           530

GGT  ACG  TCT  ATG  GGT  TCT  TAT  GAT  GCT  ACA  TTC  TTG  GAG  GAT  TCG  TAC   2345
Gly  Thr  Ser  Met  Gly  Ser  Tyr  Asp  Ala  Thr  Phe  Leu  Glu  Asp  Ser  Tyr
535                      540                      545                      550

AAC  ACA  GTG  AAT  TCT  ATT  ATG  TGG  GCA  GGT  AAT  CTT  GCC  GCT  ACT  CAT   2393
Asn  Thr  Val  Asn  Ser  Ile  Met  Trp  Ala  Gly  Asn  Leu  Ala  Ala  Thr  His
                    555                 560                      565

GCT  GGA  AAT  ATC  GGC  AAT  ATT  ACC  CAT  ATT  GGT  GCT  CAT  TAC  TAT  TGG   2441
Ala  Gly  Asn  Ile  Gly  Asn  Ile  Thr  His  Ile  Gly  Ala  His  Tyr  Tyr  Trp
               570                 575                      580

GAA  GCT  TAT  CAT  GTC  CTT  GGC  GAT  GGT  TCG  GTT  ATG  CCT  TAT  CGT  GCA   2489
Glu  Ala  Tyr  His  Val  Leu  Gly  Asp  Gly  Ser  Val  Met  Pro  Tyr  Arg  Ala
          585                      590                      595

ATG  CCT  AAG  ACC  AAT  ACT  TAT  ACG  CTT  CCT  GCC  TCT  TTG  CCT  CAG  AAT   2537
Met  Pro  Lys  Thr  Asn  Thr  Tyr  Thr  Leu  Pro  Ala  Ser  Leu  Pro  Gln  Asn
600                      605                      610

CAG  GCT  TCT  TAT  AGC  ATT  CAG  GCT  TCT  GCC  GGT  TCT  TAC  GTA  GCT  ATT   2585
Gln  Ala  Ser  Tyr  Ser  Ile  Gln  Ala  Ser  Ala  Gly  Ser  Tyr  Val  Ala  Ile
615                      620                      625                      630

TCT  AAA  GAT  GGA  GTT  TTG  TAT  GGA  ACA  GGT  GTT  GCT  AAT  GCC  AGC  GGT   2633
Ser  Lys  Asp  Gly  Val  Leu  Tyr  Gly  Thr  Gly  Val  Ala  Asn  Ala  Ser  Gly
               635                      640                      645

GTT  GCG  ACT  GTG  AGT  ATG  ACT  AAG  CAG  ATT  ACG  GAA  AAT  GGT  AAT  TAT   2681
Val  Ala  Thr  Val  Ser  Met  Thr  Lys  Gln  Ile  Thr  Glu  Asn  Gly  Asn  Tyr
               650                      655                      660

GAT  GTA  GTT  ATC  ACT  CGC  TCT  AAT  TAT  CTT  CCT  GTG  ATC  AAG  CAA  ATT   2729
Asp  Val  Val  Ile  Thr  Arg  Ser  Asn  Tyr  Leu  Pro  Val  Ile  Lys  Gln  Ile
          665                      670                      675

CAG  GTA  GGT  GAG  CCT  AGC  CCC  TAC  CAG  CCC  GTT  TCC  AAC  TTG  ACA  GCT   2777
Gln  Val  Gly  Glu  Pro  Ser  Pro  Tyr  Gln  Pro  Val  Ser  Asn  Leu  Thr  Ala
680                      685                      690

ACA  ACG  CAG  GGT  CAG  AAA  GTA  ACG  CTC  AAG  TGG  GAA  GCA  CCG  AGC  GCA   2825
Thr  Thr  Gln  Gly  Gln  Lys  Val  Thr  Leu  Lys  Trp  Glu  Ala  Pro  Ser  Ala
695                      700                      705                      710

AAG  AAG  GCA  GAA  GGT  TCC  CGT  GAA  GTA  AAA  CGG  ATC  GGA  GAC  GGT  CTT   2873
Lys  Lys  Ala  Glu  Gly  Ser  Arg  Glu  Val  Lys  Arg  Ile  Gly  Asp  Gly  Leu
               715                      720                      725

TTC  GTT  ACG  ATC  GAA  CCT  GCA  AAC  GAT  GTA  CGT  GCC  AAC  GAA  GCC  AAG   2921
Phe  Val  Thr  Ile  Glu  Pro  Ala  Asn  Asp  Val  Arg  Ala  Asn  Glu  Ala  Lys
               730                      735                      740

GTT  GTG  CTT  GCG  GCA  GAC  AAC  GTA  TGG  GGA  GAC  AAT  ACG  GGT  TAC  CAG   2969
Val  Val  Leu  Ala  Ala  Asp  Asn  Val  Trp  Gly  Asp  Asn  Thr  Gly  Tyr  Gln
               745                      750                      755

TTC  TTG  TTG  GAT  GCC  GAT  CAC  AAT  ACA  TTC  GGA  AGT  GTC  ATT  CCG  GCA   3017
Phe  Leu  Leu  Asp  Ala  Asp  His  Asn  Thr  Phe  Gly  Ser  Val  Ile  Pro  Ala
760                      765                      770

ACC  GGT  CCT  CTC  TTT  ACC  GGA  ACA  GCT  TCT  TCC  AAT  CTT  TAC  AGT  GCG   3065
Thr  Gly  Pro  Leu  Phe  Thr  Gly  Thr  Ala  Ser  Ser  Asn  Leu  Tyr  Ser  Ala
775                      780                      785                      790

AAC  TTC  GAG  TAT  TTG  GTC  CCG  GCC  AAT  GCC  GAT  CCT  GTT  GTT  ACT  ACA   3113
Asn  Phe  Glu  Tyr  Leu  Val  Pro  Ala  Asn  Ala  Asp  Pro  Val  Val  Thr  Thr
               795                      800                      805

CAG  AAT  ATT  ATC  GTT  ACA  GGA  CAG  GGT  GAA  GTT  GTA  ATC  CCC  GGT  GGT   3161
Gln  Asn  Ile  Ile  Val  Thr  Gly  Gln  Gly  Glu  Val  Val  Ile  Pro  Gly  Gly
               810                      815                      820

GTT  TAC  GAC  TAT  TGC  ATT  ACG  AAC  CCG  GAA  CCT  GCA  TCC  GGA  AAG  ATG   3209
Val  Tyr  Asp  Tyr  Cys  Ile  Thr  Asn  Pro  Glu  Pro  Ala  Ser  Gly  Lys  Met
825                      830                      835
```

| | | | | | | | | | | | | | | | | |
|---|---|---|---|---|---|---|---|---|---|---|---|---|---|---|---|---|
| TGG | ATC | GCA | GGA | GAT | GGA | GGC | AAC | CAG | CCT | GCA | CGT | TAT | GAC | GAT | TTC | 3257 |
| Trp | Ile | Ala | Gly | Asp | Gly | Gly | Asn | Gln | Pro | Ala | Arg | Tyr | Asp | Asp | Phe | |
| 840 | | | | | 845 | | | | | 850 | | | | | | |
| ACA | TTC | GAA | GCA | GGC | AAG | AAG | TAC | ACC | TTC | ACG | ATG | CGT | CGC | GCC | GGA | 3305 |
| Thr | Phe | Glu | Ala | Gly | Lys | Lys | Tyr | Thr | Phe | Thr | Met | Arg | Arg | Ala | Gly | |
| 855 | | | | | 860 | | | | | 865 | | | | | 870 | |
| ATG | GGA | GAT | GGA | ACT | GAT | ATG | GAA | GTC | GAA | GAC | GAT | TCA | CCT | GCA | AGC | 3353 |
| Met | Gly | Asp | Gly | Thr | Asp | Met | Glu | Val | Glu | Asp | Asp | Ser | Pro | Ala | Ser | |
| | | | | 875 | | | | | 880 | | | | | 885 | | |
| TAT | ACC | TAC | ACG | GTG | TAT | CGT | GAC | GGC | ACG | AAG | ATC | AAG | GAA | GGT | CTG | 3401 |
| Tyr | Thr | Tyr | Thr | Val | Tyr | Arg | Asp | Gly | Thr | Lys | Ile | Lys | Glu | Gly | Leu | |
| | | | | 890 | | | | | 895 | | | | | 900 | | |
| ACA | GCT | ACG | ACA | TTC | GAA | GAA | GAC | GGT | GTA | GCT | GCA | GGC | AAT | CAT | GAG | 3449 |
| Thr | Ala | Thr | Thr | Phe | Glu | Glu | Asp | Gly | Val | Ala | Ala | Gly | Asn | His | Glu | |
| | | 905 | | | | | 910 | | | | | 915 | | | | |
| TAT | TGC | GTG | GAA | GTT | AAG | TAC | ACA | GCC | GGC | GTA | TCT | CCG | AAG | GTA | TGT | 3497 |
| Tyr | Cys | Val | Glu | Val | Lys | Tyr | Thr | Ala | Gly | Val | Ser | Pro | Lys | Val | Cys | |
| 920 | | | | | 925 | | | | | 930 | | | | | | |
| AAA | GAC | GTT | ACG | GTA | GAA | GGA | TCC | AAT | GAA | TTT | GCT | CCT | GTA | CAG | AAC | 3545 |
| Lys | Asp | Val | Thr | Val | Glu | Gly | Ser | Asn | Glu | Phe | Ala | Pro | Val | Gln | Asn | |
| 935 | | | | | 940 | | | | | 945 | | | | | 950 | |
| CTG | ACC | GGT | AGT | TCA | GTA | GGT | CAG | AAA | GTA | ACG | CTT | AAG | TGG | GAT | GCA | 3593 |
| Leu | Thr | Gly | Ser | Ser | Val | Gly | Gln | Lys | Val | Thr | Leu | Lys | Trp | Asp | Ala | |
| | | | | 955 | | | | | 960 | | | | | 965 | | |
| CCT | AAT | GGT | ACC | CCG | AAT | CCG | AAT | CCA | AAT | CCG | AAT | CCG | AAT | CCG | GGA | 3641 |
| Pro | Asn | Gly | Thr | Pro | Asn | Pro | Asn | Pro | Asn | Pro | Asn | Pro | Asn | Pro | Gly | |
| | | | 970 | | | | | 975 | | | | | 980 | | | |
| ACA | ACA | CTT | TCC | GAA | TCA | TTC | GAA | AAT | GGT | ATT | CCG | GCA | TCT | TGG | AAG | 3689 |
| Thr | Thr | Leu | Ser | Glu | Ser | Phe | Glu | Asn | Gly | Ile | Pro | Ala | Ser | Trp | Lys | |
| | | 985 | | | | | 990 | | | | | 995 | | | | |
| ACG | ATC | GAT | GCA | GAC | GGT | GAC | GGG | CAT | GGC | TGG | AAA | CCT | GGA | AAT | GCT | 3737 |
| Thr | Ile | Asp | Ala | Asp | Gly | Asp | Gly | His | Gly | Trp | Lys | Pro | Gly | Asn | Ala | |
| | 1000 | | | | | 1005 | | | | | 1010 | | | | | |
| CCC | GGA | ATC | GCT | GGC | TAC | AAT | AGC | AAT | GGT | TGT | GTA | TAT | TCA | GAG | TCA | 3785 |
| Pro | Gly | Ile | Ala | Gly | Tyr | Asn | Ser | Asn | Gly | Cys | Val | Tyr | Ser | Glu | Ser | |
| 1015 | | | | | 1020 | | | | | 1025 | | | | | 1030 | |
| TTC | GGT | CTT | GGT | GGT | ATA | GGA | GTT | CTT | ACC | CCT | GAC | AAC | TAT | CTG | ATA | 3833 |
| Phe | Gly | Leu | Gly | Gly | Ile | Gly | Val | Leu | Thr | Pro | Asp | Asn | Tyr | Leu | Ile | |
| | | | | 1035 | | | | | 1040 | | | | | 1045 | | |
| ACA | CCG | GCA | TTG | GAT | TTG | CCT | AAC | GGA | GGT | AAG | TTG | ACT | TTC | TGG | GTA | 3881 |
| Thr | Pro | Ala | Leu | Asp | Leu | Pro | Asn | Gly | Gly | Lys | Leu | Thr | Phe | Trp | Val | |
| | | | 1050 | | | | | 1055 | | | | | 1060 | | | |
| TGC | GCA | CAG | GAT | GCT | AAT | TAT | GCA | TCC | GAG | CAC | TAT | GCG | GTG | TAT | GCA | 3929 |
| Cys | Ala | Gln | Asp | Ala | Asn | Tyr | Ala | Ser | Glu | His | Tyr | Ala | Val | Tyr | Ala | |
| | | 1065 | | | | | 1070 | | | | | 1075 | | | | |
| TCT | TCG | ACC | GGT | AAC | GAT | GCA | TCC | AAC | TTC | ACG | AAT | GCT | TTG | TTG | GAA | 3977 |
| Ser | Ser | Thr | Gly | Asn | Asp | Ala | Ser | Asn | Phe | Thr | Asn | Ala | Leu | Leu | Glu | |
| | 1080 | | | | | 1085 | | | | | 1090 | | | | | |
| GAG | ACG | ATT | ACG | GCA | AAA | GGT | GTT | CGC | TCG | CCG | AAA | GCT | ATT | CGT | GGT | 4025 |
| Glu | Thr | Ile | Thr | Ala | Lys | Gly | Val | Arg | Ser | Pro | Lys | Ala | Ile | Arg | Gly | |
| 1095 | | | | | 1100 | | | | | 1105 | | | | | 1110 | |
| CGT | ATA | CAG | GGT | ACT | TGG | CGC | CAG | AAG | ACG | GTA | GAC | CTT | CCC | GCA | GGT | 4073 |
| Arg | Ile | Gln | Gly | Thr | Trp | Arg | Gln | Lys | Thr | Val | Asp | Leu | Pro | Ala | Gly | |
| | | | | 1115 | | | | | 1120 | | | | | 1125 | | |
| ACG | AAA | TAT | GTT | GCT | TTC | CGT | CAC | TTC | CAA | AGC | ACG | GAT | ATG | TTC | TAC | 4121 |
| Thr | Lys | Tyr | Val | Ala | Phe | Arg | His | Phe | Gln | Ser | Thr | Asp | Met | Phe | Tyr | |
| | | | | 1130 | | | | | 1135 | | | | | 1140 | | |
| ATC | GAC | CTT | GAT | GAG | GTT | GAG | ATC | AAG | GCC | AAT | GGC | AAG | CGC | GCA | GAC | 4169 |
| Ile | Asp | Leu | Asp | Glu | Val | Glu | Ile | Lys | Ala | Asn | Gly | Lys | Arg | Ala | Asp | |
| | | | 1145 | | | | | 1150 | | | | | 1155 | | | |

```
TTC ACG GAA ACG TTC GAG TCT TCT ACT CAT GGA GAG GCA CCA GCG GAA          4217
Phe Thr Glu Thr Phe Glu Ser Ser Thr His Gly Glu Ala Pro Ala Glu
        1160                    1165                    1170

TGG ACT ACT ATC GAT GCC GAT GGC GAT GGT CAG GGT TGG CTC TGT CTG          4265
Trp Thr Thr Ile Asp Ala Asp Gly Asp Gly Gln Gly Trp Leu Cys Leu
1175                    1180                    1185                1190

TCT TCC GGA CAA TTG GAC TGG CTG ACA GCT CAT GGC GGC AGC AAC GTA          4313
Ser Ser Gly Gln Leu Asp Trp Leu Thr Ala His Gly Gly Ser Asn Val
                1195                    1200                    1205

GTA AGC TCT TTC TCA TGG AAT GGA ATG GCT TTG AAT CCT GAT AAC TAT          4361
Val Ser Ser Phe Ser Trp Asn Gly Met Ala Leu Asn Pro Asp Asn Tyr
            1210                    1215                    1220

CTC ATC TCA AAG GAT GTT ACA GGC GCA ACG AAG GTA AAG TAC TAC TAT          4409
Leu Ile Ser Lys Asp Val Thr Gly Ala Thr Lys Val Lys Tyr Tyr Tyr
        1225                    1230                    1235

GCA GTC AAC GAC GGT TTT CCC GGG GAT CAC TAT GCG GTG ATG ATC TCC          4457
Ala Val Asn Asp Gly Phe Pro Gly Asp His Tyr Ala Val Met Ile Ser
1240                    1245                    1250

AAG ACG GGC ACG AAC GCC GGA GAC TTC ACG GTT GTT TTC GAA GAA ACG          4505
Lys Thr Gly Thr Asn Ala Gly Asp Phe Thr Val Val Phe Glu Glu Thr
                1255                    1260                    1265                    1270

CCT AAC GGA ATA AAT AAG GGC GGA GCA AGA TTC GGT CTT TCC ACG GAA          4553
Pro Asn Gly Ile Asn Lys Gly Gly Ala Arg Phe Gly Leu Ser Thr Glu
                    1275                    1280                    1285

GCC AAT GGC GCC AAA CCT CAA AGT GTA TGG ATC GAG CGT ACG GTA GAT          4601
Ala Asn Gly Ala Lys Pro Gln Ser Val Trp Ile Glu Arg Thr Val Asp
                1290                    1295                    1300

TTG CCT GCA GGC ACG AAG TAT GTT GCT TTC CGT CAC TAC AAT TGC TCG          4649
Leu Pro Ala Gly Thr Lys Tyr Val Ala Phe Arg His Tyr Asn Cys Ser
        1305                    1310                    1315

GAT TTG AAC TAC ATT CTT TTG GAT GAT ATT CAG TTC ACC ATG GGT GGC          4697
Asp Leu Asn Tyr Ile Leu Leu Asp Asp Ile Gln Phe Thr Met Gly Gly
    1320                    1325                    1330

AGC CCC ACC CCG ACC GAT TAT ACC TAC ACG GTG TAT CGT GAT GGT ACG          4745
Ser Pro Thr Pro Thr Asp Tyr Thr Tyr Thr Val Tyr Arg Asp Gly Thr
1335                    1340                    1345                    1350

AAG ATC AAG GAA GGT TTG ACC GAA ACG ACC TTC GAA GAA GAC GGC GTA          4793
Lys Ile Lys Glu Gly Leu Thr Glu Thr Thr Phe Glu Glu Asp Gly Val
                    1355                    1360                    1365

GCT ACG GGC AAT CAT GAG TAT TGC GTG GAA GTG AAG TAC ACA GCC GGC          4841
Ala Thr Gly Asn His Glu Tyr Cys Val Glu Val Lys Tyr Thr Ala Gly
                1370                    1375                    1380

GTA TCT CCG AAG AAA TGT GTA GAC GTA ACT GTT AAT TCG ACA CAG TTC          4889
Val Ser Pro Lys Lys Cys Val Asp Val Thr Val Asn Ser Thr Gln Phe
        1385                    1390                    1395

AAT CCT GTA CAG AAC CTG ACG GCA GAA CAA GCT CCT AAC AGC ATG GAT          4937
Asn Pro Val Gln Asn Leu Thr Ala Glu Gln Ala Pro Asn Ser Met Asp
    1400                    1405                    1410

GCA ATC CTT AAA TGG AAT GCA CCG GCA TCT AAG CGT GCG GAA GTT CTG          4985
Ala Ile Leu Lys Trp Asn Ala Pro Ala Ser Lys Arg Ala Glu Val Leu
1415                    1420                    1425                    1430

AAC GAA GAC TTC GAA AAT GGT ATT CCT GCC TCA TGG AAG ACG ATC GAT          5033
Asn Glu Asp Phe Glu Asn Gly Ile Pro Ala Ser Trp Lys Thr Ile Asp
                    1435                    1440                    1445

GCA GAC GGT GAC GGC AAC AAT TGG ACG ACG ACC CCT CCT CCC GGA GGC          5081
Ala Asp Gly Asp Gly Asn Asn Trp Thr Thr Thr Pro Pro Pro Gly Gly
                1450                    1455                    1460

TCC TCT TTT GCA GGT CAC AAC AGT GCG ATC TGT GTC TCT TCA GCT TCT          5129
Ser Ser Phe Ala Gly His Asn Ser Ala Ile Cys Val Ser Ser Ala Ser
        1465                    1470                    1475
```

| | | | | | | | | | | | | | | | | |
|---|---|---|---|---|---|---|---|---|---|---|---|---|---|---|---|---|
| CAT | ATC | AAC | TTT | GAA | GGT | CCT | CAG | AAC | CCT | GAT | AAC | TAT | CTG | GTT | ACA | 5177 |
| His | Ile | Asn | Phe | Glu | Gly | Pro | Gln | Asn | Pro | Asp | Asn | Tyr | Leu | Val | Thr | |
| | | | 1480 | | | | 1485 | | | | 1490 | | | | | |
| CCG | GAG | CTT | TCT | CTT | CCT | GGC | GGA | GGA | ACG | CTT | ACT | TTC | TGG | GTA | TGT | 5225 |
| Pro | Glu | Leu | Ser | Leu | Pro | Gly | Gly | Gly | Thr | Leu | Thr | Phe | Trp | Val | Cys | |
| 1495 | | | | | 1500 | | | | | 1505 | | | | | 1510 | |
| GCA | CAA | GAT | GCC | AAT | TAT | GCA | TCA | GAG | CAC | TAT | GCC | GTG | TAC | GCA | TCT | 5273 |
| Ala | Gln | Asp | Ala | Asn | Tyr | Ala | Ser | Glu | His | Tyr | Ala | Val | Tyr | Ala | Ser | |
| | | | | 1515 | | | | | 1520 | | | | | 1525 | | |
| TCT | ACG | GGT | AAC | GAC | GCT | TCC | AAC | TTC | GCC | AAC | GCT | TTG | TTG | GAA | GAA | 5321 |
| Ser | Thr | Gly | Asn | Asp | Ala | Ser | Asn | Phe | Ala | Asn | Ala | Leu | Leu | Glu | Glu | |
| | | | | 1530 | | | | | 1535 | | | | | 1540 | | |
| GTG | CTG | ACG | GCC | AAG | ACA | GTT | GTT | ACG | GCA | CCT | GAA | GCC | ATT | CGT | GGT | 5369 |
| Val | Leu | Thr | Ala | Lys | Thr | Val | Val | Thr | Ala | Pro | Glu | Ala | Ile | Arg | Gly | |
| | | | 1545 | | | | | 1550 | | | | | 1555 | | | |
| ACT | CGT | GCT | CAG | GGC | ACC | TGG | TAT | CAA | AAG | ACG | GTA | CAG | TTG | CCT | GCG | 5417 |
| Thr | Arg | Ala | Gln | Gly | Thr | Trp | Tyr | Gln | Lys | Thr | Val | Gln | Leu | Pro | Ala | |
| | | | 1560 | | | | | 1565 | | | | | 1570 | | | |
| GGT | ACT | AAG | TAT | GTT | GCC | TTC | CGT | CAC | TTC | GGC | TGT | ACG | GAC | TTC | TTC | 5465 |
| Gly | Thr | Lys | Tyr | Val | Ala | Phe | Arg | His | Phe | Gly | Cys | Thr | Asp | Phe | Phe | |
| 1575 | | | | | 1580 | | | | | 1585 | | | | | 1590 | |
| TGG | ATC | AAC | CTT | GAT | GAT | GTT | GTA | ATC | ACT | TCA | GGG | AAC | GCT | CCG | TCT | 5513 |
| Trp | Ile | Asn | Leu | Asp | Asp | Val | Val | Ile | Thr | Ser | Gly | Asn | Ala | Pro | Ser | |
| | | | | 1595 | | | | | 1600 | | | | | 1605 | | |
| TAC | ACC | TAT | ACG | ATC | TAT | CGT | AAT | AAT | ACA | CAG | ATA | GCA | TCA | GGC | GTA | 5561 |
| Tyr | Thr | Tyr | Thr | Ile | Tyr | Arg | Asn | Asn | Thr | Gln | Ile | Ala | Ser | Gly | Val | |
| | | | 1610 | | | | | 1615 | | | | | 1620 | | | |
| ACG | GAG | ACT | ACT | TAC | CGA | GAT | CCG | GAC | TTG | GCT | ACC | GGT | TTT | TAC | ACG | 5609 |
| Thr | Glu | Thr | Thr | Tyr | Arg | Asp | Pro | Asp | Leu | Ala | Thr | Gly | Phe | Tyr | Thr | |
| | | | 1625 | | | | | 1630 | | | | | 1635 | | | |
| TAC | GGT | GTA | AAG | GTT | GTT | TAC | CCG | AAC | GGA | GAA | TCA | GCT | ATC | GAA | ACT | 5657 |
| Tyr | Gly | Val | Lys | Val | Val | Tyr | Pro | Asn | Gly | Glu | Ser | Ala | Ile | Glu | Thr | |
| 1640 | | | | | 1645 | | | | | 1650 | | | | | | |
| GCT | ACG | TTG | AAT | ATC | ACT | TCG | TTG | GCA | GAC | GTA | ACG | GCT | CAG | AAG | CCT | 5705 |
| Ala | Thr | Leu | Asn | Ile | Thr | Ser | Leu | Ala | Asp | Val | Thr | Ala | Gln | Lys | Pro | |
| 1655 | | | | | 1660 | | | | | 1665 | | | | | 1670 | |
| TAC | ACG | CTG | ACA | GTT | GTA | GGA | AAG | ACG | ATC | ACG | GTA | ACT | TGC | CAA | GGC | 5753 |
| Tyr | Thr | Leu | Thr | Val | Val | Gly | Lys | Thr | Ile | Thr | Val | Thr | Cys | Gln | Gly | |
| | | | | 1675 | | | | | 1680 | | | | | 1685 | | |
| GAA | GCT | ATG | ATC | TAC | GAC | ATG | AAC | GGT | CGT | CGT | CTG | GCA | GCG | GGT | CGC | 5801 |
| Glu | Ala | Met | Ile | Tyr | Asp | Met | Asn | Gly | Arg | Arg | Leu | Ala | Ala | Gly | Arg | |
| | | | 1690 | | | | | 1695 | | | | | 1700 | | | |
| AAC | ACG | GTT | GTT | TAC | ACG | GCT | CAG | GGC | GGC | CAC | TAT | GCA | GTC | ATG | GTT | 5849 |
| Asn | Thr | Val | Val | Tyr | Thr | Ala | Gln | Gly | Gly | His | Tyr | Ala | Val | Met | Val | |
| | | | 1705 | | | | | 1710 | | | | | 1715 | | | |
| GTC | GTT | GAC | GGC | AAG | TCT | TAC | GTA | GAG | AAA | CTC | GCT | GTA | AAG | TAAATCTGTC | | 5901 |
| Val | Val | Asp | Gly | Lys | Ser | Tyr | Val | Glu | Lys | Leu | Ala | Val | Lys | | | |
| | | | 1720 | | | | | 1725 | | | | | 1730 | | | |

| | | | | |
|---|---|---|---|---|
| TTGGACTCGG | AGACTTTGTG | CAGACACTTT | TAAGATAGGT | CTGTAATTGT | CTCAGAGTAT | 5961 |
| GAATCGGTCG | CCCGACTTCC | TTAAAGGAG | GTCGGGCGAC | TTCGTTTTTA | TTATTGCTGT | 6021 |
| CCGGTAAACT | TGTCAAGAGG | AGACCTTTGA | AAAATGAGAC | CTTTGCACGG | CGATTGGTGT | 6081 |
| GTATTTGTT | TGTTAATTCA | TTGTATAATA | GGGAGTTATT | TTGTATATTT | GAGTATTAAA | 6141 |
| AACAGCATAA | TATTCCTCCC | ATGGCATACC | AATCCAAGAA | TACCGATGAG | CATGTAACAT | 6201 |
| TTGCAGACGC | ACTCCTTTCA | AAGCGTTATC | GCAAAGCACA | AAACGACTTC | CTCAATCAGG | 6261 |
| TTGACAGGCT | TATCGATTGG | CGTCCGATCA | GGACGCTGAT | CAACAAGAAA | TACACGAAGC | 6321 |
| GACAAAATGC | CATCGGCGCC | CCGGCTTATG | ACGTGATTCT | CTTATTCAAG | ATGTTGCTTC | 6381 |

```
CGAAGACATG GTACAACCTC AGTGATTGTG CTTTGGAGGA GCGCATCAAT GATTCAATCA    6441

CCTTTTCCCG ATTCTTGGGG CTATGGAAGA GGTATCTCCC GACCACAGCA CCATCAGTCG    6501

ATTTCGTTCG GCACTGACAG AGTTGGGGCT CATGGACAAA CTATTGGCGC AGTTTAACAA    6561

ACAACTTTTC CGCCATCACA TTTCGGTCAG GGAAAGGGTG CTTGTCGATG CAAGCCTTGT    6621

GGAGATACGG AGCACCATCG AACGCACCTT TGGCAGTATT CGCCGGTGGT TTCATGGCGG    6681

ACGATGTCGA TACCGGGGAC TTGCCAAGAC CCATACTCAA AACATTCTTG AAAGCATCGC    6741

CTTTAATTTA TACAGAACCC CGGGGATAAT TATGTCCTCA TCTCTAGGAT AAGGTATAAC    6801

CACCCTTGAG GAGCTCGTGC AAGCAGCTCC TCAAGGGGGA TTTACAACTA CTTTCACTCC    6861

TTACCGCCAC CCTTTTCCCT CCCTCCCGGA ATTC                                 6895
```

(2) INFORMATION FOR SEQ ID NO:10:

(i) SEQUENCE CHARACTERISTICS:
        (A) LENGTH: 1732 amino acids
        (B) TYPE: amino acid
        (D) TOPOLOGY: linear (ii) MOLECULE TYPE: protein (xi) SEQUENCE DESCRIPTION: SEQ ID NO:10:

```
Met Arg Lys Leu Leu Leu Leu Ile Ala Ala Ser Leu Leu Gly Val Gly
 1               5                  10                  15

Leu Tyr Ala Gln Ser Ala Lys Ile Lys Leu Asp Ala Pro Thr Thr Arg
                20                  25                  30

Thr Thr Cys Thr Asn Asn Ser Phe Lys Gln Phe Asp Ala Ser Phe Ser
             35                  40                  45

Phe Asn Glu Val Glu Leu Thr Lys Val Glu Thr Lys Gly Gly Thr Phe
         50                  55                  60

Ala Ser Val Ser Ile Pro Gly Ala Phe Pro Thr Gly Glu Val Gly Ser
 65                  70                  75                  80

Pro Glu Val Pro Ala Val Arg Lys Leu Ile Ala Val Pro Val Gly Ala
                85                  90                  95

Thr Pro Val Val Arg Val Lys Ser Phe Thr Glu Gln Val Tyr Ser Leu
                100                 105                 110

Asn Gln Tyr Gly Ser Glu Lys Leu Met Pro His Gln Pro Ser Met Ser
            115                 120                 125

Lys Ser Asp Asp Pro Glu Lys Val Pro Phe Val Tyr Asn Ala Ala Ala
130                 135                 140

Tyr Ala Arg Lys Gly Phe Val Gly Gln Glu Leu Thr Gln Val Glu Met
145                 150                 155                 160

Leu Gly Thr Met Arg Gly Val Arg Ile Ala Ala Leu Thr Ile Asn Pro
                165                 170                 175

Val Gln Tyr Asp Val Val Ala Asn Gln Leu Lys Val Arg Asn Asn Ile
            180                 185                 190

Glu Ile Glu Val Ser Phe Gln Gly Ala Asp Glu Val Ala Thr Gln Arg
        195                 200                 205

Leu Tyr Asp Ala Ser Phe Ser Pro Tyr Phe Glu Thr Ala Tyr Lys Gln
    210                 215                 220

Leu Phe Asn Arg Asp Val Tyr Thr Asp His Gly Asp Leu Tyr Asn Thr
225                 230                 235                 240

Pro Val Arg Met Leu Val Val Ala Gly Ala Lys Phe Lys Glu Ala Leu
                245                 250                 255

Lys Pro Trp Leu Thr Trp Lys Ala Gln Lys Gly Phe Tyr Leu Asp Val
```

|     |     |     | 260 |     |     |     | 265 |     |     |     | 270 |     |     |     |
| --- | --- | --- | --- | --- | --- | --- | --- | --- | --- | --- | --- | --- | --- | --- |

His Tyr Thr Asp Glu Ala Glu Val Gly Thr Thr Asn Ala Ser Ile Lys
        275             280                 285

Ala Phe Ile His Lys Lys Tyr Asn Asp Gly Leu Ala Ala Ser Ala Ala
    290             295             300

Pro Val Phe Leu Ala Leu Val Gly Asp Thr Asp Val Ile Ser Gly Glu
305             310             315                         320

Lys Gly Lys Lys Thr Lys Lys Val Thr Asp Leu Tyr Tyr Ser Ala Val
                325             330                         335

Asp Gly Asp Tyr Phe Pro Glu Met Tyr Thr Phe Arg Met Ser Ala Ser
            340             345                 350

Ser Pro Glu Glu Leu Thr Asn Ile Ile Asp Lys Val Leu Met Tyr Glu
        355             360             365

Lys Ala Thr Met Pro Asp Lys Ser Tyr Leu Glu Lys Val Leu Leu Ile
    370             375             380

Ala Gly Ala Asp Tyr Ser Trp Asn Ser Gln Val Gly Gln Pro Thr Ile
385             390             395                         400

Lys Tyr Gly Met Gln Tyr Tyr Tyr Asn Gln Glu His Gly Tyr Thr Asp
                405             410                 415

Val Tyr Asn Tyr Leu Lys Ala Pro Tyr Thr Gly Cys Tyr Ser His Leu
            420             425                 430

Asn Thr Gly Val Ser Phe Ala Asn Tyr Thr Ala His Gly Ser Glu Thr
            435             440                 445

Ala Trp Ala Asp Pro Leu Leu Thr Thr Ser Gln Leu Lys Ala Leu Thr
    450             455             460

Asn Lys Asp Lys Tyr Phe Leu Ala Ile Gly Asn Cys Cys Ile Thr Ala
465             470             475                         480

Gln Phe Asp Tyr Val Gln Pro Cys Phe Gly Glu Val Ile Thr Arg Val
            485             490                 495

Lys Glu Lys Gly Ala Tyr Ala Tyr Ile Gly Ser Ser Pro Asn Ser Tyr
            500             505             510

Trp Gly Glu Asp Tyr Tyr Trp Ser Val Gly Ala Asn Ala Val Phe Gly
        515             520             525

Val Gln Pro Thr Phe Glu Gly Thr Ser Met Gly Ser Tyr Asp Ala Thr
    530             535             540

Phe Leu Glu Asp Ser Tyr Asn Thr Val Asn Ser Ile Met Trp Ala Gly
545             550             555                         560

Asn Leu Ala Ala Thr His Ala Gly Asn Ile Gly Asn Ile Thr His Ile
            565             570                 575

Gly Ala His Tyr Tyr Trp Glu Ala Tyr His Val Leu Gly Asp Gly Ser
            580             585                 590

Val Met Pro Tyr Arg Ala Met Pro Lys Thr Asn Thr Tyr Thr Leu Pro
        595             600             605

Ala Ser Leu Pro Gln Asn Gln Ala Ser Tyr Ser Ile Gln Ala Ser Ala
610             615             620

Gly Ser Tyr Val Ala Ile Ser Lys Asp Gly Val Leu Tyr Gly Thr Gly
625             630             635                         640

Val Ala Asn Ala Ser Gly Val Ala Thr Val Ser Met Thr Lys Gln Ile
            645             650                 655

Thr Glu Asn Gly Asn Tyr Asp Val Val Ile Thr Arg Ser Asn Tyr Leu
            660             665                 670

Pro Val Ile Lys Gln Ile Gln Val Gly Glu Pro Ser Pro Tyr Gln Pro
        675             680             685

```
Val Ser Asn Leu Thr Ala Thr Thr Gln Gly Gln Lys Val Thr Leu Lys
    690                 695                 700

Trp Glu Ala Pro Ser Ala Lys Lys Ala Glu Gly Ser Arg Glu Val Lys
705                 710                 715                 720

Arg Ile Gly Asp Gly Leu Phe Val Thr Ile Glu Pro Ala Asn Asp Val
                725                 730                 735

Arg Ala Asn Glu Ala Lys Val Val Leu Ala Ala Asp Asn Val Trp Gly
            740                 745                 750

Asp Asn Thr Gly Tyr Gln Phe Leu Leu Asp Ala Asp His Asn Thr Phe
        755                 760                 765

Gly Ser Val Ile Pro Ala Thr Gly Pro Leu Phe Thr Gly Thr Ala Ser
    770                 775                 780

Ser Asn Leu Tyr Ser Ala Asn Phe Glu Tyr Leu Val Pro Ala Asn Ala
785                 790                 795                 800

Asp Pro Val Val Thr Thr Gln Asn Ile Ile Val Thr Gly Gln Gly Glu
                805                 810                 815

Val Val Ile Pro Gly Gly Val Tyr Asp Tyr Cys Ile Thr Asn Pro Glu
            820                 825                 830

Pro Ala Ser Gly Lys Met Trp Ile Ala Gly Asp Gly Gly Asn Gln Pro
            835                 840                 845

Ala Arg Tyr Asp Asp Phe Thr Phe Glu Ala Gly Lys Lys Tyr Thr Phe
    850                 855                 860

Thr Met Arg Arg Ala Gly Met Gly Asp Gly Thr Asp Met Glu Val Glu
865                 870                 875                 880

Asp Asp Ser Pro Ala Ser Tyr Thr Tyr Thr Val Tyr Arg Asp Gly Thr
                885                 890                 895

Lys Ile Lys Glu Gly Leu Thr Ala Thr Thr Phe Glu Glu Asp Gly Val
            900                 905                 910

Ala Ala Gly Asn His Glu Tyr Cys Val Glu Val Lys Tyr Thr Ala Gly
            915                 920                 925

Val Ser Pro Lys Val Cys Lys Asp Val Thr Val Glu Gly Ser Asn Glu
    930                 935                 940

Phe Ala Pro Val Gln Asn Leu Thr Gly Ser Ser Val Gly Gln Lys Val
945                 950                 955                 960

Thr Leu Lys Trp Asp Ala Pro Asn Gly Thr Pro Asn Pro Asn Pro Asn
                965                 970                 975

Pro Asn Pro Asn Pro Gly Thr Thr Leu Ser Glu Ser Phe Glu Asn Gly
            980                 985                 990

Ile Pro Ala Ser Trp Lys Thr Ile Asp Ala Asp Gly Asp Gly His Gly
        995                 1000                1005

Trp Lys Pro Gly Asn Ala Pro Gly Ile Ala Gly Tyr Asn Ser Asn Gly
    1010                1015                1020

Cys Val Tyr Ser Glu Ser Phe Gly Leu Gly Gly Ile Gly Val Leu Thr
1025                1030                1035                1040

Pro Asp Asn Tyr Leu Ile Thr Pro Ala Leu Asp Leu Pro Asn Gly Gly
                1045                1050                1055

Lys Leu Thr Phe Trp Val Cys Ala Gln Asp Ala Asn Tyr Ala Ser Glu
            1060                1065                1070

His Tyr Ala Val Tyr Ala Ser Ser Thr Gly Asn Asp Ala Ser Asn Phe
        1075                1080                1085

Thr Asn Ala Leu Leu Glu Glu Thr Ile Thr Ala Lys Gly Val Arg Ser
    1090                1095                1100

Pro Lys Ala Ile Arg Gly Arg Ile Gln Gly Thr Trp Arg Gln Lys Thr
1105                1110                1115                1120
```

```
Val  Asp  Leu  Pro  Ala  Gly  Thr  Lys  Tyr  Val  Ala  Phe  Arg  His  Phe  Gln
               1125               1130                    1135

Ser  Thr  Asp  Met  Phe  Tyr  Ile  Asp  Leu  Asp  Glu  Val  Glu  Ile  Lys  Ala
               1140               1145                    1150

Asn  Gly  Lys  Arg  Ala  Asp  Phe  Thr  Glu  Thr  Phe  Glu  Ser  Ser  Thr  His
               1155               1160                    1165

Gly  Glu  Ala  Pro  Ala  Glu  Trp  Thr  Thr  Ile  Asp  Ala  Asp  Gly  Asp  Gly
     1170               1175                    1180

Gln  Gly  Trp  Leu  Cys  Leu  Ser  Ser  Gly  Gln  Leu  Asp  Trp  Leu  Thr  Ala
1185                1190                    1195                         1200

His  Gly  Gly  Ser  Asn  Val  Val  Ser  Ser  Phe  Ser  Trp  Asn  Gly  Met  Ala
               1205               1210                    1215

Leu  Asn  Pro  Asp  Asn  Tyr  Leu  Ile  Ser  Lys  Asp  Val  Thr  Gly  Ala  Thr
               1220               1225                    1230

Lys  Val  Lys  Tyr  Tyr  Tyr  Ala  Val  Asn  Asp  Gly  Phe  Pro  Gly  Asp  His
               1235               1240                    1245

Tyr  Ala  Val  Met  Ile  Ser  Lys  Thr  Gly  Thr  Asn  Ala  Gly  Asp  Phe  Thr
               1250               1255                    1260

Val  Val  Phe  Glu  Glu  Thr  Pro  Asn  Gly  Ile  Asn  Lys  Gly  Gly  Ala  Arg
1265                1270                    1275                         1280

Phe  Gly  Leu  Ser  Thr  Glu  Ala  Asn  Gly  Ala  Lys  Pro  Gln  Ser  Val  Trp
               1285               1290                    1295

Ile  Glu  Arg  Thr  Val  Asp  Leu  Pro  Ala  Gly  Thr  Lys  Tyr  Val  Ala  Phe
               1300               1305                    1310

Arg  His  Tyr  Asn  Cys  Ser  Asp  Leu  Asn  Tyr  Ile  Leu  Leu  Asp  Asp  Ile
               1315               1320                    1325

Gln  Phe  Thr  Met  Gly  Gly  Ser  Pro  Thr  Pro  Thr  Asp  Tyr  Thr  Tyr  Thr
               1330               1335                    1340

Val  Tyr  Arg  Asp  Gly  Thr  Lys  Ile  Lys  Glu  Gly  Leu  Thr  Glu  Thr  Thr
1345                1350                    1355                         1360

Phe  Glu  Glu  Asp  Gly  Val  Ala  Thr  Gly  Asn  His  Glu  Tyr  Cys  Val  Glu
               1365               1370                    1375

Val  Lys  Tyr  Thr  Ala  Gly  Val  Ser  Pro  Lys  Lys  Cys  Val  Asp  Val  Thr
               1380               1385                    1390

Val  Asn  Ser  Thr  Gln  Phe  Asn  Pro  Val  Gln  Asn  Leu  Thr  Ala  Glu  Gln
               1395               1400                    1405

Ala  Pro  Asn  Ser  Met  Asp  Ala  Ile  Leu  Lys  Trp  Asn  Ala  Pro  Ala  Ser
               1410               1415                    1420

Lys  Arg  Ala  Glu  Val  Leu  Asn  Glu  Asp  Phe  Glu  Asn  Gly  Ile  Pro  Ala
1425                1430                    1435                         1440

Ser  Trp  Lys  Thr  Ile  Asp  Ala  Asp  Gly  Asp  Gly  Asn  Asn  Trp  Thr  Thr
               1445               1450                    1455

Thr  Pro  Pro  Pro  Gly  Gly  Ser  Ser  Phe  Ala  Gly  His  Asn  Ser  Ala  Ile
               1460               1465                    1470

Cys  Val  Ser  Ser  Ala  Ser  His  Ile  Asn  Phe  Glu  Gly  Pro  Gln  Asn  Pro
               1475               1480                    1485

Asp  Asn  Tyr  Leu  Val  Thr  Pro  Glu  Leu  Ser  Leu  Pro  Gly  Gly  Gly  Thr
               1490               1495                    1500

Leu  Thr  Phe  Trp  Val  Cys  Ala  Gln  Asp  Ala  Asn  Tyr  Ala  Ser  Glu  His
1505                1510                    1515                         1520

Tyr  Ala  Val  Tyr  Ala  Ser  Ser  Thr  Gly  Asn  Asp  Ala  Ser  Asn  Phe  Ala
               1525               1530                    1535

Asn  Ala  Leu  Leu  Glu  Glu  Val  Leu  Thr  Ala  Lys  Thr  Val  Val  Thr  Ala
```

-continued

| | | 1540 | | | | | 1545 | | | | | 1550 | | |
|---|---|---|---|---|---|---|---|---|---|---|---|---|---|---|
| Pro | Glu | Ala | Ile | Arg | Gly | Thr | Arg | Ala | Gln | Gly | Thr | Trp | Tyr | Gln | Lys |
| | | 1555 | | | | | 1560 | | | | | 1565 | | |
| Thr | Val | Gln | Leu | Pro | Ala | Gly | Thr | Lys | Tyr | Val | Ala | Phe | Arg | His | Phe |
| | | 1570 | | | | | 1575 | | | | | 1580 | | |
| Gly | Cys | Thr | Asp | Phe | Phe | Trp | Ile | Asn | Leu | Asp | Asp | Val | Val | Ile | Thr |
| 1585 | | | | | 1590 | | | | | 1595 | | | | | 1600 |
| Ser | Gly | Asn | Ala | Pro | Ser | Tyr | Thr | Tyr | Thr | Ile | Tyr | Arg | Asn | Asn | Thr |
| | | | | 1605 | | | | | 1610 | | | | | 1615 | |
| Gln | Ile | Ala | Ser | Gly | Val | Thr | Glu | Thr | Thr | Tyr | Arg | Asp | Pro | Asp | Leu |
| | | | | 1620 | | | | | 1625 | | | | | 1630 | |
| Ala | Thr | Gly | Phe | Tyr | Thr | Tyr | Gly | Val | Lys | Val | Val | Tyr | Pro | Asn | Gly |
| | | | | 1635 | | | | | 1640 | | | | | 1645 | |
| Glu | Ser | Ala | Ile | Glu | Thr | Ala | Thr | Leu | Asn | Ile | Thr | Ser | Leu | Ala | Asp |
| | | 1650 | | | | | 1655 | | | | | 1660 | | | |
| Val | Thr | Ala | Gln | Lys | Pro | Tyr | Thr | Leu | Thr | Val | Val | Gly | Lys | Thr | Ile |
| 1665 | | | | | 1670 | | | | | 1675 | | | | | 1680 |
| Thr | Val | Thr | Cys | Gln | Gly | Glu | Ala | Met | Ile | Tyr | Asp | Met | Asn | Gly | Arg |
| | | | | 1685 | | | | | 1690 | | | | | 1695 | |
| Arg | Leu | Ala | Ala | Gly | Arg | Asn | Thr | Val | Val | Tyr | Thr | Ala | Gln | Gly | Gly |
| | | | | 1700 | | | | | 1705 | | | | | 1710 | |
| His | Tyr | Ala | Val | Met | Val | Val | Val | Asp | Gly | Lys | Ser | Tyr | Val | Glu | Lys |
| | | | | 1715 | | | | | 1720 | | | | | 1725 | |
| Leu | Ala | Val | Lys | | | | | | | | | | | | |
| | | | 1730 | | | | | | | | | | | | |

( 2 ) INFORMATION FOR SEQ ID NO:11:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

GGAATGGGAG ATGGAACT      18

( 2 ) INFORMATION FOR SEQ ID NO:12:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

GTAACCCGTA TTGTCTCC      18